United States Patent
Kopelman et al.

(10) Patent No.: US 11,957,531 B2
(45) Date of Patent: Apr. 16, 2024

(54) ORTHODONTIC SYSTEMS FOR MONITORING TREATMENT

(71) Applicant: Align Technology, Inc., San Jose, CA (US)

(72) Inventors: Avi Kopelman, Palo Alto, CA (US); Zelko Relic, Pleasanton, CA (US); Srinivas Kaza, Mountain View, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/868,666

(22) Filed: Jul. 19, 2022

(65) Prior Publication Data
US 2022/0354621 A1 Nov. 10, 2022

Related U.S. Application Data

(63) Continuation of application No. 16/220,381, filed on Dec. 14, 2018, now Pat. No. 11,432,908.
(Continued)

(51) Int. Cl.
*A61C 7/08* (2006.01)
*A61B 5/00* (2006.01)
(Continued)

(52) U.S. Cl.
CPC .............. *A61C 7/002* (2013.01); *A61B 5/1111* (2013.01); *A61B 5/682* (2013.01); *A61C 7/08* (2013.01); *A61C 19/04* (2013.01); *A61B 2562/0223* (2013.01); *A61B 2562/0247* (2013.01); *A61B 2562/0261* (2013.01)

(58) Field of Classification Search
CPC ........................................................ A61C 7/08
See application file for complete search history.

(56) References Cited

U.S. PATENT DOCUMENTS 5,680,874 A * 10/1997 Takuno ................. A61B 5/1111
600/587
5,989,023 A * 11/1999 Summer .............. A61C 19/045
433/69

(Continued)

FOREIGN PATENT DOCUMENTS

CN 104921833 A 9/2015

*Primary Examiner* — Heidi M Eide
(74) *Attorney, Agent, or Firm* — Shay Glenn LLP

(57) ABSTRACT

Orthodontic systems for monitoring treatment. The systems can include at least one orthodontic appliance that includes one or more sensors. A processor in communication with the sensor(s) is configured to receive sensor data from the sensor(s), where the sensor data corresponds to a force acting on one or more teeth. The processor is further configured to predict tooth movement based on the sensor data. The predicted tooth movement is determined by predicting how much teeth will move based on a direction and a magnitude of the force. The processor is further configured to compare the predicted tooth movement to an expected tooth movement, where the expected tooth movement is based on a treatment stage of a treatment plan. The processor is further configured to modify the treatment plan if the predicted tooth movement does not match the expected tooth movement based on the treatment stage of the treatment plan.

20 Claims, 30 Drawing Sheets

Related U.S. Application Data

(60) Provisional application No. 62/599,669, filed on Dec. 15, 2017.

(51) Int. Cl.
*A61B 5/11* (2006.01)
*A61C 7/00* (2006.01)
*A61C 19/04* (2006.01)

(56) References Cited

U.S. PATENT DOCUMENTS

| | | |
|---|---|---|
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,457,972 B1 | 10/2002 | Chishti et al. |
| 6,488,499 B1 | 12/2002 | Miller |
| 6,554,611 B2 | 4/2003 | Chishti et al. |
| 6,582,229 B1 | 6/2003 | Miller et al. |
| 6,688,886 B2 | 2/2004 | Hughes et al. |
| 6,726,478 B1 | 4/2004 | Isiderio et al. |
| 6,767,208 B2 | 7/2004 | Kaza |
| 6,783,360 B2 | 8/2004 | Chishti |
| 7,063,532 B1 | 6/2006 | Jones et al. |
| 7,074,038 B1 | 7/2006 | Miller |
| 7,108,508 B2 | 9/2006 | Hedge et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,736,147 B2 | 6/2010 | Kaza et al. |
| 7,844,356 B2 | 11/2010 | Matov et al. |
| 7,878,804 B2 | 2/2011 | Korytov et al. |
| 7,942,672 B2 | 5/2011 | Kuo |
| 8,044,954 B2 | 10/2011 | Kitching et al. |
| 8,260,591 B2 | 9/2012 | Kass et al. |
| 8,562,338 B2 | 10/2013 | Kitching et al. |
| 8,788,285 B2 | 7/2014 | Kuo |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,364,296 B2 | 6/2016 | Kuo |
| 10,342,638 B2 | 7/2019 | Kitching et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,123,156 B2 | 9/2021 | Cam et al. |
| 11,151,753 B2 | 10/2021 | Gao et al. |
| 11,154,381 B2 | 10/2021 | Roschin et al. |
| 11,154,382 B2 | 10/2021 | Kopelman et al. |
| 11,174,338 B2 | 11/2021 | Liska et al. |
| 11,219,506 B2 | 1/2022 | Shanjani et al. |
| 11,259,896 B2 | 3/2022 | Matov et al. |
| 11,318,667 B2 | 5/2022 | Mojdeh et al. |
| 11,331,166 B2 | 5/2022 | Morton et al. |
| 11,344,385 B2 | 5/2022 | Morton et al. |
| 11,357,598 B2 | 6/2022 | Cramer |
| 11,395,717 B2 | 7/2022 | Yuryev et al. |
| 11,464,604 B2 | 10/2022 | Makarenkova et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2005/0182654 A1 | 8/2005 | Abolfathi et al. |
| 2006/0127836 A1 | 6/2006 | Wen |
| 2006/0127852 A1 | 6/2006 | Wen |
| 2006/0127854 A1 | 6/2006 | Wen |
| 2010/0009308 A1 | 1/2010 | Wen et al. |
| 2010/0068672 A1 | 3/2010 | Arjomand et al. |
| 2010/0092907 A1 | 4/2010 | Knopp |
| 2010/0167243 A1 | 7/2010 | Spiridonov et al. |
| 2016/0310235 A1 | 10/2016 | Derakhshan et al. |
| 2017/0056131 A1* | 3/2017 | Alauddin .............. A61C 19/04 |
| 2017/0100214 A1* | 4/2017 | Wen ...................... G16H 30/20 |
| 2017/0251954 A1* | 9/2017 | Lotan ................... A61B 5/1128 |
| 2017/0252140 A1* | 9/2017 | Murphy ............... A61B 5/4833 |
| 2017/0273760 A1 | 9/2017 | Morton et al. |
| 2019/0053876 A1 | 2/2019 | Sterental et al. |
| 2019/0239983 A1 | 8/2019 | Matty |
| 2019/0328487 A1 | 10/2019 | Levin et al. |
| 2019/0328488 A1 | 10/2019 | Levin et al. |
| 2019/0333622 A1 | 10/2019 | Levin et al. |
| 2020/0000552 A1 | 1/2020 | Mednikov et al. |
| 2020/0085546 A1 | 3/2020 | Li et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0147672 A1 | 5/2021 | Cole et al. |
| 2021/0174477 A1 | 6/2021 | Shi et al. |

* cited by examiner

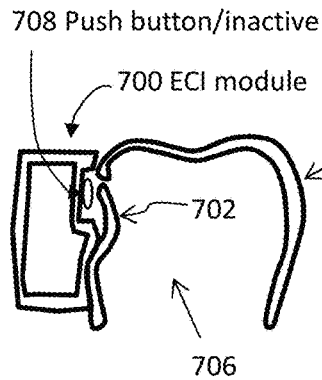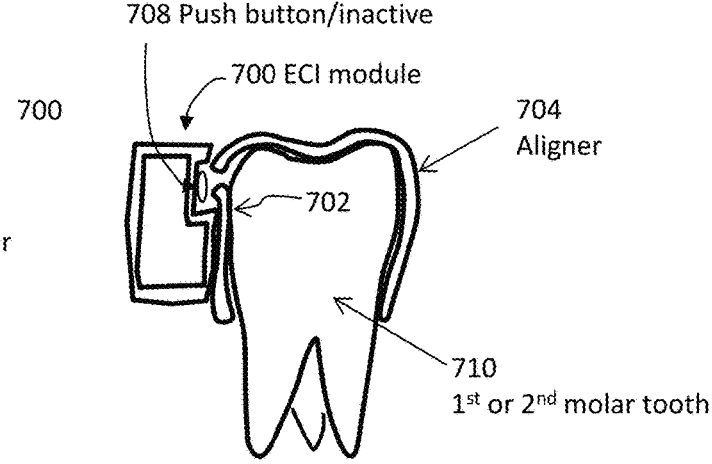
FIG. 7A
FIG. 7B
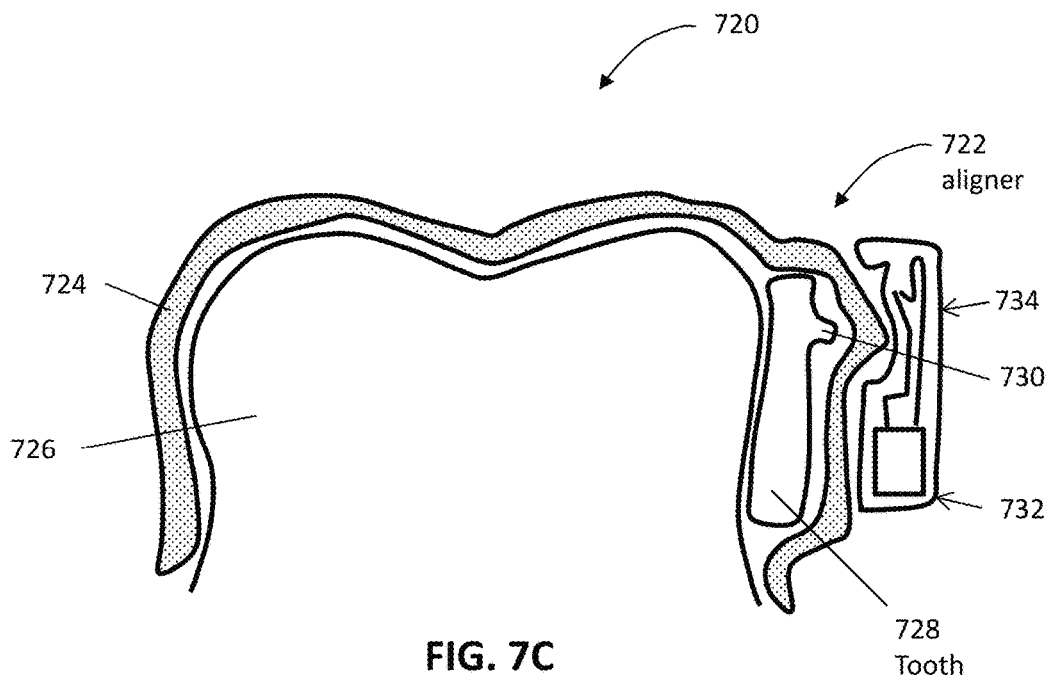
FIG. 7C

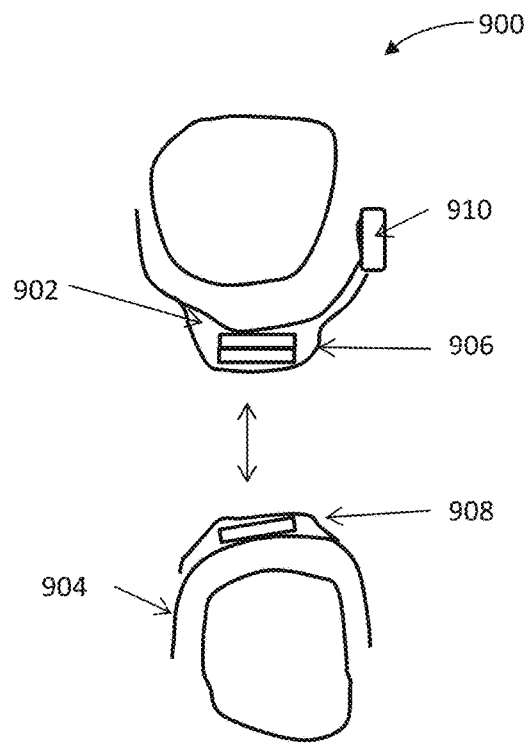
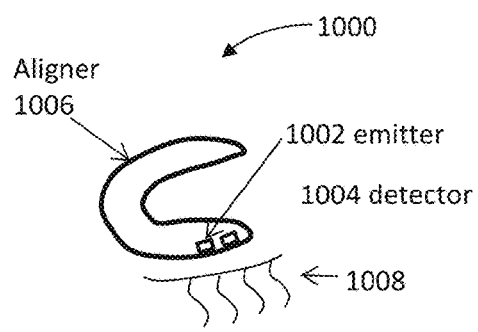
FIG. 9
FIG. 10A
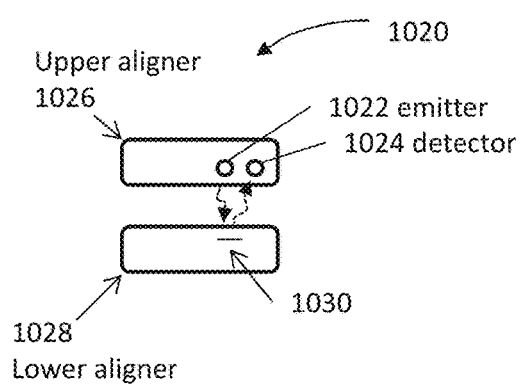
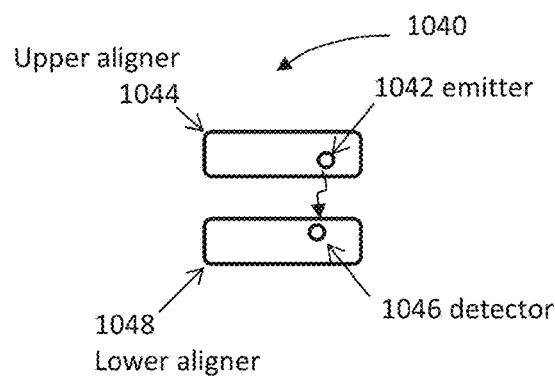
FIG. 10B
FIG. 10C

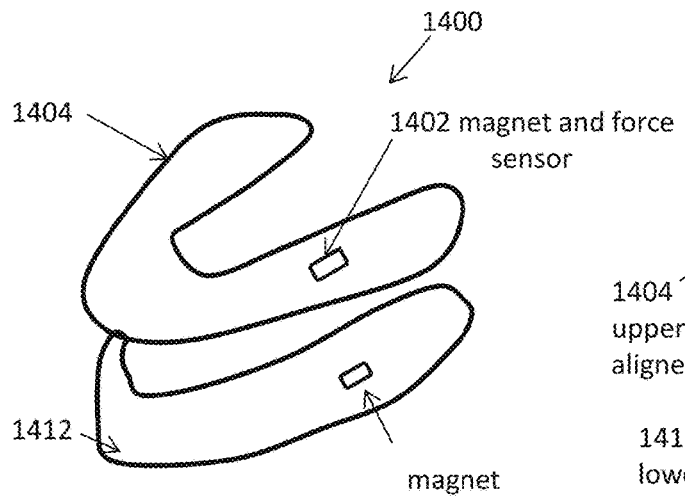
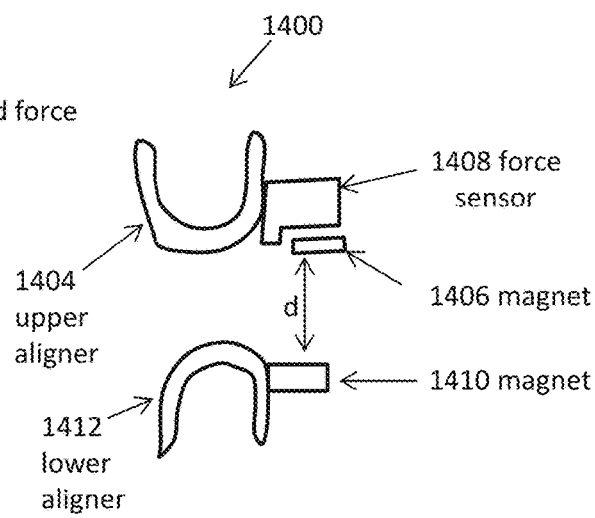
FIG. 14A
FIG. 14B
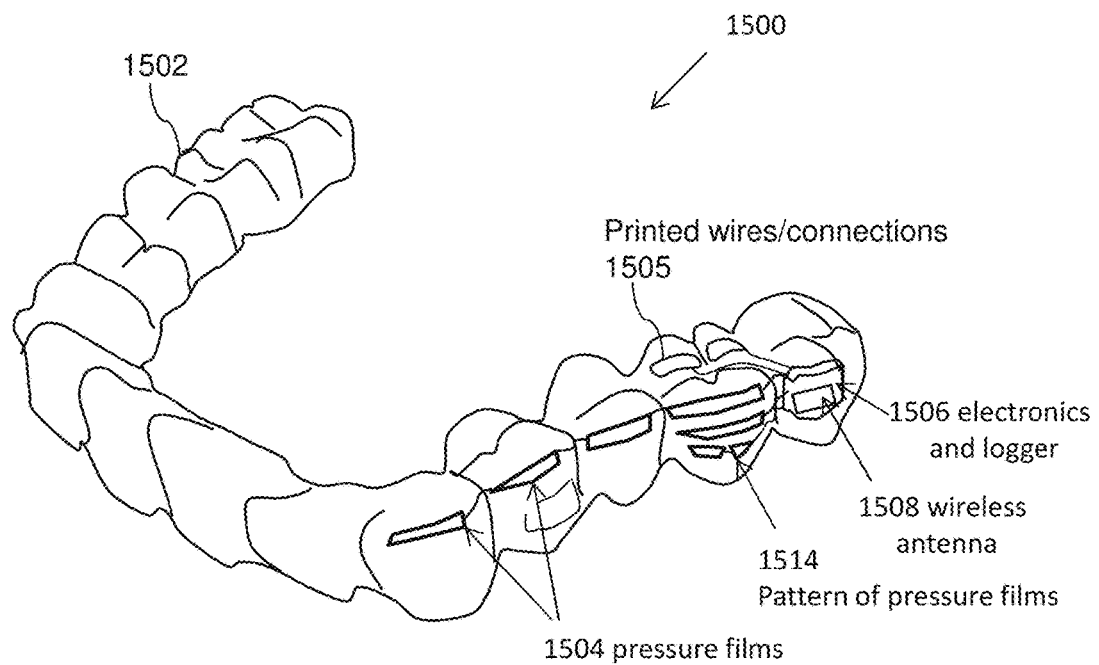
FIG. 15

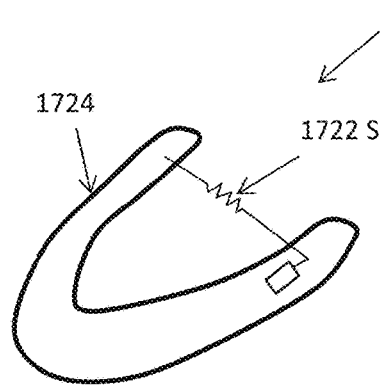
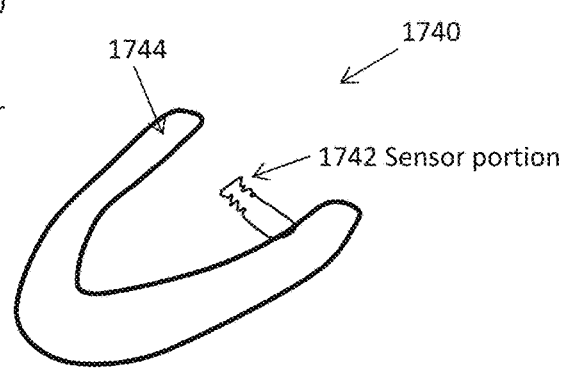
FIG. 17B  FIG. 17C
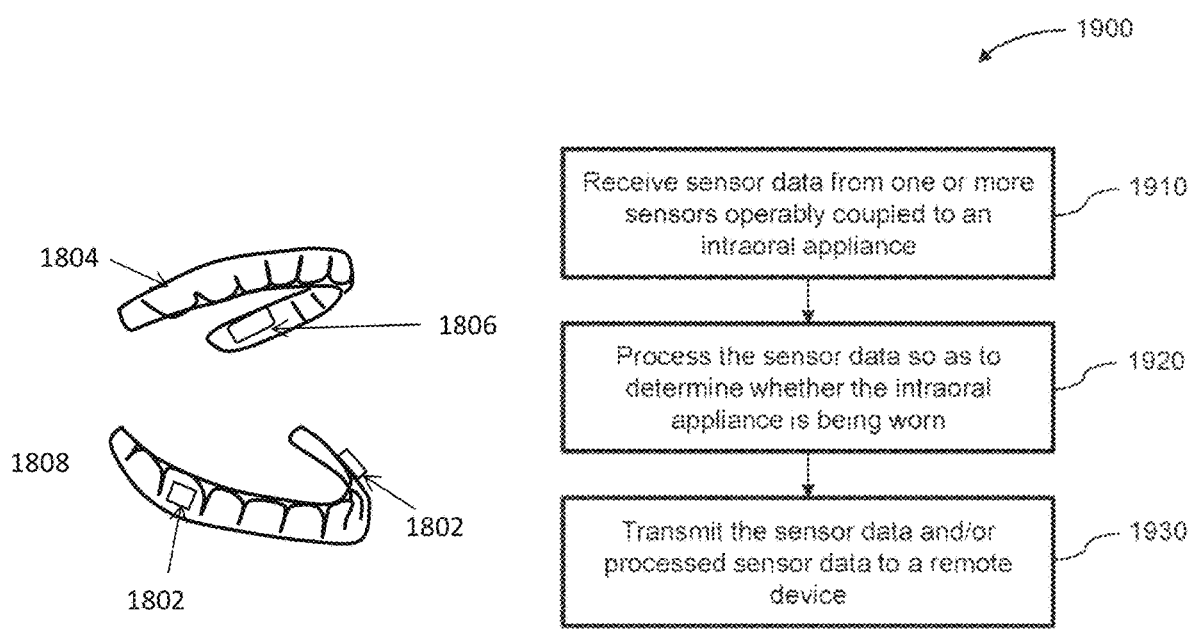
FIG. 18  FIG. 19

ORTHODONTIC SYSTEMS FOR MONITORING TREATMENT

CROSS REFERENCE TO RELATED APPLICATIONS

This patent application is a continuation of U.S. patent application Ser. No. 16/220,381, filed Dec. 14, 2018, titled "CLOSED LOOP ADAPTIVE ORTHODONTIC TREATMENT METHODS AND APPARATUSES," now U.S. Patent Application Publication No. 2019/0192259, which claims priority to U.S. Provisional Patent Application No. 62/599,669, filed on Dec. 15, 2017, and titled "CLOSED LOOP ADAPTIVE ORTHODONTIC TREATMENT METHODS AND APPARATUSES," each of which is herein incorporated by reference in its entirety.

This patent application may be related to U.S. patent application Ser. No. 15/625,872, filed on Jun. 16, 2017 (titled "INTRAORAL APPLIANCES WITH SENSING"), which claims priority to U.S. Provisional Patent Application No. 62/351,516, filed Jun. 17, 2016 (titled "EMBEDDED INTRAORAL SENSING FOR PHYSIOLOGICAL MONITORING AND TREATMENT WITH AN ORAL APPLIANCE"), U.S. Provisional Patent Application No. 62/351,391, filed Jun. 17, 2016 (titled "ELECTRONIC COMPLIANCE INDICATOR FOR INTRAORAL APPLIANCES") and U.S. Provisional Patent Application No. 62/483,283, filed Apr. 7, 2017 (titled "WIRELESS ELECTRONIC COMPLIANCE INDICATOR, READER CASE AND USER INTERFACE FOR INTRAORAL APPLIANCES"). This patent application may also be related to U.S. patent application Ser. No. 15/625,850, filed on Jun. 16, 2017 (titled ORTHODONTIC APPLIANCE PERFORMANCE MONITOR"), which claims priority to U.S. Provisional Patent Application No. 62/351,408, filed on Jun. 17, 2016. Each of these patents is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Orthodontic procedures typically involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner. The appliance can be configured to exert force on one or more teeth in order to effect desired tooth movements according to a treatment plan.

Orthodontic treatment with patient-removable appliances is traditionally manually monitored, e.g., by a dental practitioner. The patient may be responsible for wearing the appliances and switching the appliances within a treatment plan series as indicated by the treatment plan provided. The dental practitioner may adjust the treatment plan periodically, based, e.g., on observing the patient's teeth and other feedback, including patient feedback. In addition, it has been suggested that one or more sensors for monitoring the patient, the patient's teeth and/or the appliance itself may be included, and this information may be used by the dental practitioner to monitor compliance and the status of the patient's teeth and treatment plan.

However, it would be particularly useful to provide systems in which the treatment plan itself were modified or adjusted automatically, e.g., in a closed-loop or semi closed-loop manner (e.g., with oversight of the dental practitioner and/or patient) based on sensor data. Described herein are methods and apparatuses for providing such closed-loop or semi-closed loop control of an orthodontic treatment plan.

SUMMARY OF THE DISCLOSURE

Described herein are apparatuses, including devices and systems, including in particular appliances (e.g., orthodontic appliances) and methods for monitoring an orthodontic appliance, including, but not limited to monitoring tooth position, tooth movement, forces on the teeth, the status of the appliance, etc. and automatically or semi-automatically modifying the orthodontic treatment (e.g., treatment plan). The orthodontic treatment plan may be modified by, e.g., modifying one or more appliance in the treatment plan, including forming new appliances, changing the shape and/or duration for wearing one or more appliances in the treatment plan, modifying the patient's teeth (e.g., adding/removing/repositioning attachments, removing a tooth or teeth, interproximal reduction of a tooth, etc.), or the like.

In general, any appropriate sensor may be used. For example, a sensor may include an embedded sensor on or in the aligner. For example a sensor may generally be configured to sense one or more of: stress in the aligner, force applied on the teeth when wearing the aligner, direction of the force applied, and/or actual teeth movement and/or rotation of the teeth. Described herein are examples of sensors including force sensors, movement sensors, position sensors, and the like. These sensors may include one or more modalities, e.g., touch or tactile sensors (e.g., capacitive, resistive), proximity sensors, audio sensors (e.g., microelectromechanical system (MEMS) microphones), color sensors (e.g., RGB color sensors), electromagnetic sensors (e.g., magnetic reed sensors, magnetometer), light sensors, force sensors (e.g., force-dependent resistive materials), pressure sensors, temperature sensors, motion sensors (e.g., accelerometers, gyroscopes), vibration sensors, piezoelectric sensors, strain gauges, pH sensors, conductivity sensors, gas flow sensors, gas detection sensors, humidity or moisture sensors, physiological sensors (e.g., electrocardiography sensors, bio-impedance sensors, photoplethysmography sensors, galvanic skin response sensors), or combinations thereof. In some embodiments, the sensors herein can be configured as a switch that is activated and/or deactivated in response to a particular type of signal (e.g., optical, electrical, magnetic, mechanical, etc.).

In general, the closed- or semi closed-loop methods and apparatuses (devices, systems, etc.) described herein may including monitoring input from one or more sensors (which may be known positions on/in the appliance), and interpreting the input to determine one or more of: has the appliance done its work; when is the best time to replace the aligner with the next aligner in the sequence; which is the next best appliance from a set of pre-made appliances; should a new appliance (not yet in the sequence of appliances) be made, if it has not already been produced; should the treatment plan be modified or should the staging of the treatment plan be modified to achieve the end goal(s); and/or should the end goals of the treatment plan be modified.

The processing of sensor information may take place in a processor or multiple processors. The processor may receive sensor data directly or indirectly from the one or more sensor(s), e.g., from a memory storing the sensor data. The processor may receive the sensor data and may modify (e.g., average, sum, filter, etc.) the data. The processor may compare the data to the patient-specific treatment plan and/or general treatment guidelines (not specific to a particular patient). For example, the processor may compare the sensor data to expected values based on the patient-specific treatment plan and/or general treatment guidelines. The processor may therefore receive the expected values and or store the expected values in an accessible memory, and/or it may receive the treatment plan and generate expected values from the treatment plant. This analysis may be performed in real time and/or after a predetermined amount of time (e.g., aggregating sensor data) or on demand. The output of the analysis by the processor may be provided, e.g., to the dental professional, the patient, and/or an accessible database, accessible by the patient and/or dental professional. The output may be encrypted for patient security. The output may include the data used to generate the output (e.g., for further analysis, storage, etc.) and/or the output may include simplified instructions (e.g., "wear aligner for X additional days," "replace aligner now," "see dental professional," "wear Y aligner next," etc.).

Processing of the information can be done intra orally by a processor associated with the appliance and one or multiple sensors. The processing may be done offline (e.g., by a remote processor, and/or by a user device, such as a smartphone, tablet, etc., in communication with the appliance and/or any sensor(s) on the appliance. For example, if there are multiple sensors, they may optionally transmit to a processor on the appliance that is configured to perform the analysis. Alternatively, the sensor(s) may transmit the information to an external computing device (e.g., smartphone) including the processor.

In some variations, the apparatus may initially analyze forces acting on the appliance when first worn. For example, if the appliance is an aligner, the apparatus may, at the time that an aligner is applied, analyze the force system and report an expected efficacy of that aligner including a decision to use another aligner instead (e.g., either a prefabricated one in the treatment plan series, or a new one). In some variations, the apparatus may be configured to continuously track the treatment progress and analyze if there is a need to change aligner earlier than expected due to undesired movement of teeth.

The methods and apparatuses described herein may allow assessment of the progress of an orthodontic treatment plan that has a target end position, including assessing a patient's teeth during intermediate stages of a multi-stage orthodontic treatment plan and/or assessing the status of the appliance itself. Sensor data collected from one or more sensors on the appliance may determine the condition of the patient's dental arch and may be compared with a planned condition of the patient's dental arch, e.g., for an intermediate stage of the multi-stage orthodontic treatment plan. Based on this comparison, one or more clinical signs that the actual condition of the patient's dental arch has a deviation from the planned condition of the patient's dental arch, e.g., for the intermediate stage of a multi-stage orthodontic treatment plan may be identified. In some variations, one or more probable root causes for the deviation may be determined based on the comparison. Alternatively or additionally, the comparison (and/or a determined root cause) may be used to determine whether a planned final position of the dental arch is achievable without corrective action. This may include checking a position of one or more of the teeth in each arch as well as the progress of the treatment plan, which may include additional parameters including occlusion, bite relation, arch expansion, etc. One or more corrective actions for the orthodontic treatment plan may be determined based on the one or more probable root causes. The determined clinical signs, probable root causes and/or corrective actions may be presented to the dental practitioner and/or patient for his or her consideration.

Some corrective actions may be modifications to the final treatment plan (e.g., to final teeth positions) and/or staging of the teeth positions in the treatment plan, if the treatment plan is a multi-stage treatment plan, that may be made automatically without any input from the dental practitioner. Staging may refer to the sequence of movements from current or initial teeth positions to new teeth positions. Staging may include determining which tooth movements will be performed at different phases of treatment. Other corrective actions may be modifications to the treatment plan that are made after approval from the dental practitioner. Other corrective actions may require one or more actions or operations to be performed by the dental practitioner.

The methods and apparatuses described herein may notify a dental practitioner of progress deviation from an orthodontic treatment plan and informs the dental practitioner of actions to perform to ensure that a planned treatment outcome is achieved and/or how to adjust the planned treatment outcome to a more achievable goal. This may improve treatment plan efficacy. Improvements in treatment plan efficacy are likely to result in increased patient satisfaction as well as reduced costs by reducing the number of consecutive refinements that are made to a treatment plan (and associated orders of additional aligners) during treatment.

Although the treatment plans described herein may refer to multi-stage treatment plans, in which tooth movement is divided between a plurality of sequentially-worn aligners, the methods and apparatuses may also apply to single stage orthodontic treatment plans that have a target end position. For example, aligner sensor data may be generated at the beginning of a single stage orthodontic treatment plan and/or during the treatment plan. If the sensor data shows that, for example, the forces acting on the teeth during the single stage treatment plan (e.g., when the appliance is being worn) are not as expected, then the target end position may be adjusted for the single stage treatment plan and/or one or more treatment parameters for reaching the target end position may be adjusted; for example, a new appliance may be generated. Accordingly, it should be understood that all discussion of multi-stage treatment plans herein also applied to single stage treatment plans with target end positions and/or conditions unless otherwise specified.

Furthermore, described herein are appliances including in particular orthodontic aligners. The methods and apparatuses described herein are not limited to the operation of aligners. As used herein, an aligner may be an orthodontic appliance that is used to reposition teeth. Other appliance may include sensors, as described herein, and may therefore be used with the methods and apparatuses described herein, including, for example, palatal expanders, jaw repositioning appliances, and the like, including but not limited to brackets and wires, retainers, or functional appliances.

In general, an orthodontic appliance may include one or more sensors configured to obtain sensor data; these sensors may include those that are indicative of patient compliance (e.g., whether the patient is wearing the appliance), although the methods and apparatuses described herein are not limited or specific to compliance monitoring. The appliance can include one or more processors operably coupled to the sensor(s) and configured to process the sensor data.

Any of the methods and apparatuses described herein may be used to test and modify an ongoing orthodontic treatment plan. For example, described herein are methods of modifying an orthodontic treatment plan. These methods may include: receiving sensor data from one or more sensors of an orthodontic appliance (the sensors may be part of the orthodontic appliance, and may be any of the sensors described herein); determining tooth movement based on the sensor data; comparing the determined tooth movement to the treatment plan; and modifying the treatment plan if the determined tooth movement does not match the treatment plan.

For example, receiving sensor data may comprise receiving the sensor data in a processor that is on the orthodontic appliance, or alternatively separate from the appliance. The appliance may include communication circuitry for communicating (e.g., wirelessly and/or directly) with a processor such as a remote processor, such as a smartphone, tablet or other computing device. In some variations, for example, when the sensors are configured to detect force or pressure between the teeth and the appliance, receiving sensor data comprises receiving measurement of force applied to one or more teeth by the appliance. Receiving sensor data may comprise receiving measurements of torque on one or more teeth by the appliance. Thus, receiving sensor data comprises receiving force sensor data. The force sensor data may be any appropriate type of force data. For example, receiving force data may comprise resistive force measurements, magnetic force measurements, pressure measurements, or strain measurements.

In any of these methods, the tooth movement may be determined from the sensor data by identifying a direction of movement of one or more teeth based on the sensor data. For example, the tooth movement may be determined by determining the force mapping of between the appliance and the patient's teeth. The magnitude and direction of the force acting on the tooth may be detected; the sensor may be in a known location and therefore the tooth being acted on may be known, as well as the force vector. In some variations a digital model of the patient's teeth may be used to project or estimate the tooth movements.

The step of determining tooth movement may comprise identifying a rotation of one or more tooth based on the sensor data. Rotation of one or more tooth may be determined from the sensor data directly (e.g., measuring torque) and/or in combination with a model of the teeth (e.g., a digital model).

Any of the steps of determining tooth movement may be performed in a processor, such as a remote processor or a processor on the appliance; the processor may also include information about the appliance, such as what stage in the treatment it is, as well as the treatment plan itself (including key frames for the treatment plan, indicating which teeth are subjected to what forces/movements during each stage, etc.); and/or a model of the patient's teeth, including models of the patient's intended tooth position for each treatment stage.

In any of the methods described herein, comparing the determined tooth movement to the treatment plan may comprise comparing the determined tooth movement with an expected tooth movement from the treatment plan. The expected tooth movement from the treatment plan may correspond to an expected tooth movement from a stage of the treatment plan corresponding to the orthodontic appliance. The result of such a comparison may result in modifying the treatment plan. For example, if the comparison show a close match between the expected tooth movement (or tooth position/rotation) and the sensed force (or position/rotation derived from the sensed force), e.g., within a predetermined position (such as +/−%2%, 4%, 5%, 7%, 10%, 12%, 15%, 17%, 20%, etc.), for all or a majority of the teeth (or preselected specified teeth), then the treatment plan may be left the same. If the comparison shows a disparity between the sensed forces (or position/movement) and the expected values greater than this predetermined amount (e.g., +/−%2%, 4%, 5%, 7%, 10%, 12%, 15%, 17%, 20%, etc.), for all or a majority of the teeth (or preselected specified teeth), then the treatment plan may be modified, based on the sensed force and/or the comparison to the expected values. For example, if the forces applied by the appliance are below the predetermined amount (e.g., threshold) then the treatment plan may be accelerated, as increased forces may be applied to the teeth; the next stage may be worn, or one or more stages may be skipped. If the forces applied by the appliance are above the predetermined amount, then the treatment plan may be modified. For example, modifying the treatment plan may comprise adding one or more stages to the treatment plan based on the determined movement. Modifying the treatment plan may comprise replacing one or more stages with one or more new stages based on the movement of the determined movement. In some variations, modifying the treatment plan may comprise modifying a final position of the teeth in the treatment plan. Modifying the treatment plan may comprise providing instructions (e.g., to the dental practitioner) to modify one or more of the patient's teeth, for example, by interproximal reduction, tooth extraction, application of additional attachments to the appliance, etc.

In general, the treatment plan is compared to the sensor data. This comparison may be simplified by converting the sensor data to predicted tooth positions or movements so that they can be directly compared to the treatment plan, which in some variations is stored as a tooth movements, positions, or the like. See, e.g., U.S. Pat. No. 8,038,444B2 (describing "key frames" for forming a treatment plan). Alternatively or additionally, in some variations of the methods described herein, the processor may estimate or determined expected values from the treatment plan in terms of sensed parameters (e.g., force, pressure, etc.) for comparison with the sensor data.

For example a method of modifying an orthodontic treatment plan may include: receiving sensor data from one or more sensors of an orthodontic appliance; determining an expected value or a range of expected values for the one or more sensors from the orthodontic treatment plan; comparing the determined expected value(s) to the sensor data for each of the one or more sensors; and modifying the treatment plan if the sensor data does not match the determined expected value(s). As already mentioned, receiving sensor data may comprise receiving the sensor data in a processor that is in or on the orthodontic appliance, or that is remote to the orthodontic appliance. Receiving sensor data may comprise receiving measurement of force applied to one or more teeth by the appliance. Receiving sensor data may comprise receiving measurements of torque on one or more teeth by the appliance. Receiving sensor data may comprise receiving force sensor data (e.g., resistive force measurements, magnetic force measurements, pressure measurements, or strain measurements).

Thus, as mentioned above, determining the expected value or a range of expected values for the one or more sensors may comprise calculating the expected value or range of expected values from a stage of the treatment plan corresponding to the orthodontic appliance. This may generally include mapping or otherwise converting the treatment plan stages into values for comparison with the values received from or adapted from the sensors (e.g., the sensor data). For example, determining the expected value or a range of expected values for the one or more sensors may comprise calculating a force applied to the teeth at a location equivalent to a location of each of the one or more sensors on the orthodontic appliance when the one or more sensors are configured to detect force.

As described above, based on the comparison between the sensed data (e.g., force, pressure, etc.) and the treatment plan (e.g., expected values), the treatment plan may be modified. For example, modifying the treatment plan may comprise adding one or more stages to the treatment plan, replacing one or more stages with one or more new stages, modifying a final position of the teeth in the treatment plan, and/or providing instructions to modify one or more of the patient's teeth.

These method may be performed at any of the stages of the treatment plan. In general, the treatment plan may include a plurality of steps (stages) and an appliance may be worn for an indicated amount of time (e.g., days, weeks, etc.) at each stage. In some variations, each stage may include an appliance with one or more sensors that may provide sensor data for checking in and correcting/modifying the treatment plan; alternatively or additionally, at least one appliance in the treatment plan may be used for this feedback. For example, the feedback methods descried herein (e.g., comparing the treatment plan to sensor data from the appliance when worn and adjusting the treatment plan accordingly) may be performed at every stage; at every other stage, at every third stage, etc., at the half-way mark through the treatment plan, or at any other schedule.

Also described herein are apparatuses (including systems, software/firmware, etc. and devices) that are configured to allow feedback (e.g., closed or semi-closed loop feedback) to modify the treatment plan based on a comparison with sensed data (e.g., force, pressure, etc.) and a current treatment plan. Any of these apparatuses, e.g., systems, may include one or more appliances including one or more sensors and a processor that is configured (e.g., by including software/firmware, etc.) to perform the methods described above. For example, an orthodontic system for treating a patients teeth based on a treatment plan may include: at least one orthodontic appliance, wherein the at least one orthodontic appliance corresponds to a treatment stage in the treatment plan, further wherein the at least one orthodontic appliance comprises one or more sensors; and a processor in communication with the one or more sensors, wherein the processor is configured to: receive sensor data from the one or more sensors; determine tooth movement based on the sensor data; compare the determined tooth movement to the treatment plan; and modify the treatment plan if the determined tooth movement does not match the treatment plan.

In another example, an orthodontic system for treating a patients teeth based on a treatment plan may include: at least one orthodontic appliance, wherein the at least one orthodontic appliance corresponds to a treatment stage in the treatment plan, further wherein the at least one orthodontic appliance comprises one or more sensors; and a processor in communication with the one or more sensors, wherein the processor is configured to: receive sensor data from one or more sensors of an orthodontic appliance; determine an expected value or a range of expected values for the one or more sensors from the orthodontic treatment plan; compare the determined expected value(s) to the sensor data for each of the one or more sensors; and modify the treatment plan if the sensor data does not match the determined expected value(s).

The at least one orthodontic appliance may include a transmitter to transmit sensor data from the one or more sensors to the processor, wherein the processor is remote to the appliance. Alternatively or additionally, the processor may be on the at least one orthodontic appliance. The at least one orthodontic appliance may comprise a series of orthodontic appliances.

In general, a dental or orthodontic appliance may be a shell appliance, e.g., a shell comprising a plurality of teeth receiving cavities; one or more sensors operably coupled to the appliance shell and configured to generate sensor data indicative of appliance usage by a patient; and a processor operably coupled to the one or more sensors and configured to process the sensor data so as to determine whether the intraoral appliance is being worn on the patient's teeth.

The methods and apparatuses described herein may generally be used with or as part of any monitoring devices for monitoring an orthodontic appliance. For example, described herein are Electronic Compliance Indicator (ECI) apparatuses that may be configured to record sensor data from subjects (e.g., patients) wearing or intended/intending to wear an orthodontic aligner such as a shell aligner. However, it should be understood that these methods and apparatuses are not limited to just monitoring compliance and operation on compliance data, but may be used for any type of data, and these monitoring apparatuses (including ECIs) may also be generically referred to as data loggers or embedded data loggers. Thus, in any of the description and examples provided herein, unless the context makes it clear otherwise, when an "ECI" apparatus is described, the apparatus may not be limited to compliance monitoring. Thus, for any of the description, examples, methods and apparatuses described herein, the term "ECI" should be understood to be more broadly referred to as a monitoring apparatus (MA) or performance monitoring apparatus (PMA), and not just an ECI.

For example, in any of these apparatuses, the data may be stored in physical memory on the monitoring apparatus (e.g., the ECI) and may be retrieved by another device in communication with the monitoring apparatus. Retrieval may be done wirelessly, e.g., using near-field communication (NFC) and/or Bluetooth (BLE) technologies to use a smartphone or other hand-held device to retrieve the data. Specifically described herein are monitoring apparatuses (including ECI apparatuses) and orthodontic aligners using them that include temperature and capacitive sensors, a CPU, a NFC communication module, an NFC antenna, a PCB and battery.

An appliance configured to monitor usage of an intraoral appliance may include a housing enclosing a power source and monitoring circuitry, the monitoring circuitry comprising a processor, a memory, and one or more sensors; optionally, the appliance may include a removable mechanical activation interrupt (e.g., 315 in FIG. 3A) between the power source and the processor, wherein the mechanical activation interrupt has a first position that breaks a connection between the power source and the monitoring circuitry so that no current flows between the power source and the monitoring circuitry and a second position in which there is an electrical connection between the monitoring circuitry and the power source; and an elastomeric overmold encapsulating the housing.

In general, the housing may have a maximum diameter of 2 cm or less, 1.5 cm or less, 1.0 cm or less, 0.9 cm or less, 0.8 cm or less, 0.7 cm or less, 0.6 cm or less, etc.). The housing enclosing the monitoring processor may generally be thin (e.g., 1.0 cm or less, 0.9 cm or less, 0.8 cm or less, 0.7 cm or less, 0.6 cm or less, 0.5 cm or less, 0.4 cm or less, etc.). In any of these apparatuses, the monitoring circuitry may be configured for a wired connection, e.g., may include a plurality of data electrodes external to the housing but encapsulated by the elastic overmold. The apparatus may configured to be connect to a plurality of metallic/conductive leads that pierce the (e.g., self-healing) overmold material to contact the otherwise covered contacts.

In any of the methods and apparatuses described herein, the orthodontic appliances may include monitoring components in addition to the sensors for receiving/storing/processing the sensor data. For example, the apparatus may include monitoring components within one or more housings (e.g., configured as an electronic compliance indicator apparatus); the monitoring components are typically configured to monitor sensors of the intraoral appliance and may provide output via a removable wired connection and/or a wireless connection. Monitoring components may include: a housing enclosing a power source and monitoring circuitry, the monitoring circuitry comprising a processor, a memory, and one or more sensors or connections to one or more sensors; a self-healing elastomeric overmold encapsulating the housing; a plurality of data electrodes external to the housing but encapsulated by the elastic overmold; and an attachment configured to secure the monitoring apparatus to an orthodontic appliance. The apparatus may include the orthodontic appliance (e.g., a shell aligner). Any appropriate self-healing material may be used, including an electrically insulating polymeric material.

The apparatuses and methods described herein may include near field communication (NFC) circuitry, configured for NFC-to-NFC communication, etc. Any of the methods and apparatuses described herein may also or additionally be used with other types of wireless communication modes, including, without limitation, Wi-Fi, radio (RF, UHF, etc.), infrared (IR), microwave, Bluetooth (including Bluetooth low energy or BLE), magnetic field induction (including NFC), Wimax, Zigbee, ultrasound, etc.

The orthodontic appliance may comprise an intraoral appliance shaped to receive the patient's teeth and one or more sensors, configured as a plurality of electrodes. The electrodes are positioned to make electrical contact with the patient's intraoral cavity when the intraoral appliance is worn by the patient. The appliance further comprises one or more processors configured to use the electrodes to measure an electrical impedance. The processor uses the measured electrical impedance to determine a physiological characteristic of the patient.

The apparatus may comprises an intraoral appliance shaped to receive the patient's teeth and includes a transmitter and a receiver. The appliance may further comprise one or more processors configured to cause the transmitter to emit a signal within the patient's intraoral cavity; measure a signal returning from the patient's intraoral cavity in response to the emitted signal using the receiver.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7A and 7B illustrate an example of a monitoring device with a deflectable structure.

FIG. 7C shows an example of a monitoring device with a deflectable structure.

FIG. 9 illustrates an example of a monitoring system for detecting proximity between the patient's jaws.

FIG. 10A shows an example of a monitoring device utilizing optical sensing.

FIG. 10B illustrates an example of a monitoring device using optical sensing.

FIG. 10C illustrates an example of a monitoring device using optical sensing.

FIG. 14A illustrates an example of a monitoring device using a plurality of magnets.

FIG. 14B is a cross-sectional view of the device of FIG. 14A.

FIG. 15 illustrates an example of a monitoring device configured to measure force and/or pressure between an intraoral appliance and the patient's teeth.

FIG. 17B illustrates an example of a monitoring device including a gas flow sensor.

FIG. 17C shows an example of a monitoring device including a gas flow sensor.

FIG. 18 illustrates an example of a monitoring device using motion sensing.

FIG. 19 illustrates an example of a method for monitoring usage of an intraoral appliance.

DETAILED DESCRIPTION

Described herein are methods and apparatuses for closed or semi-closed loop modification of an orthodontic treatment plan. In general, these methods and apparatuses compare sensor information from one or more sensors on an orthodontic appliance that forms part of a treatment plan, such as an aligner, with an ongoing treatment plan. The sensor data and/or the treatment plan may be adjusted so that comparison may be made directly or indirectly. Based on the comparison between the sensor data and the treatment plan, the treatment plan may be modified. Modifications may include advancing to the next stage (e.g., ahead of the treatment plan schedule) and/or skipping a stage, creating a new stage or stages, changing the final stage, etc. This is illustrated in FIG. 1A.

Figure 1A:
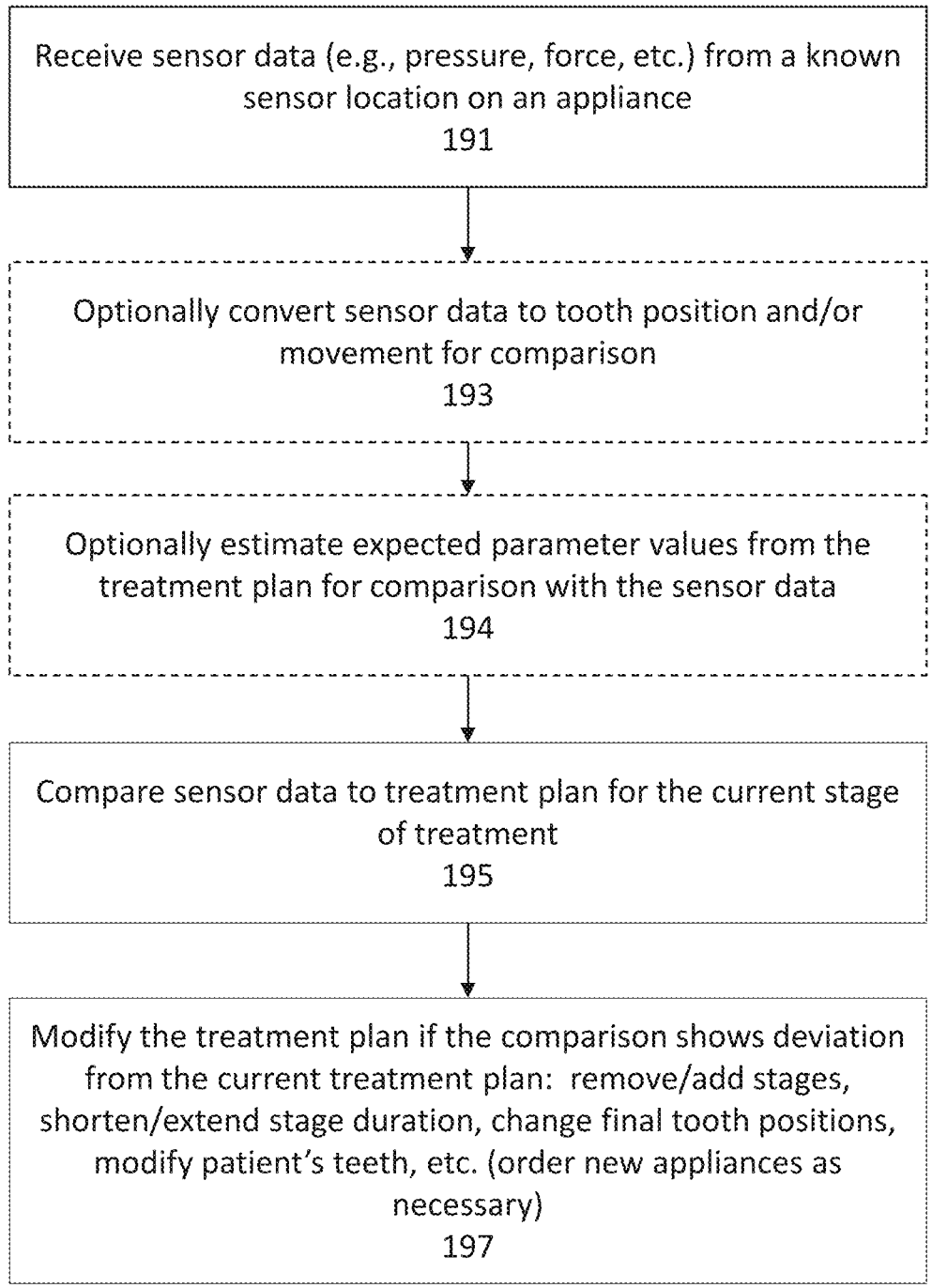
FIG. 1A is a schematic of a method for closed-loop (or semi closed-loop) modification of a treatment plan.

In FIG. 1A, a processor typically receives sensor data (e.g., pressure, force, etc.) from a known sensor location on an appliance 191. The processor may be on the appliance or separate (e.g., remote) from the appliance. The processor may already have or may also receive the treatment plan, and an indication of what stage of the treatment the appliance corresponds to. The processor may also include a digital model of the patient's teeth. In some variations the sensor data is encoded or marked to indicate the identity (e.g., location, type, etc.) of the sensor from which it originated.

Either or both the sensor data may be modified for comparison with the treatment plan and/or the treatment plan may be analyzed to determine an expected value of the teeth, so that the sensor data corresponding to a particular stage in the treatment may be compared to the treatment plan. For example, optionally the processor may convert sensor data to tooth position and/or movement for comparison with the treatment plan 193, and/or the processor may estimate expected parameter values from the treatment plan for comparison with the sensor data 194. The processor may then compare the sensor data to the treatment plan for the current stage of treatment 195, and, based on the results, the treatment plan may be modified. For example, the treatment plan may be modified if the comparison shows deviation from the current treatment plan 197. Modification may include one or more of: remove/add stages, shorten/extend stage duration, change final tooth positions, modify patient's teeth, etc. (order new appliances as necessary).

For example, the sensor data may be force or pressure sensor data and may correspond to the force applied by the appliance to the teeth. Tooth position and/or movement information may be estimated from the force data, and compared with the tooth position and/or movement from the corresponding stage of the treatment plan; e.g., the stage corresponding to the orthodontic appliance. Alternatively or additionally, expected values that may be compared with the sensor data may be estimated from the treatment plan, and compared to the sensor data. The expected value may correspond to expected values that can be directly compared with the sensor data (e.g., force one the teeth, pressure on the teeth, etc.). A model, e.g., a digital model, of the patient's teeth may be used in any of these techniques.

Figure 1B:
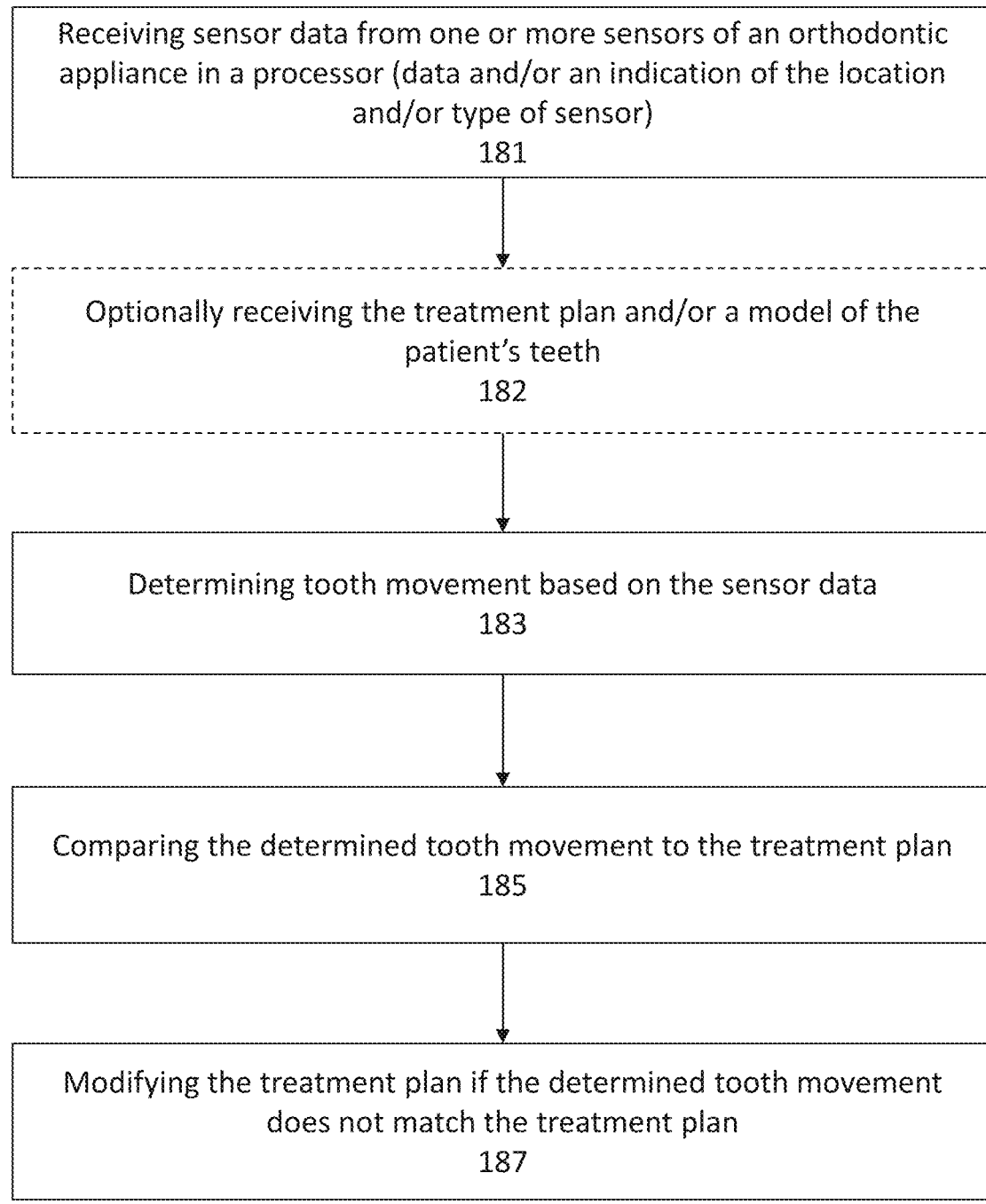
FIGS. 1B and 1C are exemplary schematics for closed-loop (or semi closed loop) modification of a treatment plan.
Figure 1C:
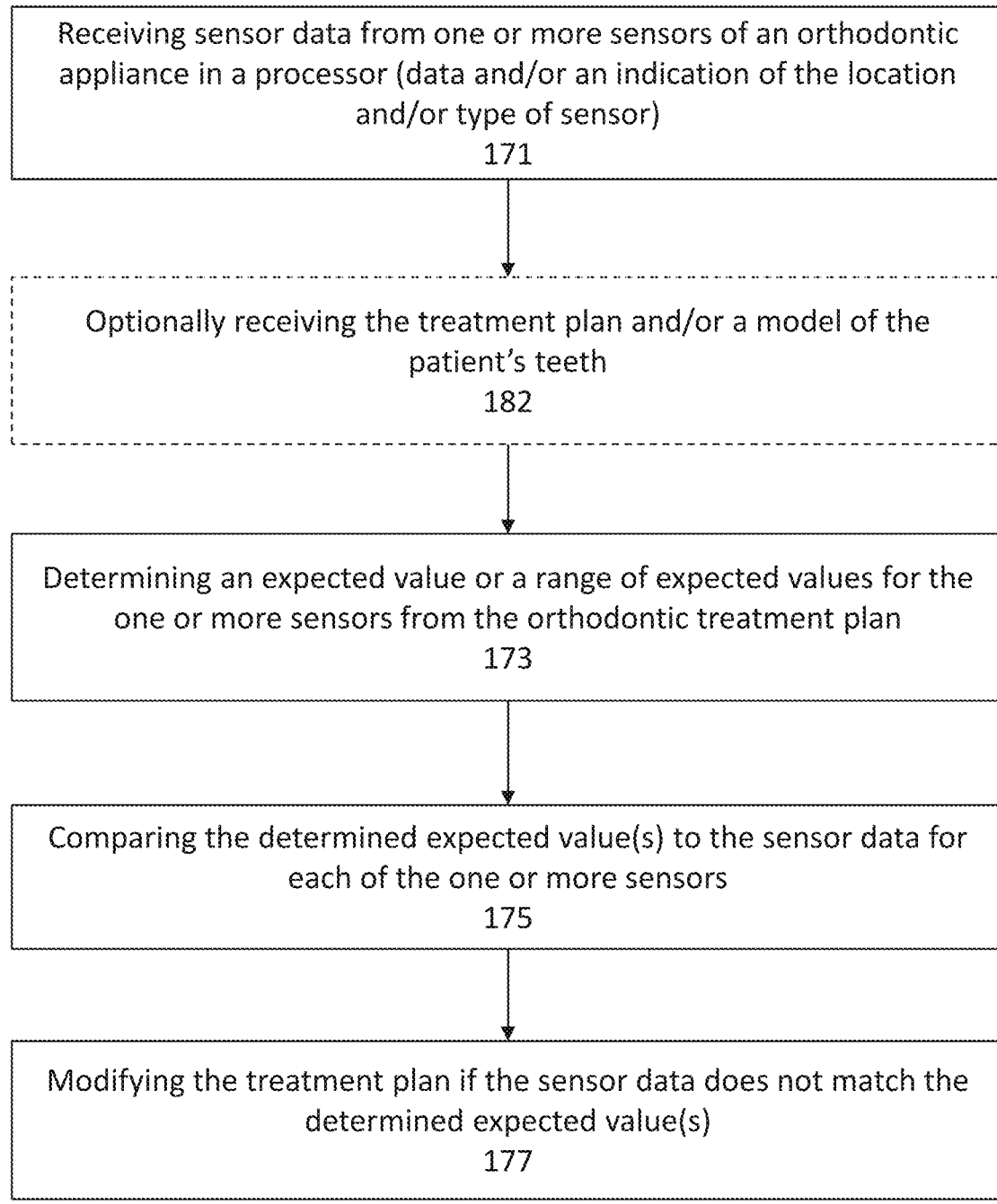

FIGS. 1B and 1C show flowcharts illustrating methods of methods of modifying an orthodontic treatment plan. In FIG. 1B, the method shown includes: receiving sensor data from one or more sensors of an orthodontic appliance 181; determining tooth movement based on the sensor data 183; comparing the determined tooth movement to the treatment plan 185; and modifying the treatment plan if the determined tooth movement does not match the treatment plan 187.

In FIG. 1C, the method of modifying an orthodontic treatment plan includes: receiving sensor data from one or more sensors of an orthodontic appliance 171; determining an expected value or a range of expected values for the one or more sensors from the orthodontic treatment plan 173; comparing the determined expected value(s) to the sensor data for each of the one or more sensors 175; and modifying the treatment plan if the sensor data does not match the determined expected value(s) 177. Optionally, these methods may include receiving the treatment plan and/or a model of the patient's teeth 182.

Thus, the methods described herein compare the treatment plan, which typically includes a plurality of stages, in which for each stage there is a different appliance to be worn. For each appliance there is a corresponding expected set of forces acting on the oral cavity (e.g., teeth, palate, etc.) to reconfigured the oral cavity in some incremental manner. The sensors described herein (a number of example of which are provided below) may generate data that can be compared to the treatment plan. If there is insufficient match between the treatment plans' expected values for the tooth position, movement and/or forces acting on the oral cavity and the actual sensed data (which can be forces, position, etc.), the treatment plan may not be working and may be modified in a manner that is informed by the comparison. For example, if an aligner in the treatment plan series is expected to produce rotation of a premolar tooth and a sensor in an aligner in a position corresponding to this premolar does not register rotation (e.g., based on the pressure or force applied to aligner when worn), then the aligner may be failing to rotate the tooth as desired. The information from the sensor may be analyzed to determine the underlying cause. Further, the treatment may be optimized by, e.g., generating or requesting generation of a new subsequent stage that more directly addresses the tooth rotation, e.g., by applying additional force to the premolar to rotate it as desired, adding an attachment, removing another attachment, etc. Thus, the treatment plan may be modified during execution of the treatment plan based on sensor feedback from one or more sensors integrated into the device worn by the patient. In some variations, the appliance may include multiple different sensors in different areas depending on which teeth or movements are to be tracked. In particular, for a specific treatment plan, the apparatus may include sensors that are positioned on the appliance near the teeth to be moved during that stage. In general, the methods and apparatuses described herein may analyze the force systems of the appliance at each stage by, e.g., determining the magnitude and direction of the forces applied to one or more teeth. This information may be used to calculate tooth movement (expected tooth movement) and/or compared to the treatment plan. For example, the apparatus may determine if the tooth is rotating, tipping, translating or otherwise moving in a particular direction, and may check this movement over time against the treatment plan. This information may then be used to determine when to change an appliance (e.g., aligner) or the overall treatment plan. For example, if a treatment plan fails, e.g., by failing to result in the necessary tooth movement, particularly early in treatment, the method or apparatus may conclude that certain movements are not achievable. The treatment plan may be modified by changing the sequence of appliances, adding an appliance, recommending modification of the teeth (e.g., by removing teeth/opening spaces, interproximal reduction, etc.), attaching/removing attachments for coupling to the appliance, or the like. As will be described in greater detail below, any of these methods may include any appropriate sensor. Force or pressure sensors may be particularly helpful, however position sensors may also be used. Multiple sensors, in multiple locations, may be used. When more than one appliance in the treatment plan includes sensors, the sensors may be in the same position for different appliance within the sequence of the treatment plan, or they may be in different locations.

When the methods and apparatuses described herein modify the treatment plan following comparison between sensed data and the current treatment plan, the modified treatment plan may include new appliances. In some variations, these new appliances may be fabricated (e.g., on demand), or they may be selected from a preexisting pool of appliances.

Thus, the methods and apparatuses described herein may provide closed loop (or semi closed loop, in which a user/dental professional may be included in the modification) for modification of a treatment plan. These methods and apparatuses may determine if the aligner done its work, when the best time for replacement of the aligner is, which is the next best aligner from a group of pre-made aligners or if there is a need to make a new aligner, and/or if there is a need to change the treatment plan or the stages.

Figure 1D:
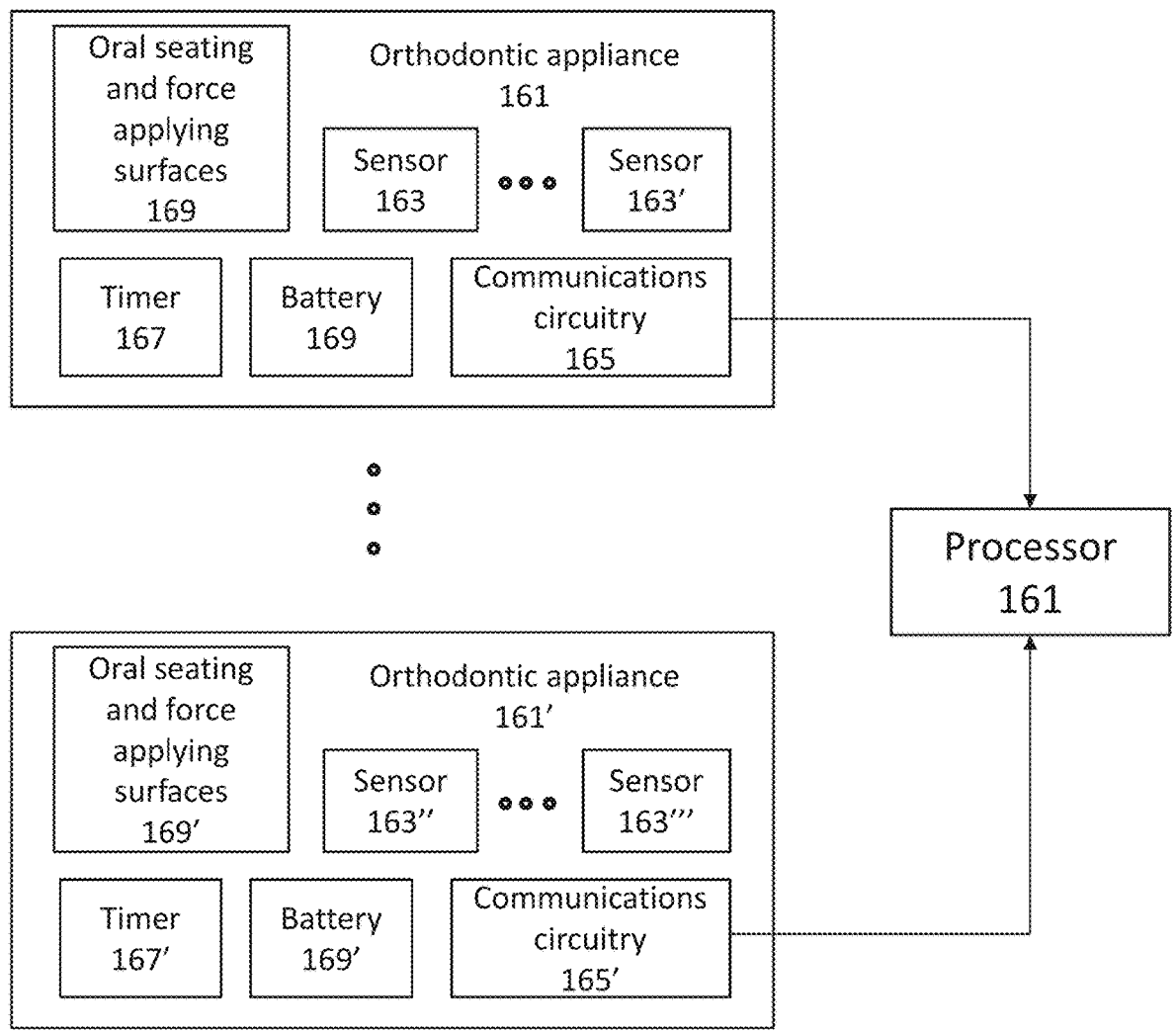
FIG. 1D is an example of a system for closed-loop (or semi-closed loop) modification of a treatment plan.

FIG. 1D illustrates a schematic of an apparatus (configured as a system) configured to treat a patients teeth based on a treatment plan, and automatically or semi-automatically modify the treatment plan as it is being used. In FIG. 1D, the system includes at least one orthodontic appliance 161, 161'. In some variations only a single orthodontic appliance is included (in some variations multiple orthodontic appliances are included, but only one or a subset of them include sensors). The orthodontic appliance may be, e.g., an aligner. Each orthodontic appliance corresponds to a treatment stage, as will be described by example with reference to FIGS. 2A-2D, below, and includes a body with a seating surface configured to seat in the oral cavity 169, 169'. The seating surface may be, for example, channel or chamber for seating onto the teeth. The appliance is also configured to apply force against the oral cavity (e.g., teeth); at least a portion of the seating surface(s) may be configured to apply force against the oral cavity. As shown schematically in FIG. 1D, the appliance may include a sensor 163 or a plurality of sensors 163'. Examples of sensors are described herein, including ways in which they may engage with or be formed in/on the orthodontic appliance. In FIG. 1D, the orthodontic appliance may also include circuitry to support the sensor(s), sensor data receiving circuitry, circuitry for amplifying/smoothing/filtering, etc. the sensor signal(s), circuitry for storing (e.g., memory) and/or transmitting the sensor signals (e.g., communications circuitry 165), as well as a power supply (e.g., battery 169), timer 167, etc. The appliance may also include one or more processors built-into the appliance or remotely accessible. In FIG. 1D, the processor 161 is shown to be remote to the appliance, and may be accessed by the appliance, e.g., wirelessly via the communications circuitry 165. In this example, the remote processor may be part of a smartphone, tablet, or other computing device, including wearable or hand-held devices. In FIG. 1D, a plurality of different orthodontic appliances are shown, all of which may communicate with the processor 161 (which may be referred to as feedback processor). The processor, in general, may already have (in a processor-accessible memory) or may receive, the treatment plan. The processor may be configured to receive sensor data from the one or more sensors. This data may be manipulated by the processor, including filtering the data. The data may be associated with a particular sensor location on the particular appliance (e.g., corresponding to a particular stage in the treatment plan). The sensor data may be taken, stored, and/or transmitted only when the device is being worn by the patient. For example, the appliance may be configured to record sensor data only when the device is determined to be inserted into the oral cavity, which may be detected by the same sensor(s).

In some variations, the processor may be configured to determine tooth movement based on the sensor data. For example, if the sensor data corresponds to force on the appliance, the tooth movement may be determined by predicting, based on the locations of the force sensor, the direction and magnitude of the force, and the model of the patient's teeth, how much the tooth will move under this force. The predicted tooth movement may be compared to the tooth movement expected from the treatment plan. In some variations, the force (magnitude and direction) may be directly compared to the treatment plan for the particular stage corresponding to the appliance from which the sensor data was collected, and/or the treatment plan information may be translated (by the processor) into a corresponding expected value for comparison with the sensor data. As described above, as a result of the comparison, the treatment plan may be modified if the determined tooth movement does not match the treatment plan. For example, the apparatus (such as the system shown in FIG. 1D, may include an output from the processor indicating that the treatment plan should be modified, and indicating how to modify it, including, e.g., ordering one or more new appliances to be worn, modifying the end point (final position) of the treatment plan, modifying the patient's dentition (e.g., removing a tooth, interproximal reduction, etc.), indicating when the next appliance in the series should be worn and/or what the next appliance from the prefabricated series should be worn, etc. Thus, the processor may be configured to output a report to the user (e.g., dental professional), and/or patient. In semi closed-loop systems, the modification of the treatment plan may then be enacted by the user or patient. The output may be any appropriate output, including text (e.g., SMS), hard-copy, video display, etc.

In general, any appropriate sensor may be used as part of these systems. For example a system may include one more embedded sensors in the aligner. Examples of sensor may detect stress in the aligner, force applied to the teeth, the direction of the force, and/or the teeth movement and rotation. Described below are examples of apparatuses including sensors that may be used as described herein.

The apparatuses described herein may record sensor data from a subject wearing one or more dental appliances, such as dental/orthodontic aligners, including shell aligners. Data recorded by the appliance may be stored in physical memory on the appliance and may be retrieved by another device. In particular, the data described may be retrieved by a hand held electronics communication device such as a smartphone, tablet, or the like. The handheld electronic device may include a user interface to augment communication between the appliance and the device, and may provide feedback to the user (e.g., dental practitioner, such as a technician, physician, dentist, orthodontist, or other medical/dental practitioner) and/or patient. Once transmitted to the handheld device, the data may be processed (or further processed) and/or passed on to a remote processor, memory and/or server.

The apparatuses described herein may use both NFC and/or BLE communication to transmit data between an ECI and a handheld electronic device (e.g., smartphone). Using NFC and BLE technologies may allow a smartphone to retrieve the data even from a very small ECI that includes only a small antenna, with a reasonably high accuracy and low power.

The apparatuses and methods described herein for monitoring treatment with removable intraoral appliances may generate sensor data related to usage of an intraoral appliance. The sensor data can be processed and analyzed to determine whether the patient is wearing the appliance in accordance with a prescribed treatment plan. Advantageously, the apparatuses and methods described herein provide an integrated electronic sensing and logging system capable of generating more reliable and accurate patient compliance data, which may be used by the treating practitioner to track patient behavior and improve treatment efficacy. Additionally, the monitoring apparatuses described herein may provide high value sensing data useful for appliance design. In some embodiments, the sensing data provided by the monitoring apparatuses described herein may be used as feedback to modify parameters of an ongoing orthodontic treatment, also known as adaptive closed-loop treatment planning.

The apparatuses described herein may detect when the device is worn on a subject's tooth/teeth using any appropriate method, including one or more of those described herein. For example, an apparatuses for monitoring usage of an intraoral appliance may include one or more deflectable structures formed with or coupled to the intraoral appliance. The deflectable structure(s) can be shaped to be deflected when the intraoral appliance is worn on a patient's teeth. The device can comprise a sensor configured to generate sensor data indicative of deflection of the deflectable structure(s). Optionally, the device can comprise a processor operably coupled to the sensor and configured to process the sensor data so as to determine whether the intraoral appliance is being worn. The amount and/or direction of deflection may be determined and correlated to force acting on the appliance.

The intraoral appliance may comprise an appliance shell including a plurality of teeth receiving cavities. The deflectable structure(s) can be located near a tooth receiving cavity of the plurality of teeth receiving cavities so as to be deflected outward when a tooth is positioned within the tooth receiving cavity. The deflectable structure(s) can be formed in a wall of the tooth receiving cavity. The deflectable structure(s) can be deflected outward by at least 25 μm when the tooth is positioned within the tooth receiving cavity.

The deflectable structure(s) may comprise a deflected state when the intraoral appliance is being worn and a resting state when the intraoral appliance is not being worn, and the deflectable structure(s) interact with the sensor when in the deflected state. The sensor can comprise a mechanical switch and the deflectable structure(s) can engage the mechanical switch when in the deflected state. The sensor can comprise an optical switch and the deflectable structure(s) can activate the optical switch when in the deflected state.

The deflectable structure(s) may comprise a cantilever, dimple, concavity, flap, protrusion, or pop-out structure.

The apparatuses may further comprise a communication unit operably coupled to the sensor and configured to transmit one or more of the sensor data or the processed sensor data to a remote device. The sensor may be integrated with the intraoral appliance or coupled to a tooth. The processor may be integrated with the intraoral appliance or coupled to a tooth. Alternatively or additionally, the processor may be located external to the patient's intraoral cavity.

Any of the devices for monitoring usage of an intraoral appliance may comprise an appliance shell comprising a plurality of teeth receiving cavities and one or more proximity sensors operably coupled to the appliance shell and configured to generate sensor data when in proximity with intraoral tissue. The device can comprise a processor operably coupled to the one or more proximity sensors and configured to process the sensor data so as to determine whether the intraoral appliance is being worn on a patient's teeth.

The one or more proximity sensors may comprise one or more touch sensors (similarly the touch sensors described herein may be referred to as proximity sensors and/or proximity/touch sensors). The one or more touch sensors can comprise at least one capacitive touch sensor activated by charges associated with one or more of enamel, gingiva, oral mucosa, saliva, cheeks, lips, or tongue. The one or more touch sensors can comprise at least one capacitive touch sensor activate by positive charges associated with plaque or bacteria on the patient's teeth. The processor may optionally be configured to process the sensor data so as to determine an amount of bacteria on the patient's teeth. The one or more touch sensors can comprise at least one resistive touch sensor.

The one or more touch sensors may comprise at least one capacitive touch sensor configured to use one or more of enamel, gingiva, oral mucosa, saliva, cheeks, lips, or tongue as a ground electrode.

The one or more proximity sensors may comprise one or more of: a capacitive sensor, an eddy-current sensor, a magnetic sensor, an optical sensor, a photoelectric sensor, an ultrasonic sensor, a Hall Effect sensor, an infrared touch sensor, or a surface acoustic wave (SAW) touch sensor. The one or more proximity sensors may be configured to generate sensing data when in proximity to one or more of the patient's enamel, gingiva, oral mucosa, cheeks, lips, or tongue. The one or more proximity sensors may be integrated with the intraoral appliance, coupled to a tooth, or a combination thereof.

The processor may be integrated with the intraoral appliance or coupled to a tooth.

An apparatuses for monitoring usage of an intraoral appliance may include an appliance shell comprising a plurality of teeth receiving cavities and one or more vibration sensors operably coupled to the appliance shell and configured to generate sensor data of intraoral vibration patterns. The device can also comprise a processor operably coupled to the one or more vibration sensors and configured to process the sensor data so as to determine whether the intraoral appliance is being worn on a patient's teeth. The one or more vibration sensors comprise one or more of: a MEMS microphone, an accelerometer, or a piezoelectric sensor. The intraoral vibration patterns may be associated with one or more of: vibrations transferred to the patient's teeth via the patient's jaw bone, teeth grinding, speech, mastication, breathing, or snoring. The processor may determine whether the intraoral appliance is being worn by comparing the intraoral vibration patterns to patient-specific intraoral vibration patterns. The one or more vibration sensors may be integrated with the intraoral appliance, coupled to a tooth, or a combination thereof. The processor is integrated with the intraoral appliance or coupled to a tooth.

The various embodiments described herein can be used in combination with various types of intraoral appliances worn in a patient's mouth. The intraoral appliance may be an orthodontic appliance, such as an aligner or wire-and-bracket appliance, used to reposition one or more of the patient's teeth to a desired arrangement, e.g., to correct a malocclusion. Alternatively or additionally, the intraoral appliance may be used to maintain one or more of the patient's teeth in a current arrangement, such as a retainer. Other examples of intraoral appliances suitable for use in conjunction with the embodiments herein include sleep apnea treatment devices (e.g., mandibular advancement devices or splints), night guards (e.g., for treating bruxism), mouth guards, and palatal expanders.

Figures 2A, 2B, 2C, 2D:
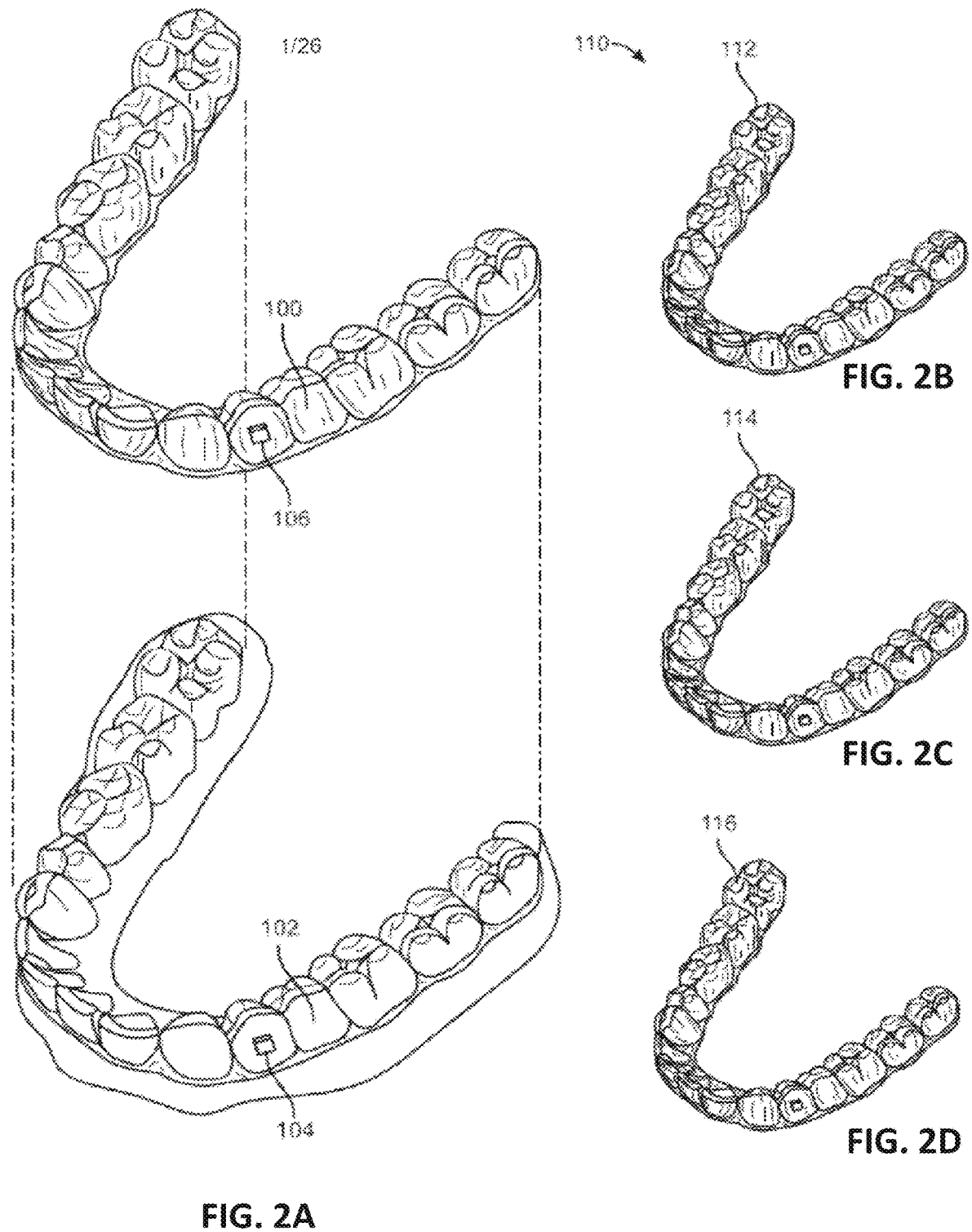
FIG. 2A illustrates an example of a tooth repositioning appliance.
FIGS. 2B-2D shows an example of a tooth repositioning system.

Appliances having teeth receiving cavities that receive and reposition teeth, e.g., via application of force due to appliance resiliency, are generally illustrated with regard to FIG. 2A. FIG. 2A illustrates an exemplary tooth repositioning appliance or aligner 100 that can be worn by a patient in order to achieve an incremental repositioning of individual teeth 102 in the jaw. The appliance can include a shell having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some embodiments, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the URL "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

FIGS. 2B-2D illustrate an example of a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

In some embodiments, orthodontic appliances, such as the appliance illustrated in FIG. 2A, impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space, and may comprise one or more of rotation or translation along one or more axes. Types of tooth movements include extrusion, intrusion, rotation, tipping, translation, and root movement, and combinations thereof, as discussed further herein. Tooth movement of the crown greater than the movement of the root can be referred to as tipping. Equivalent movement of the crown and root can be referred to as translation. Movement of the root greater than the crown can be referred to as root movement.

Figure 2E:
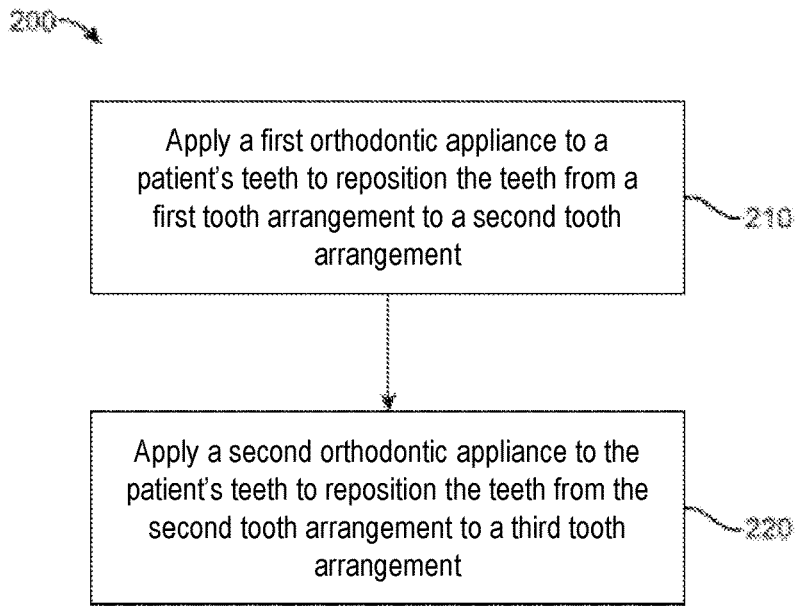
FIG. 2E illustrates a method of orthodontic treatment using a plurality of appliances.

FIG. 2E illustrates a method 200 of orthodontic treatment using a plurality of appliances, in accordance with embodiments. The method 200 can be practiced using any of the appliances or appliance sets described herein. In step 210, a first orthodontic appliance is applied to a patient's teeth in order to reposition the teeth from a first tooth arrangement to a second tooth arrangement. In step 220, a second orthodontic appliance is applied to the patient's teeth in order to reposition the teeth from the second tooth arrangement to a third tooth arrangement. The method 200 can be repeated as necessary using any suitable number and combination of sequential appliances in order to incrementally reposition the patient's teeth from an initial arrangement to a target arrangement. The appliances can be generated all at the same stage or time point, in sets or batches (e.g., at the beginning of one or more stages of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

An intraoral appliance can be operably coupled to a monitoring device (also referred to herein as an "electronic compliance indicator") configured to provide data related to appliance usage and/or patient compliance, such as data indicative of whether the appliance is being worn, the amount of time the appliance is worn, and/or interaction between the appliance and the intraoral cavity (e.g., contact between the appliance and intraoral tissues, force and/or pressure applied by the appliance to intraoral tissues). Alternatively or in combination, the monitoring device can be configured to provide data indicative of one or more characteristics of the patient's intraoral cavity or a portion thereof (e.g., teeth, gingiva, palate, lips, tongue, cheeks, saliva, airway), such as temperature, color, sound, vibration, motion, pH, conductivity, charge, resistance, capacitance, humidity, or gas flow. The characteristics of the patient's intraoral cavity can optionally be used to determine appliance usage and/or patient compliance, as discussed in greater detail herein.

The monitoring devices described herein can be designed for use in the patient's intraoral cavity. For example, the dimensions of a monitoring device may be limited in order to avoid patient discomfort and/or facilitate integration into an intraoral appliance as discussed below. In some embodiments, a monitoring device has a height or thickness less than or equal to about 1.5 mm, or less than or equal to about 2 mm. In some embodiments, a monitoring device has a length or width less than or equal to about 4 mm, or less than or equal to about 5 mm. The shape of the monitoring device can be varied as desired, e.g., circular, ellipsoidal, triangular, square, rectangular, etc. For instance, in some embodiments, a monitoring device can have a circular shape with a diameter less than or equal to about 5 mm.

A relatively thin and flexible monitoring device can be used to provide a larger surface area while reducing patient discomfort. In some embodiments, the monitoring devices herein are sized to conform to a surface of a tooth crown (e.g., a buccal, lingual, and/or occlusal surface of a tooth crown). For example, a monitoring device having dimensions of about 10 mm by about 5 mm can be used to cover a buccal surface of a molar crown. As another example, a monitoring device having dimensions of about 10 mm by about 20 mm can be used to cover the buccal, occlusal, and lingual surfaces of a tooth crown. A monitoring device can be in contact with a crown of a single tooth, or with crowns of a plurality of teeth, as desired.

The other properties of the monitoring device (e.g., volume, weight) can be designed in order to reduce patient discomfort. For instance, the weight of a monitoring device can be selected not to exceed a level that would exert undesirable forces on the underlying teeth.

Figure 3A:
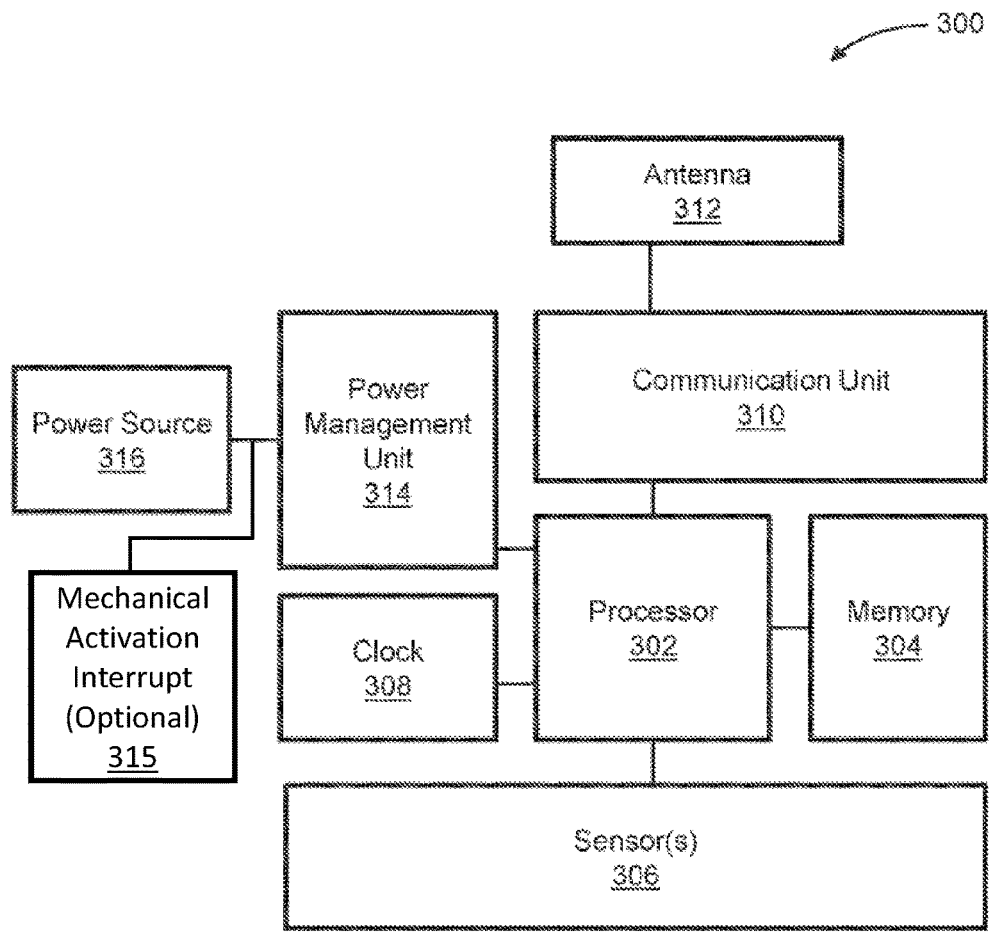
FIG. 3A schematically illustrates an example of a monitoring apparatus (shown as an ECI device).

FIG. 3A schematically illustrates a monitoring device 300 (e.g., an ECI). The monitoring device 300 can be used in combination with any embodiment of the systems and devices described herein, and the components of the monitoring device 300 are equally applicable to any other embodiment of the monitoring devices described herein. The monitoring device 300 can be implemented as an application-specific integrated circuit (ASIC) including one or more of the following components: a processor 302, a memory 304, one or more sensors 306, a clock 308, a communication unit 310, an antenna 312, a power management unit 314, or a power source 316. The processor 302 (e.g., a central processing unit (CPU), microprocessor, field programmable gate array (FPGA), logic or state machine circuit, etc.), also referred to herein as a controller, can be configured to perform the various methods described herein. The memory 304 encompasses various types of memory known to those of skill in the art, such as RAM (e.g., SRAM, DRAM), ROM (EPROM, PROM, MROM), or hybrid memory (e.g., flash, NVRAM, EEPROM), and the like. The memory 304 can be used to store instructions executable by the processor 302 to perform the methods provided herein. Additionally, the memory can be used to store sensor data obtained by the sensor(s) 306, as discussed in greater detail below.

The monitoring device 300 can include any number of sensors 306, such as one, two, three, four, five, or more sensors. In some embodiments, the use of multiple sensors provides redundancy to increase the accuracy and reliability of the resultant data. Some or all of the sensors 306 can be of the same type. Some or all of the sensors 306 can be of different types. Examples of sensor types suitable for use in the monitoring devices described herein include: touch or tactile sensors (e.g., capacitive, resistive), proximity sensors, audio sensors (e.g., microelectromechanical system (MEMS) microphones), color sensors (e.g., RGB color sensors), electromagnetic sensors (e.g., magnetic reed sensors, magnetometer), light sensors, force sensors (e.g., force-dependent resistive materials), pressure sensors, temperature sensors, motion sensors (e.g., accelerometers, gyroscopes), vibration sensors, piezoelectric sensors, strain gauges, pH sensors, conductivity sensors, gas flow sensors, gas detection sensors, humidity or moisture sensors, physiological sensors (e.g., electrocardiography sensors, bio-impedance sensors, photoplethysmography sensors, galvanic skin response sensors), or combinations thereof. In some embodiments, the sensors herein can be configured as a switch that is activated and/or deactivated in response to a particular type of signal (e.g., optical, electrical, magnetic, mechanical, etc.).

A sensor 306 can be located at any portion of an intraoral appliance, such as at or near a distal portion, a mesial portion, a buccal portion, a lingual portion, a gingival portion, an occlusal portion, or a combination thereof. A sensor 306 can be positioned near a tissue of interest when the appliance is worn in the patient's mouth, such as near or adjacent the teeth, gingiva, palate, lips, tongue, cheeks, airway, or a combination thereof. For example, when the appliance is worn, the sensor(s) 306 can cover a single tooth, or a portion of a single tooth. Alternatively, the sensor(s) 306 can cover multiple teeth or portions thereof. In embodiments where multiple sensors 306 are used, some or all of the monitoring devices can be located at different portions of the appliance and/or intraoral cavity. Alternatively, some or all of the sensor 306 can be located at the same portion of the appliance and/or intraoral cavity.

An analog-to-digital converter (ADC) (not shown) can be used to convert analog sensor data into digital format, if desired. The processor 302 can process the sensor data obtained by the sensor(s) 306 in order to determine appliance usage and/or patient compliance, as described herein. The sensor data and/or processing results can be stored in the memory 304. Optionally, the stored data can be associated with a timestamp generated by the clock 308 (e.g., a real-time clock or counter).

The monitoring device 300 may include a communication unit 310 configured to transmit the data stored in the memory (e.g., sensor data and/or processing results) to a remote device. The communication unit 310 can utilize any suitable communication method, such as wired or wireless communication methods (e.g., RFID, near-field communication, Bluetooth, ZigBee, infrared, etc.). The communication unit 310 can include a transmitter for transmitting data to the remote device and an antenna 312. Optionally, the communication unit 310 includes a receiver for receiving data from the remote device. In some embodiments, the communication channel utilized by the communication unit 310 can also be used to power the device 300, e.g., during data transfer or if the device 300 is used passively.

The remote device can be any computing device or system, such as a mobile device (e.g., smartphone), personal computer, laptop, tablet, wearable device, etc. Optionally, the remote device can be a part of or connected to a cloud computing system ("in the cloud"). The remote device can be associated with the patient, the treating practitioner, medical practitioners, researchers, etc. In some embodiments, the remote device is configured to process and analyze the data from the monitoring device 300, e.g., in order to monitor patient compliance and/or appliance usage, for research purposes, and the like.

The monitoring device 300 can be powered by a power source 316, such as a battery. In some embodiments, the power source 316 is a printed and/or flexible battery, such as a zinc-carbon flexible battery, a zinc-manganese dioxide printed flexible battery, or a solid-state thin film lithium phosphorus oxynitride battery. The use of printed and/or flexible batteries can be advantageous for reducing the overall size of the monitoring device 300 and avoiding patient discomfort. For example, printed batteries can be fabricated in a wide variety of shapes and can be stacked to make three-dimensional structures, e.g., to conform the appliance and/or teeth geometries. Likewise, flexible batteries can be shaped to lie flush with the surfaces of the appliance and/or teeth. Alternatively or in combination, other types of batteries can be used, such as supercapacitors. In some embodiments, the power source 316 can utilize lower power energy harvesting methods (e.g., thermodynamic, electrodynamic, piezoelectric) in order to generate power for the monitoring device 300. Optionally, the power source 316 can be rechargeable, for example, using via inductive or wireless methods. In some embodiments, the patient can recharge the power source 316 when the appliance is not in use. For example, the patient can remove the intraoral appliance when brushing the teeth and place the appliance on an inductive power hub to recharge the power source 316.

Optionally, the monitoring device 300 can include a power management unit 314 connected to the power source 316. The power management unit 314 can be configured to control when the monitoring device 300 is active (e.g., using power from the power source 316) and when the device 300 is inactive (e.g., not using power from the power source 316). In some embodiments, the monitoring device 300 is only active during certain times so as to lower power consumption and reduce the size of the power source 316, thus allowing for a smaller monitoring device 300. In some embodiments, the monitoring device 300 includes an activation mechanism (not shown) for controlling when the monitoring device 300 is active (e.g., powered on, monitoring appliance usage) and when the monitoring device 300 is dormant (e.g., powered off, not monitoring appliance usage). The activation mechanism can be provided as a discrete component of the monitoring device 300, or can be implemented by the processor 302, the power management unit 314, or a combination thereof. The activation mechanism can be used to reduce the amount of power used by the monitoring device 300, e.g., by inactivating the device 300 when not in use, which can be beneficial for reducing the size of the power supply 316 and thus the overall device size.

In some embodiments, the monitoring device 300 is dormant before being delivered to the patient (e.g., during storage, shipment, etc.) and is activated only when ready for use. This approach can be beneficial in conserving power expenditure. For example, the components of the monitoring device 300 can be electrically coupled to the power source 316 at assembly, but may be in a dormant state until activated, e.g., by an external device such as a mobile device, personal computer, laptop, tablet, wearable device, power hub etc. The external device can transmit a signal to the monitoring device 300 that causes the activation mechanism to activate the monitoring device 300. As another example, the activation mechanism can include a switch (e.g., mechanical, electronic, optical, magnetic, etc.), such that the power source 316 is not electrically coupled to the other components of the monitoring device 300 until the switch is triggered. For example, in some embodiments, the switch is a reed switch or other magnetic sensor that is held open by a magnet. The magnet can be removably attached to the monitoring device 300, or may be integrated into the packaging for the device 300 or appliance, for example. When the monitoring device is separated from the magnet (e.g., by removing the magnet or removing the device and appliance from the packaging), the switch closes and connects the power source 316. As another example, the monitoring device 300 can include a mechanical switch such as a push button that is manually actuated in order to connect the power source 316. In some embodiments, the activation mechanism includes a latching function that locks the switch upon the first actuation to maintain connectivity with the power source so as to maintain activation of the monitoring device 300. Optionally, the switch for the activation mechanism can be activated by a component in the patient's intraoral cavity (e.g., a magnet coupled to a patient's tooth), such that the monitoring device 300 is active only when the appliance is worn by the patient, and is inactive when the appliance is removed from the patient's mouth. Alternatively or in combination, the switch can be activated by other types of signals, such as an optical signal.

Figure 23:
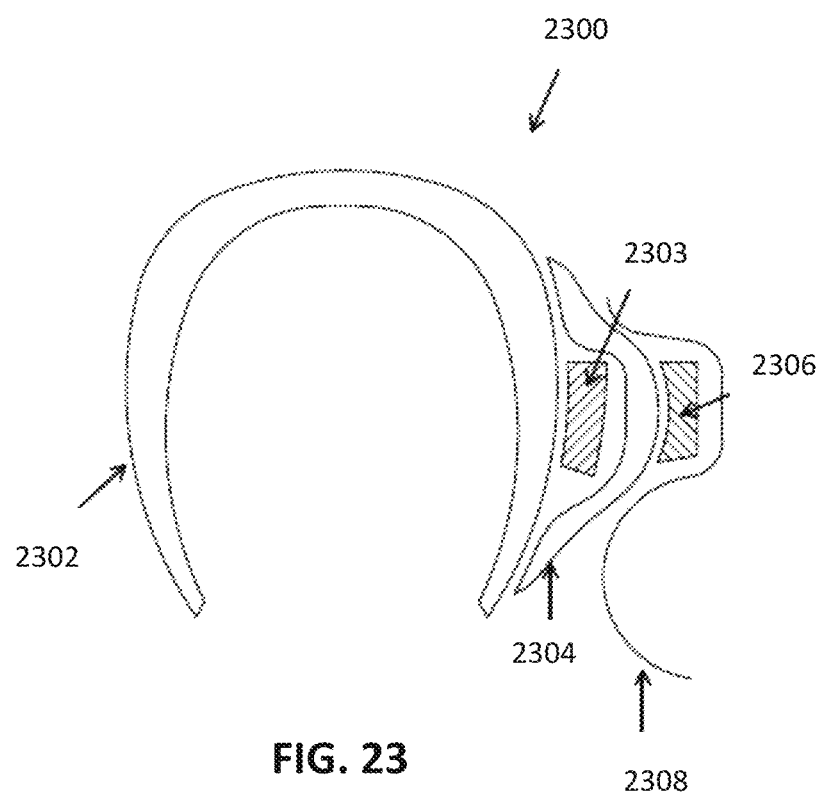
FIG. 23 illustrates an example of a monitoring device.

FIG. 23 illustrates a monitoring device 2300 with an activation mechanism, in accordance with embodiments. The monitoring device 2300, as with all other monitoring devices described herein, can be similar to the monitoring device 300, and can include some or all of the components described herein with respect to the monitoring device 300. The device 2300 is coupled to an intraoral appliance 2302 (e.g., via an encapsulating material 2304). The device 2300 can include an activation mechanism 2303 including a magnetic switch. Prior to use, the device 2300 can be removably coupled to a magnet 2306 (e.g., using tape 2308), and the magnet 2306 can hold the magnetic switch in an open position such that the device 2300 is inactive. When the appliance 2302 is ready for use, the user can remove the magnet 2306, thus closing the magnetic switch and connecting the components of the monitoring device 2300 to a power source. The intraoral appliances and monitoring devices described herein can be configured in many different ways. In some embodiments, an intraoral appliance as described herein is operably coupled to a single monitoring device. Alternatively, the intraoral appliance can be operably coupled to a plurality of monitoring devices, such as at least two, three, four, five, or more monitoring devices. Some or all of the monitoring devices may be of the same type (e.g., collect the same type of data). Alternatively, some or all of the monitoring devices may be of different types (e.g., collect different types of data). Any of the embodiments of monitoring devices described herein can be used in combination with other embodiments in a single intraoral appliance.

A monitoring device can be located at any portion of the appliance, such as at or near a distal portion, a mesial portion, a buccal portion, a lingual portion, a gingival portion, an occlusal portion, or a combination thereof. The monitoring device can be positioned near a tissue of interest when the appliance is worn in the patient's mouth, such as near or adjacent the teeth, gingiva, palate, lips, tongue, cheeks, airway, or a combination thereof. For example, when the appliance is worn, the monitoring device can cover a single tooth, or a portion of a single tooth. Alternatively, the monitoring device can cover multiple teeth or portions thereof. In embodiments where multiple monitoring devices are used, some or all of the monitoring devices can be located at different portions of the appliance. Alternatively, some or all of the monitoring devices can be located at the same portion of the appliance.

A monitoring device can be operably coupled to the intraoral appliance in a variety of ways. For example, the monitoring device can be physically integrated with the intraoral appliance by coupling the monitoring device to a portion of the appliance (e.g., using adhesives, fasteners, latching, laminating, molding, etc.). The coupling may be a releasable coupling allowing for removal of the monitoring device from the appliance, or may be a permanent coupling in which the monitoring device is permanently affixed to the appliance. Alternatively or in combination, the monitoring device can be physically integrated with the intraoral appliance by encapsulating, embedding, printing, or otherwise forming the monitoring device with the appliance. In some embodiments, the appliance includes a shell shaped to receive the patient's teeth, and the monitoring device is physically integrated with the shell. The monitoring device can be located on an inner surface of the shell (e.g., the surface adjacent to the received teeth), an outer surface of the shell (e.g., the surface away from the received teeth), or within a wall of the shell. Optionally, as discussed further herein, the shell can include a receptacle shaped to receive the monitoring device. Exemplary methods for fabricating an appliance with a physically integrated monitoring device (e.g., by incorporating some or all of the components of the monitoring device during direct fabrication of the appliance) are described in further detail herein.

Figure 3B:
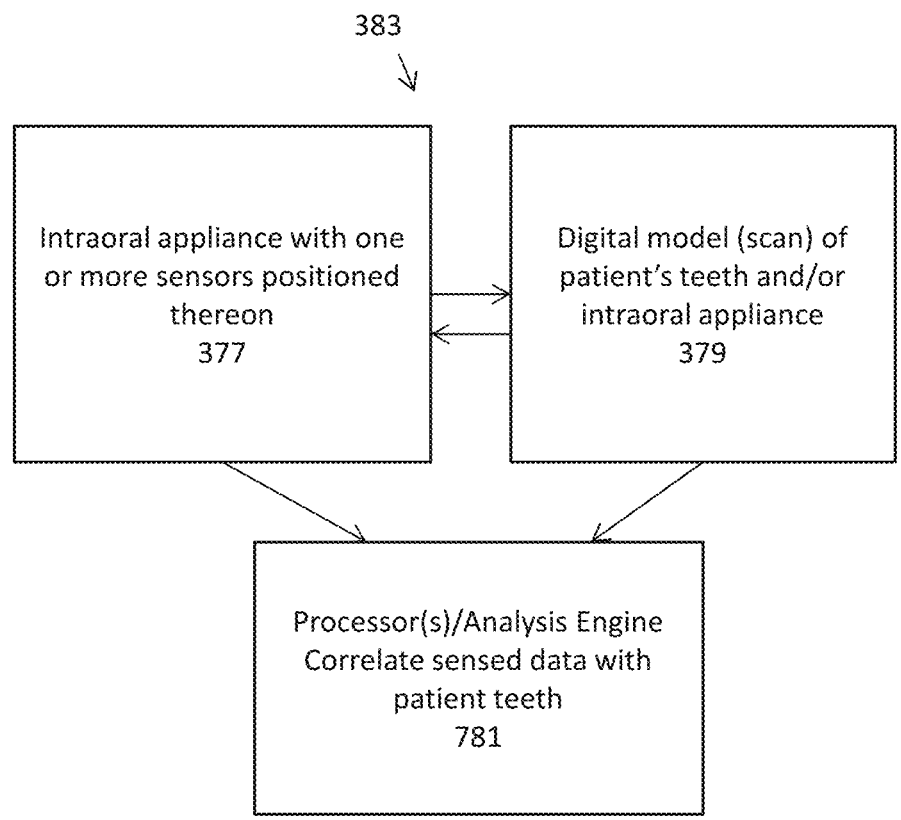
FIG. 3B schematically illustrates a system including any of the intraoral appliances with one or more sensors as described herein, and digital scan data of the appliance and/or patient's teeth. An analysis engine (which may be part of the intraoral appliance or separate from the intraoral appliance) may integrate the distal information and the sensor information, and may relate the specific sensor information to the patient's teeth using the digital scan data.

In general any of the apparatuses described herein may be used in conjunction with digital model(s) or scans or the patient's teeth and/or intraoral appliance. For example, FIG. 3B schematically illustrates a system 383 including an intraoral appliance 377 with one or more sensors, and digital scan data of the appliance and/or patient's teeth 379. An analysis engine 381 (which may be part of the intraoral appliance or separate from the intraoral appliance) may integrate the distal information and the sensor information, and may relate the specific sensor information to the patient's teeth using the digital scan data.

Figure 4A:
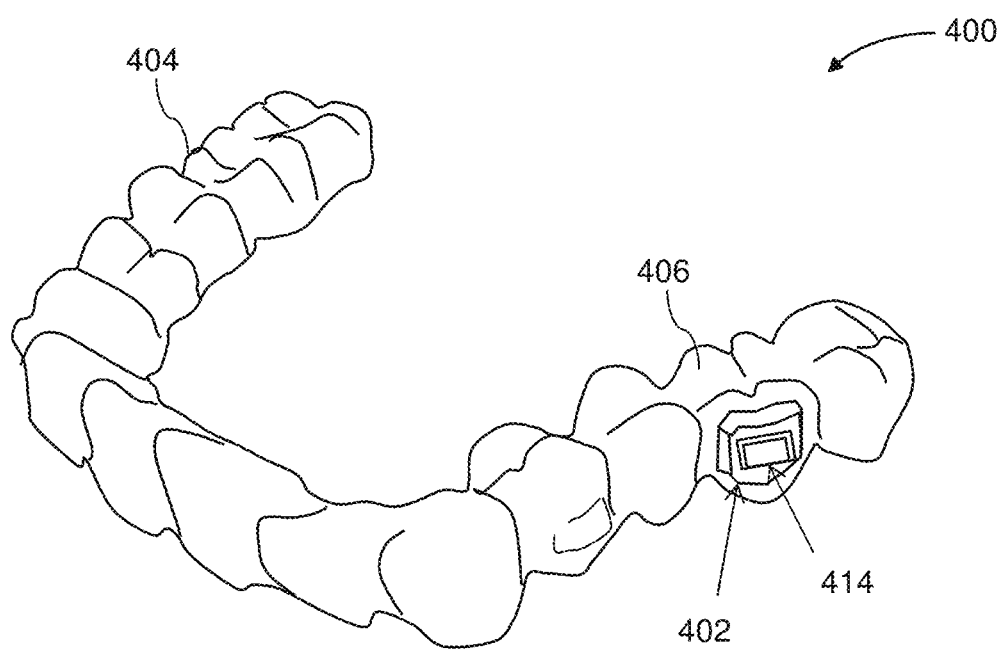
FIG. 4A illustrates an example of an intraoral appliance including an integrated monitoring device.
Figure 4B:
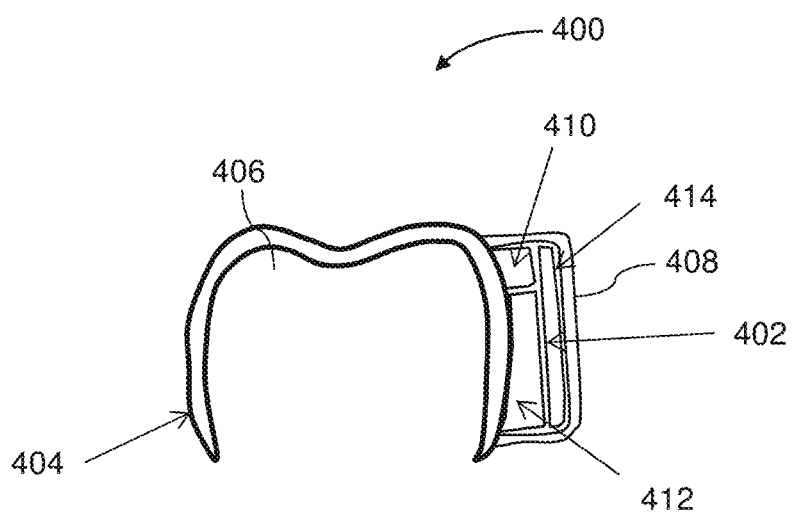
FIG. 4B is a cross-sectional view of the appliance of FIG. 4A.

FIGS. 4A and 4B illustrate an intraoral appliance 400 including an integrated monitoring device 402, in accordance with embodiments. The appliance 400 includes a shell 404 having a plurality of teeth receiving cavities, and the monitoring device 402 is coupled to an outer, buccal surface of the shell 404 adjacent a tooth receiving cavity 406. In the depicted embodiment, the monitoring device 402 is coupled to a tooth receiving cavity 406 for a molar. It shall be appreciated that in alternative embodiments, the monitoring device 402 can be coupled to other portions of the shell 404, such as an inner surface, a lingual surface, an occlusal surface, one or more tooth receiving cavities for other types of teeth (e.g., incisor, canine, premolar), etc. The monitoring device 402 can be shaped to conform to the geometry of the corresponding appliance portion (e.g., the wall of the cavity 306) so as to provide a lower surface profile and reduce patient discomfort. In some embodiments, the appliance 400 includes a receptacle 408 formed on the outer surface of the shell 404 and the monitoring device 402 is positioned within the receptacle. Exemplary methods for forming an appliance with a receptacle 408 and integrated monitoring device 402 are described in detail below.

The monitoring device 402 can include any of the components previously described herein with respect to the monitoring device 300 of FIG. 3A. For example, the monitoring device 402 can include a sensor 410, a power source 412 (e.g., a battery), and/or a communication unit 414 (e.g., a wireless antenna). The arrangement of the components of the monitoring device 402 can be varied as desired. In some embodiments, the sensor 408 is located adjacent to the tooth receiving cavity 406. A gap can be formed in the shell 404 adjacent to the sensor 410 so as to permit direct access to the received tooth. The communication unit 414 (or a component thereof, such as an antenna) can be located adjacent to or on the outer surface of the receptacle 408 so as to facilitate data transmission.

Figure 5:
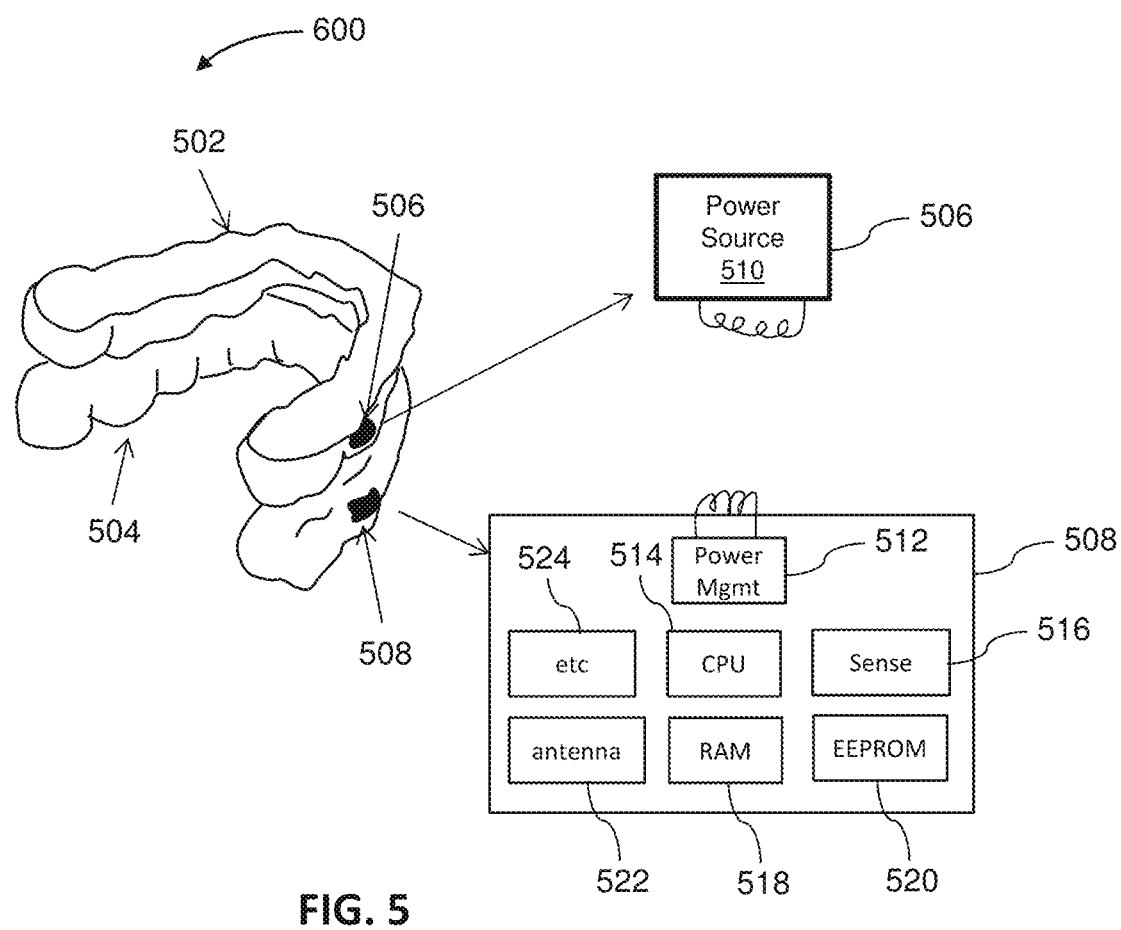
FIG. 5 illustrates an example of a monitoring system including a first appliance and a second appliance.

In some embodiments, some of the components of a monitoring device may be packaged and provided separately from other components of the device. For example, a monitoring device can include one or more components that are physically integrated with a first intraoral appliance and one or more components that are physically integrated with a second intraoral appliance. The first and second intraoral appliances can be worn on opposing jaws, for example. Any of the components of a monitoring device (e.g., components of the device 300 of FIG. 3A) can be located on an appliance for the upper jaw, an appliance for the lower jaw, or a combination thereof. In some embodiments, it is beneficial to distribute the components of the monitoring device across multiple appliances in order to accommodate space limitations, accommodate power limitations, and/or improve sensing, for example. Additionally, some of the components of a monitoring device can serve as a substrate for other components (e.g., a battery serves as a substrate to an antenna). FIG. 5 illustrates a monitoring system 500 including a first appliance 502 and a second appliance 504, in accordance with embodiments. The first appliance 502 can be shaped to receive teeth of a patient's upper arch and the second appliance 504 can be shaped to receive teeth of a patient's lower arch. The system 500 can include a monitoring device separated into a first subunit 506 physically integrated with the first appliance 502 and a second subunit 508 physically integrated with the second appliance 508. In some embodiments, the first subunit 506 is a power supply subunit including a power source 510, and the second subunit 508 is a sensing subunit including the remaining components of the monitoring device, such as a power management unit 512, processor (e.g., CPU 514), sensor 516, memory (e.g., RAM 518 such as SRAM or DRAM; ROM such as EPROM, PROM, or MROM; or hybrid memory such as EEPROM 520, flash, or NVRAM), communication unit (e.g., antenna 522), or any other component 524 described herein (e.g., with respect to the monitoring device 300 of FIG. 3A). The first subunit 506 and second subunit 508 can be operably coupled to each other via inductive coupling between the power supply 510 and power management unit 512, e.g., when the first appliance 502 and second appliance 504 are brought into proximity with each other by the closing of the patient's jaws.

The configuration of FIG. 5 can be varied as desired. For example, the first subunit 506 can be physically integrated with the second appliance 504 and the second subunit 508 can be physically integrated with the first appliance 502. As another example, the distribution of the monitoring device components between the first subunit 506 and second subunit 508 can differ from the depicted embodiment.

Alternatively or in combination, a monitoring device can include one or more components that are physically integrated with an intraoral appliance and one or more components that are physically integrated with another device external to the patient's intraoral cavity. For example, the external device can be a wearable device (e.g., headgear, smart watch, wearable computer, etc.) worn on another portion of the patient's body. As another example, the external device can be a power hub, a mobile device, personal computer, laptop, tablet, etc. Any of the components of a monitoring device (e.g., components of the device 300 of FIG. 3A) can be located on an external device. In some embodiments, the monitoring device includes a communication unit and antenna integrated into the intraoral appliance that transmits sensor data from the patient's intraoral cavity to the external device, and optionally receives data from the external device. The monitoring device components integrated into the external device can provide additional functionality (e.g., processing and/or analysis capabilities) that augments the functionality of the monitoring device components within the intraoral appliance. The monitoring device components within the intraoral appliance may be capable of operating with or without the augmented functionalities.

Alternatively or in combination, a monitoring device can include one or more components that are physically integrated with an intraoral appliance and one or more components that are located in the patient's intraoral cavity separate from the appliance. The intraoral components can be positioned so as to interact with (e.g., physically contact, communicate with) the integrated components in the appliance when the appliance is worn. In some embodiments, the intraoral components are coupled to a portion of the intraoral cavity, such as a crown of the patient's tooth. For instance, the intraoral components can be physically integrated into an attachment device mounted on a patient's tooth. Alternatively or in combination, the monitoring device can be surgically implanted, e.g., in the bone of the patient's jaw. Any of the components of a monitoring device (e.g., components of the device 300 of FIG. 3A) can be located in the patient's intraoral cavity rather than in the intraoral appliance. In some embodiments, the appliance and integrated components can be removed from the patient's mouth independently of the intraoral components. Advantageously, this approach may reduce costs by allowing the same device components to be used with multiple different appliances, e.g., when applying a sequence of shell appliances to reposition the patient's teeth.

Figure 6A:
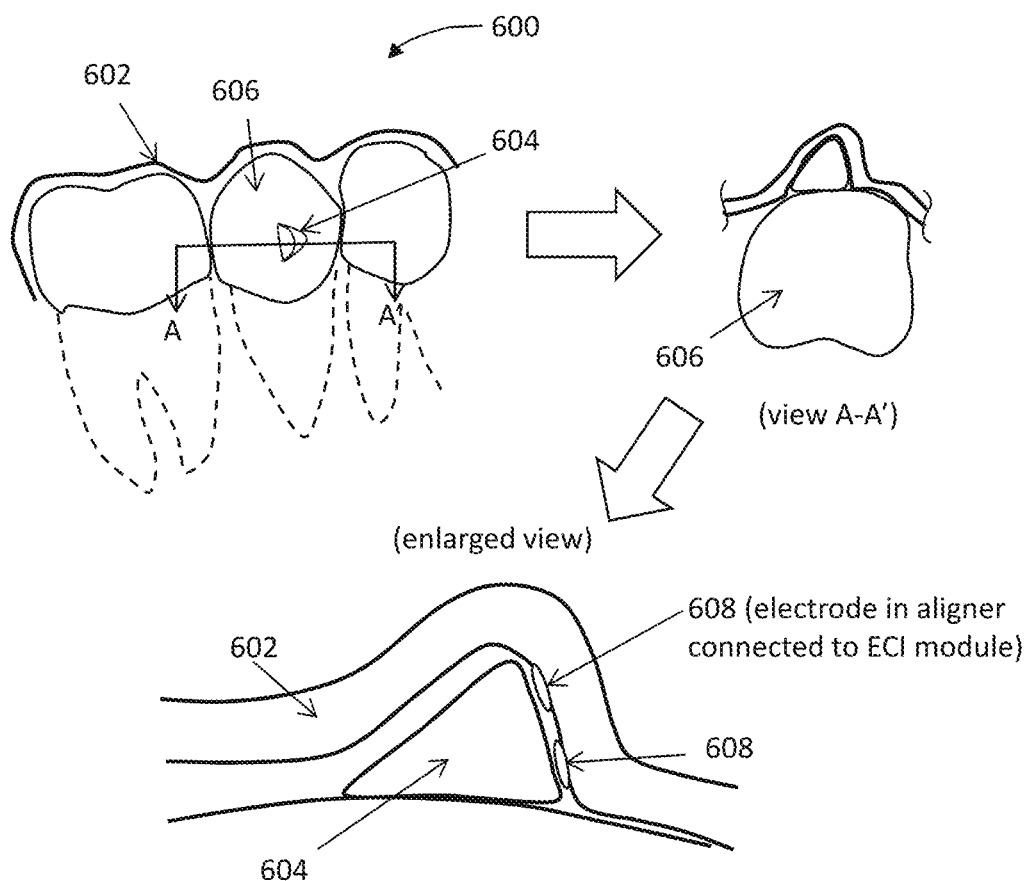
FIG. 6A illustrates an example of a system including an intraoral appliance and an attachment device mounted on a tooth.

FIG. 6A illustrates a system 600 including an intraoral appliance 602 and an attachment device 604 mounted on a tooth 606, in accordance with embodiments. The appliance 602 can include a shell with a tooth receiving cavity shaped to receive the tooth 606 and a receptacle shaped to accommodate the attachment device 604 on the tooth 606. In some embodiments, the system 600 includes a monitoring device having a first subunit physically integrated into the appliance 602 (e.g., according to any of the methods described herein) and a second subunit physically integrated into the attachment device 604. In some embodiments, the second subunit integrated into the attachment device 604 includes the relatively bulky components of the monitoring device, such as the power source, memory, and/or sensors. For example, the attachment device 604 can include a battery or other power source operably coupled to the monitoring device components integrated into the appliance 602, e.g., via inductive coupling or direct contact using electrodes 608. In alternative embodiments, this configuration can be reversed, with the power source mounted in the appliance 602 and the remaining monitoring device components located in the attachment device 604. This approach can reduce costs when multiple appliances are used, since only the power source is replaced with each new appliance. As another example, the attachment device 604 can include a passive sensing element driven by one or more monitoring device components located in the appliance 602. In yet another example, the attachment device 604 can include a conductive element used to trigger a switch integrated in the appliance 602.

Figure 6B:
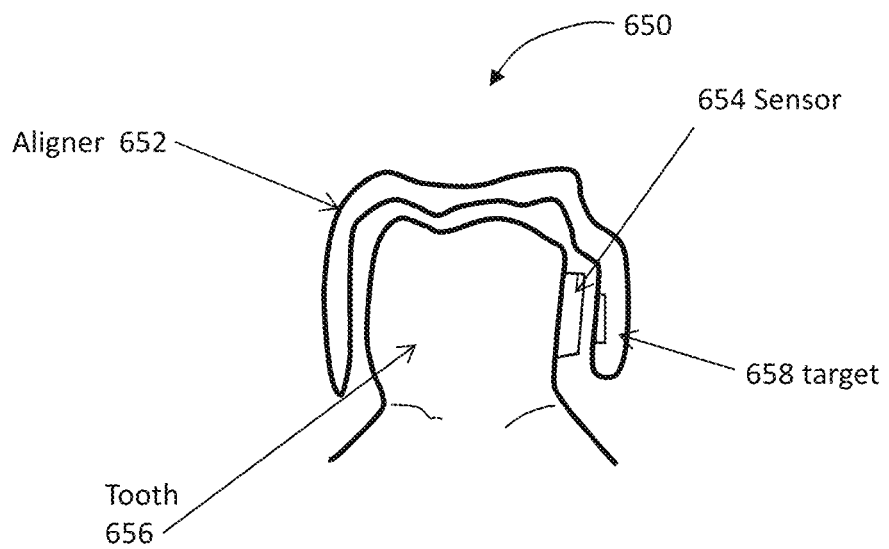
FIG. 6B shows an example of a system including an intraoral appliance and an attachment device mounted on a tooth.

FIG. 6B illustrates a system 650 including an intraoral appliance 652 and an attachment device 654 mounted on a tooth 656, in accordance with embodiments. Similar to the appliance 600, the appliance 652 can include a shell with a tooth receiving cavity shaped to receive the tooth 656 and a receptacle shaped to accommodate the attachment device 654 on the tooth 656. In some embodiments, the system 650 includes a monitoring device having a first subunit physically integrated into the appliance 652 (e.g., according to any of the methods described herein) and a second subunit physically integrated into the attachment device 654. The first subunit in the appliance 652 can include a sensing target 658 and the second subunit in the attachment device 654 can include one or more sensors configured to detect the target. For example, the sensing target 658 can be a mirror or opaque surface and the sensor can be a photodetector. As another example, the sensing target 658 can be a magnet and the sensor can be a magnetometer. In yet another example, the sensing target 658 can be a metallic element (e.g., foil, coating) and the sensor can be a capacitive sensor. Optionally, the sensing target 658 can be a powered coil generating an AC electromagnetic field, such that the sensor also obtains power from the sensing target 658. In alternative embodiments, the locations of the first and second subunits can be reversed, such that the sensing target 658 is located in the attachment device 654 and the sensor is located in the appliance 652.

The monitoring devices of the present disclosure may utilize many different types and configurations of sensors. The description below of certain exemplary monitoring devices is not intended to be limiting, and it shall be appreciated that the features of the various embodiments described herein can be used in combination with features of other embodiments. For example, the monitoring devices discussed below may also include any of the components previously described with respect to the monitoring device 300 of FIG. 3A. A single monitoring device can include any combination of the sensor types and sensor configurations described herein.

In some embodiments, a monitoring device includes a structure shaped to interact with the sensor when the intraoral appliance is worn on the patient's teeth. The monitoring device can include one or more deflectable structures (e.g., a cantilever, dimple, concavity, flap, protrusion, pop-out structure, etc.) formed with or coupled to the appliance. The deflectable structure can be deflected outward by the patient's tooth or an attachment device coupled to the tooth when the appliance is worn, for example. In some embodiments, the monitoring device includes a sensor (e.g., a mechanical switch such as a push button), an electrical switch, an optical switch, a proximity sensor, a touch sensor, etc., configured to generate sensor data indicative of deflection of the deflectable structure (e.g., whether the structure is deflected, the deflection distance, etc.). The monitoring device can also include a processor operably coupled to the sensor and configured to process the sensor data so as to generate appliance usage and/or compliance data (e.g., information regarding whether the appliance is being worn). Optionally, the sensor can provide more complex data (e.g., force and/or pressure data) regarding the interaction between the appliance and the patient's teeth. In some embodiments, the deflectable structure is in a deflected state when the appliance is being worn and in a resting state when the appliance is not being worn, and the deflectable structure interacts with (e.g., activates) the sensor only when in the deflected state.

FIGS. 7A and 7B illustrate a monitoring device 700 with a deflectable structure 702, in accordance with embodiments. In the depicted embodiment, the deflectable structure 702 is formed in a shell 704 of an intraoral appliance, e.g., in a wall of a tooth receiving cavity 706. The monitoring device 700 can include a sensor 708 (e.g., push button) configured to detect the deflection of the deflectable structure 702. When the appliance is not being worn on the patient's teeth (FIG. 7A), the deflectable structure 702 can be in a resting state such that the sensor 708 is not activated. When the appliance is worn by the patient, the tooth 710 (e.g., a first or second molar) can displace the deflectable structure 702 outwards to activate the sensor 708. The deflection distance can be varied as desired. For instance, the structure 702 can be deflected outward by a distance of at least about 25 µm, at least about 30 µm, at least about 50 µm, at least about 100 µm, at least about 200 µm, at least about 300 µm, or a distance within a range from about 25 µm to about 300 µm. The monitoring device 700 can include other components (e.g., as previously described with respect to FIG. 3A) for storing, processing, analyzing, and/or transmitting the sensor data.

FIG. 7C illustrates a monitoring device 720 with a deflectable structure 722, in accordance with embodiments. The deflectable structure 722 is formed in a shell of an intraoral appliance, e.g., in a wall of a tooth receiving cavity 724. The tooth receiving cavity 724 is shaped to receive a tooth 726 coupled to an attachment device 728. In some embodiments, the attachment device 728 includes an activator structure 730 that deflects the deflectable structure 722 when the tooth 726 is received in the cavity 724. The monitoring device 720 includes a sensing subunit 732 mounted to the shell near the deflectable structure 722. The sensing subunit 732 includes a sensor 734 (e.g., a switch) that is activated by the deflection of the deflectable structure 722. Optionally, the sensor 732 can be covered with a flexible membrane. The subunit 732 can also include a power source, a processor, and/or any of the other monitoring device components described herein (e.g., with respect to the embodiment of FIG. 3A).

Figure 7D:
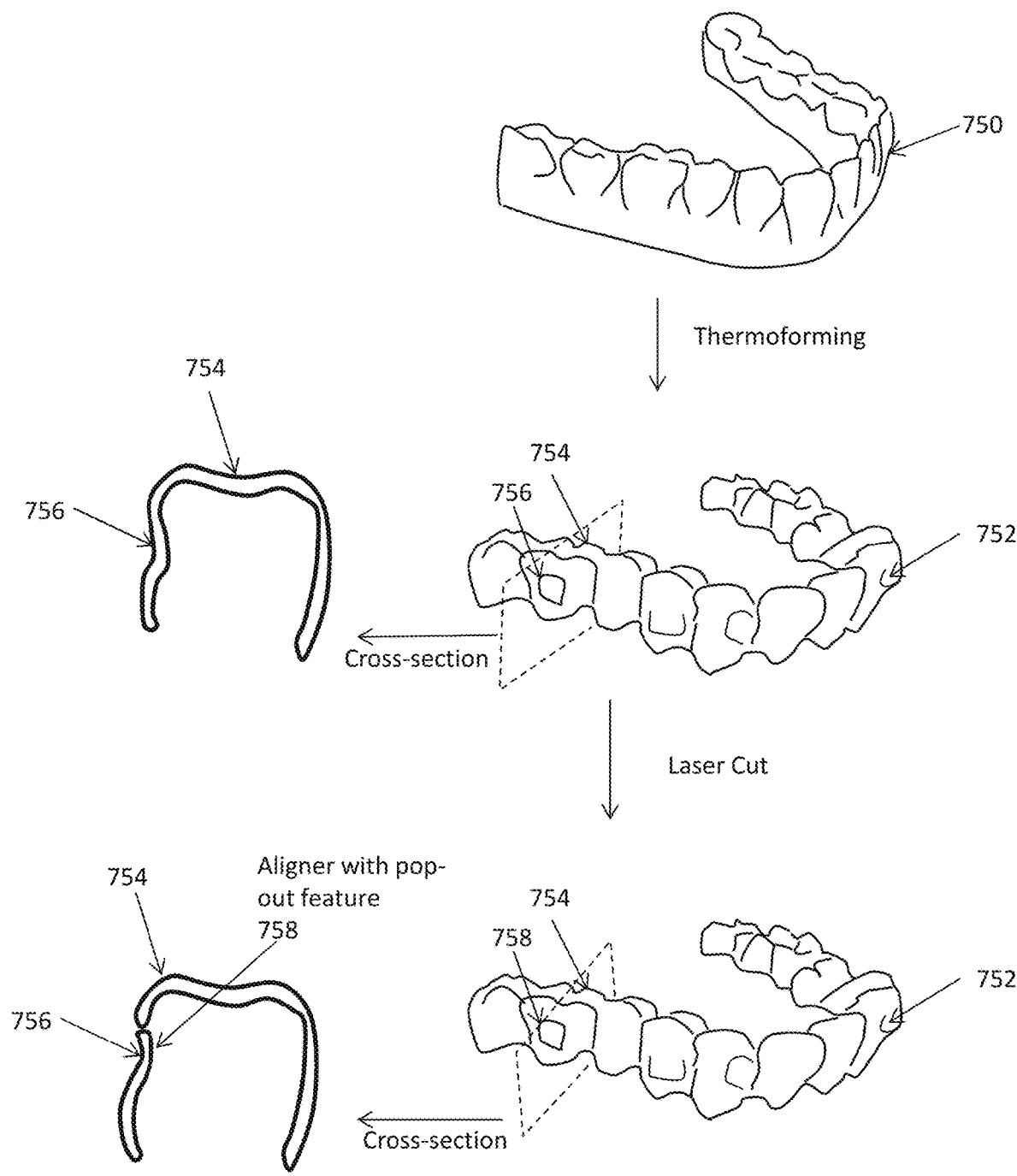
FIG. 7D illustrates an exemplary method for fabricating an intraoral appliance with a deflectable structure.

FIG. 7D illustrates a method for fabricating an intraoral appliance with a deflectable structure, in accordance with embodiments. In the first step, a mold 750 of a patient's dentition is provided. The mold 750 can represent the patient's teeth in a current or target tooth arrangement, for example. In a second step, an intraoral appliance 752 is formed by forming (e.g., thermoforming) a material over the mold 750. Alternatively, the intraoral appliance 752 can be formed by direct fabrication (e.g., stereolithography, 3D printing, etc.) without using the mold 750. The appliance can include a shell with a tooth receiving cavity 754 having a dimple or concavity 756 at the target location for the deflectable structure. In a third step, a deflectable structure 758 is formed in the appliance 752 by cutting the wall of the cavity 754 so as to form a cantilevered portion. Cutting of the appliance 752 can be performed using methods known to those of skill in the art, such as laser cutting or milling. Subsequently, the other components of the monitoring device can be coupled to the appliance 752 adjacent to or near the deflectable structure 758.

Alternatively or in combination, a monitoring device can include one or more proximity sensors configured to generate sensor data when in proximity to a sensing target. Examples of proximity sensors suitable for use with the embodiments herein include capacitive sensors, resistive sensors, inductive sensors, eddy-current sensors, magnetic sensors, optical sensors, photoelectric sensors, ultrasonic sensors, Hall Effect sensors, infrared touch sensors, or surface acoustic wave (SAW) touch sensors. A proximity sensor can be activated when within a certain distance of the sensing target. The distance can be about less than 1 mm, or within a range from about 1 mm to about 50 mm. In some embodiments, a proximity sensor can be activated without direct contact between the sensor and the sensing target (e.g., the maximum sensing distance is greater than zero).

In some embodiments, a proximity sensor is activated when in direct contact with the sensing target (the sensing distance is zero), also known as a touch or tactile sensor. Examples of touch sensors include capacitive touch sensors, resistive touch sensors, inductive sensors, pressure sensors, and force sensors. In some embodiments, a touch sensor is activated only by direct contact between the sensor and the sensing target (e.g., the maximum sensing distance is zero). Some of the proximity sensor types described herein (e.g., capacitive sensors) may also be touch sensors, such that they are activated both by proximity to the sensing target as well as direct contact with the target.

One or more proximity sensors may be integrated in the intraoral appliance and used to detect whether the appliance is in proximity to one or more sensing targets. The sensing targets can be an intraoral tissue (e.g., the teeth, gingiva, palate, lips, tongue, cheeks, or a combination thereof). For example, proximity sensors can be positioned on the buccal and/or lingual surfaces of an appliance in order to detect appliance usage based on proximity to and/or direct contact with the patient's cheeks and/or tongue. As another example, one or more proximity sensors can be positioned in the appliance so as to detect appliance usage based on proximity to and/or direct contact with the enamel and/or gingiva. In some embodiments, multiple proximity sensors are positioned at different locations appliance so as to detect proximity to and/or direct contact with different portions of the intraoral cavity.

Alternatively or in combination, one or more sensing targets can be coupled to an intraoral tissue (e.g., integrated in an attachment device on a tooth), or can be some other component located in the intraoral cavity (e.g., a metallic filling). Alternatively or in combination, one or more proximity sensors can be located in the intraoral cavity (e.g., integrated in an attachment device on a tooth) and the corresponding sensing target(s) can be integrated in the intraoral appliance. Optionally, a proximity sensor integrated in a first appliance on a patient's upper or lower jaw can be used to detect a sensing target integrated in a second appliance on the opposing jaw or coupled to a portion of the opposing jaw (e.g., attached to a tooth), and thus detect proximity and/or direct contact between the patient's jaws.

The proximity sensor may be a capacitive sensor activated by charges on the sensing target. The capacitive sensor can be activated by charges associated with intraoral tissues or components such as the enamel, gingiva, oral mucosa, saliva, cheeks, lips, and/or tongue. For example, the capacitive sensor can be activated by charges (e.g., positive charges) associated with plaque and/or bacteria on the patient's teeth or other intraoral tissues. In such embodiments, the capacitive sensing data can be used to determine whether the appliance is being worn, and optionally the amount of plaque and/or bacteria on the teeth. As another example, the capacitive sensor can be activated by charges associated with the crowns of teeth, e.g., negative charges due to the presence of ionized carboxyl groups covalently bonded to sialic acid.

Various configurations of capacitive sensors can be used for the monitoring devices described herein. In some embodiments, the electrical charges on the surface of an intraoral tissue can interfere with the electric field of the capacitive sensor. Alternatively or in combination, the intraoral tissue can serve as the ground electrode of the capacitive sensor. Optionally, a shielding mechanism can be used to guide the electric field of the capacitive sensor in a certain location and/or direction for detecting contact with a particular tissue.

Figure 8A:
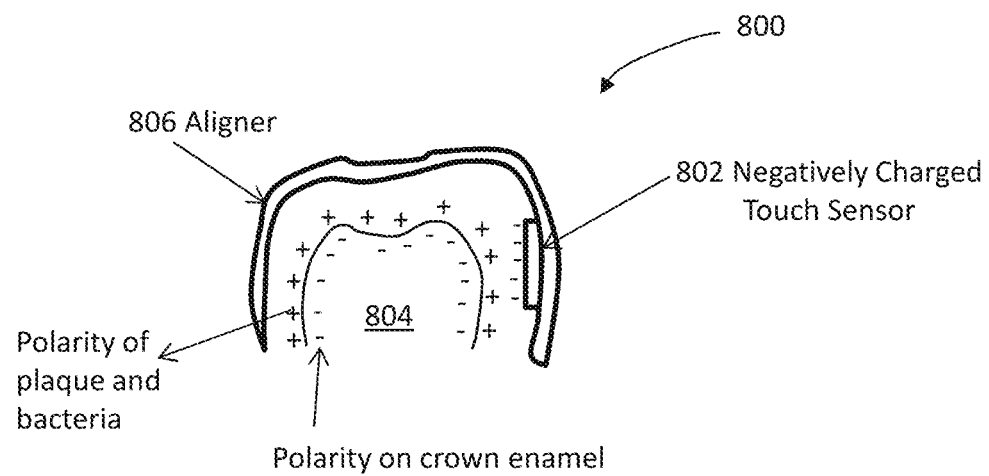
FIG. 8A illustrates an example of an intraoral appliance including a capacitive sensor.

FIG. 8A illustrates an intraoral appliance 800 including a capacitive sensor 802, in accordance with embodiments. In some embodiments, the sensing target for the capacitive sensor 802 is the surface of the patient's tooth 804, and the capacitive sensor 802 is coupled to the inner surface of a tooth receiving cavity 806 of an intraoral appliance so as to be adjacent to the tooth 804 when the appliance is worn. The capacitive sensor 802 can be activated by proximity to the tooth 804 and/or direct contact with the tooth 804. In some embodiments, the capacitive sensor 802 is activated by negative charges on the enamel of the tooth crown. Alternatively or in combination, the capacitive sensor 802 can be activated by positive charges associated with plaque and/or bacteria on the tooth crown. Optionally, the capacitive sensor 802 can be activated by charges associated with minerals in the patient's saliva on the tooth surface, including but not limited to $NH_4+$, $Ca_2+$, $PO_43"$, $HCO_3-$, and F.

Figure 8B:
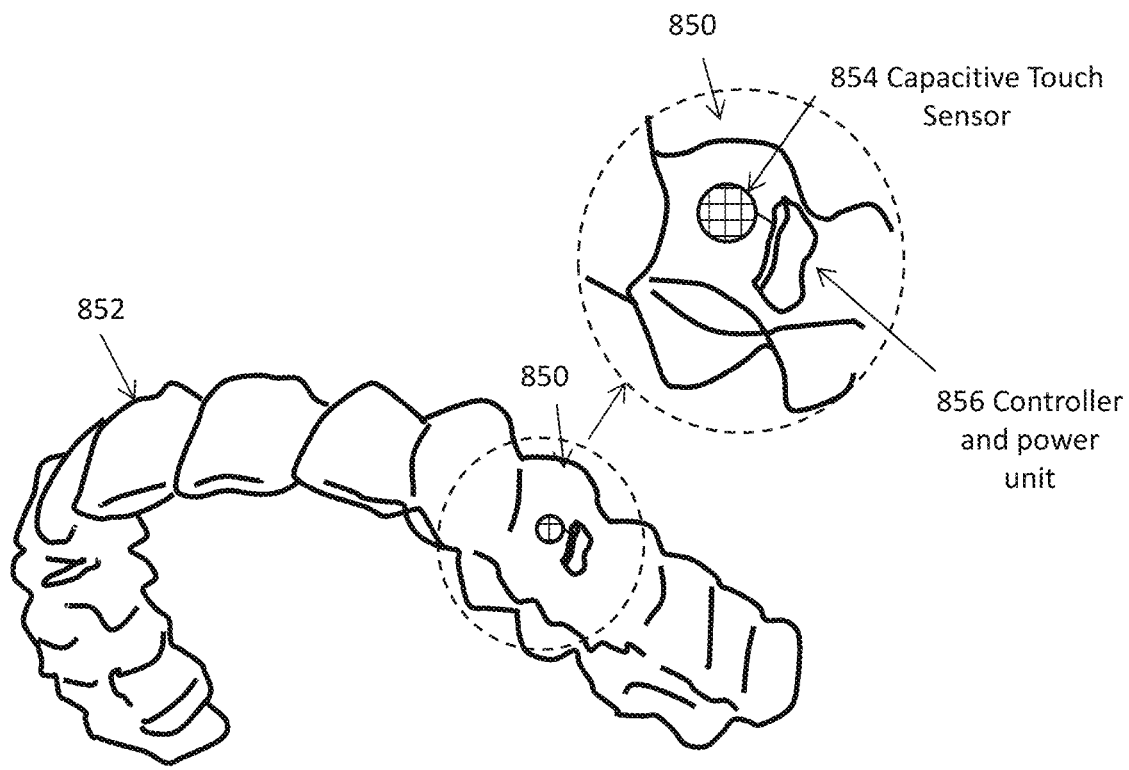
FIG. 8B illustrates an example of a monitoring device integrated into an intraoral appliance.

FIG. 8B illustrates a monitoring device 850 integrated into an intraoral appliance 852, in accordance with embodiments. The monitoring device 850 can be located on any suitable portion of the appliance 852, such as a buccal surface and/or lingual surface of the appliance 852 adjacent a tooth receiving cavity. The device 850 can include a capacitive sensor 854 (e.g., a capacitive touch sensor grid). The capacitive sensor 854 can be similar to the sensor 802 described with respect to FIG. 8A, for example. In some embodiments, the capacitive sensor 854 is flexible and/or thermoformable so as to conform to the shape of the appliance 852. The monitoring device 850 can also include a controller and power source 856 coupled to the capacitive sensor 854, as well as any of the other components described herein with respect to the monitoring device 300 of FIG. 3A. The controller and power source 856 can be used to power the capacitive sensor 854, process proximity and/or contact data obtained by the capacitive sensor 854, store the obtained data and/or processing results, and/or transmit the data and/or processing results to a remote device, for example.

Although FIG. 8B illustrates a single monitoring device 850 with a single capacitive sensor 854, other configurations can also be used. For example, in alternative embodiments, the monitoring device 850 can include multiple capacitive sensors located at different sites on the appliance 852 to detect proximity to and/or contact with multiple locations in the intraoral cavity. Optionally, multiple monitoring devices can be used, with each device being coupled to one or more respective capacitive sensors.

Figure 8C:
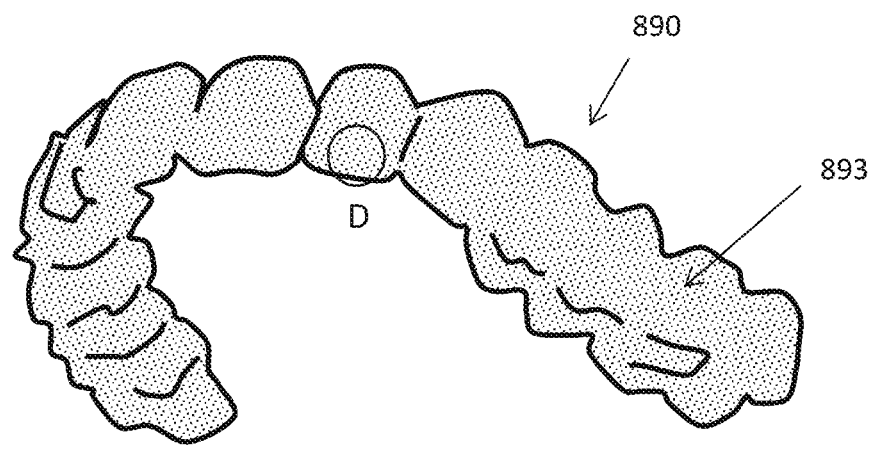
FIG. 8C illustrates an example of an intraoral appliance in which the majority of the aligner surface comprises a capacitive touch-sensor material.
Figure 8D:
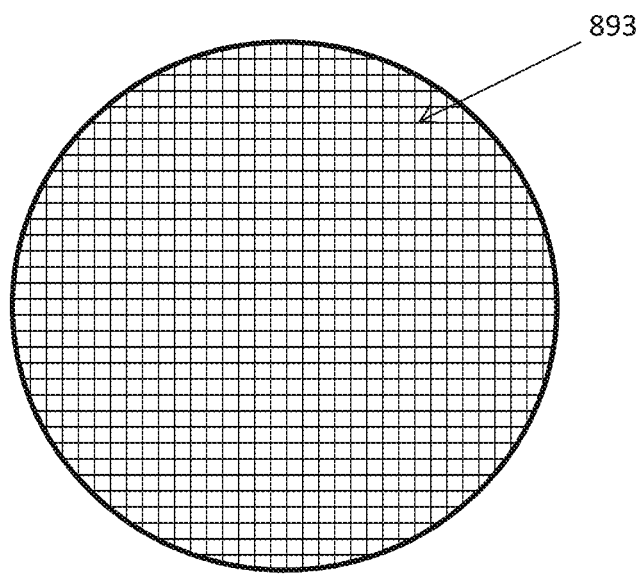
FIG. 8D illustrates an enlarged view, showing the grid pattern of the capacitive touch sensor that is distributed across the surface of the intraoral appliance of FIG. 8C.

In some variations, the majority of (or all of) the intraoral appliance (shown in this example as an aligner, but as mentioned above, may be configured as any other intraoral appliance) may include a capacitive touch-sensor material. In FIG. 8C, the aligner 890 includes a formed surface of capacitive touch-sensor material 893. FIG. 8D shows an enlarged view, showing a grid pattern of the capacitive touch sensor that may be distributed across the surface of the intraoral appliance of FIG. 8C.

The capacitive touch sensor may relate intensity and location of touch information, and may derive force (force moment, and force direction) on the patient's teeth from the intraoral appliance. In some variations the appliance may include one or more processors for receiving touch information from the grid of capacitive sensors and may correlate this information with applied force on the teeth by the apparatus. For example, the capacitive touch data may be correlate to particular teeth using a digital model of the patient's teeth and/or aligner (as discussed above generally in FIG. 3B).

FIG. 9 illustrates a monitoring system 900 for detecting proximity between the patient's jaws, in accordance with embodiments. The system 900 includes a first appliance 902 worn on the patient's upper teeth and a second appliance 904 worn on the patient's lower teeth. The system 900 also includes a monitoring device including a first sensing subunit 906 (e.g., a first plate) integrated with the first appliance 902, a second sensing subunit 908 (e.g., a second plate) integrated with the second appliance 904, and a controller 910 integrated with the first appliance 902 and coupled to the first sensing subunit 906. Alternatively, the controller 910 can be integrated with the second appliance 904 and coupled to the second sensing subunit 908. In some embodiments, the monitoring device is used to measure the capacitance and/or charge between first sensing subunit 906 and the second sensing subunit 908, and the measurement data can be used to determine whether the patient's jaws are in proximity to each other.

Alternatively or in combination, a monitoring device can include one or more vibration sensors configured to generate sensor data indicative of intraoral vibration patterns. Examples of vibration sensors include audio sensors (e.g., MEMS microphones), accelerometers, and piezoelectric sensors. The intraoral vibration patterns can be associated with one or more of: vibrations transferred to the patient's teeth via the patient's jaw bone, teeth grinding, speech, mastication, breathing, or snoring. In some embodiments, the intraoral vibration patterns originate from sounds received by the patient's ear drums. The intraoral vibration patterns may also originate from intraoral activities, such as teeth grinding, speech, mastication, breathing, snoring, etc. The sensor data generated by the vibration sensors can be processed to determine appliance usage and/or patient compliance. For instance, the monitoring device can include a processor that compares the detected intraoral vibration patterns to patient-specific intraoral vibration patterns to determine whether the appliance is being worn on a patient's teeth. In some embodiments, the processor is trained using previous data of patient-specific intraoral vibration patterns, and then determines whether the appliance is being worn by matching the measured patterns to the previous patterns. Alternatively or in combination, appliance usage can be determined by comparing the measured vibration patterns to vibration patterns obtained when the appliance is not being worn.

Alternatively or in combination, a monitoring device can include one or more optical sensors configured to detect appliance usage based on optical signals. For example, the optical sensors can be color sensors (e.g., mono-channel color sensors, multi-channel color sensors such as RGB sensors) configured to detect the colors of intraoral tissues. In some embodiments, one or more color sensors can be integrated into the intraoral appliance so as to be positioned adjacent to certain intraoral tissue (e.g., enamel, gingiva, cheeks, tongue, etc.) when the appliance is worn in the mouth. The device can determine whether the appliance is currently being worn based on whether the colors detected by the sensors match the expected colors for the tissues. In such embodiments, the monitoring device can include one or more light sources (e.g., LEDs) providing illumination for the color sensors.

As another example, the monitoring device can include one or more emitters (e.g., a LED) configured to generate optical signals and one or more optical sensors (e.g., a photodetector) configured to measure the optical signals. For example, an emitter can be positioned such that when the appliance is worn, the optical signal is reflected off of a surface (e.g., an intraoral tissue, a portion of an intraoral appliance) in order to reach the corresponding optical sensor. In some embodiments, when the appliance is not being worn, the optical signal is not reflected and does not reach the optical sensor. Accordingly, activation of the optical sensor can indicate that the appliance is currently being worn.

FIG. 10A illustrates a monitoring device 1000 utilizing optical sensing, in accordance with embodiments. The device 1000 includes an emitter 1002 and an optical sensor 1004 integrated into an intraoral appliance 1006. In the depicted embodiment, the emitter 1002 and sensor 1004 are both located on a buccal surface of the appliance 1006 such that optical signals from the emitter 1002 are reflected off the patient's cheek 1008 to reach the sensor 1004 when the appliance 1006 is worn. In alternative embodiments, the emitter 1002 and sensor 1004 can be located on a lingual surface of the appliance 1006 such that optical signals from emitter 1002 are reflected off the patient's tongue to reach the sensor 1004.

FIG. 10B illustrates a monitoring device 1020 using optical sensing, in accordance with embodiments. The device 1020 includes an emitter 1022 and an optical sensor 1024 integrated into a first intraoral appliance 1026 worn on a jaw of the patient (e.g., upper or lower jaw). The emitter 1022 and sensor 1024 can be arranged such that optical signals from the emitter 1022 reflect off of a second intraoral appliance 1028 worn on the patient's opposing jaw to reach the sensor 1024 when the first appliance 1026 and second appliance 1028 are being worn. Optionally, the second appliance 1028 can include a surface 1030 with optical properties selected to enhance and/or control reflection of the optical signal.

As another example, the emitter can be positioned such that when the appliance is worn, the optical signal is transmitted directly to the optical sensor without requiring any reflection off another surface. In some embodiments, when the appliance is not being worn, the optical signal does not reach the optical sensor. Accordingly, activation of the optical sensor can indicate that the appliance is currently being worn.

FIG. 10C illustrates a monitoring device 1040 using optical sensing, in accordance with embodiments. The device 1040 includes an emitter 1042 integrated into a first intraoral appliance 1044 worn on a jaw of the patient (e.g., upper or lower jaw) and an optical sensor 1046 integrated into a second intraoral appliance 1048 worn on the patient's opposing jaw. The emitter 1042 and sensor 1046 can be arranged such that the optical signals from the emitter 1042 are transmitted directly to the sensor 1046 when the first appliance 1044 and second appliances 1048 are worn. In yet another example, the emitter can be positioned such that when the appliance is worn, the optical signal is occluded by an intraoral tissue (e.g., the patient's tongue). In some embodiments, when the appliance is not being worn, the optical signal is not occluded and reaches the optical sensor (e.g., via direct transmission or reflection from a surface). Accordingly, activation of the optical sensor can indicate that the appliance is not currently being worn. Optionally, the optical signal can be infrared light in order to be less obtrusive to the patient.

Figures 11A, 11B:
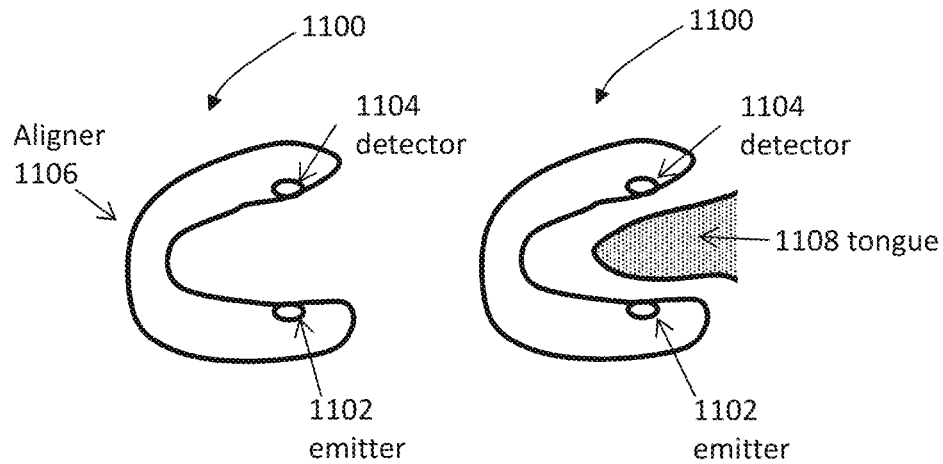
FIGS. 11A and 11B illustrate operation of an example of a monitoring device using optical sensing.

FIGS. 11A and 11B illustrate a monitoring device 1100 using optical sensing, in accordance with embodiments. The device 1100 includes an emitter 1102 and optical sensor 1104 integrated into an intraoral appliance 1106. The emitter 1102 and sensor 1104 can be positioned on opposing sides of the lingual surface of the appliance 1106 such that optical signals are transmitted directly from the emitter 1102 to the sensor 1104 when the appliance 1106 is not being worn (FIG. 11A). When the appliance 1106 is worn (FIG. 11B), the patient's tongue 1108 can occlude the transmission of optical signals between the emitter 1102 and sensor 1104.

Figures 11C, 11D:
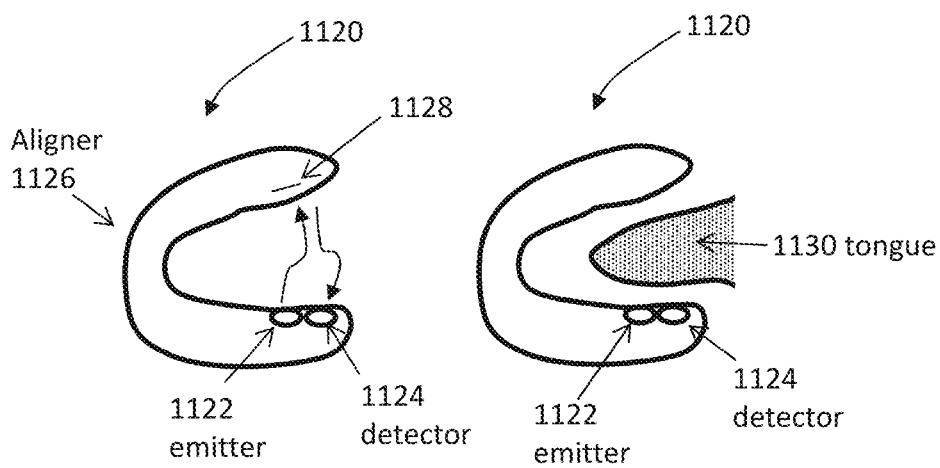
FIGS. 11C and 11D illustrate an example of a monitoring device using optical sensing.

FIGS. 11C and 11D illustrate a monitoring device 1120 using optical sensing, in accordance with embodiments. The device 1120 includes an emitter 1122 and optical sensor 1124 integrated into an intraoral appliance 1126. The emitter 1122 and sensor 1124 can be positioned the same side of the lingual surface of the appliance 1126 such that optical signals generated by the emitter 1122 are reflected off the opposing lingual surface 1128 to the sensor 1124 when the appliance 1126 is not being worn (FIG. 11C). Optionally, the optical properties of the surface 1128 can be selected to enhance and/or control the reflection of the optical signal. When the appliance 1126 is worn (FIG. 11D), the patient's tongue 1130 can occlude the transmission of optical signals between the emitter 1122 and sensor 1124.

Additionally, the optical sensing-based monitoring devices described herein can also be configured to detect variations in the reflected and/or transmitted optical signal caused by breathing, mastication, or other patient movements. This information can be used to further improve the reliability and accuracy of optical-sensing based compliance monitoring.

Alternatively or in combination, the monitoring devices of the present disclosure can include one or more magnetic sensors configured to detect appliance usage based on changes to a magnetic field. Examples of magnetic sensors suitable for use with the embodiments herein include magnetometers, Hall Effect sensors, magnetic reed switches, and magnetoresistive sensors. In some embodiments, the characteristics of the magnetic field (e.g., magnitude, direction) vary based on whether the appliance is currently being worn, e.g., due to interference from intraoral tissues such as the teeth. Accordingly, the device can determine appliance usage by processing and analyzing the magnetic field detected by the magnetic sensors.

Figures 12A, 12B:
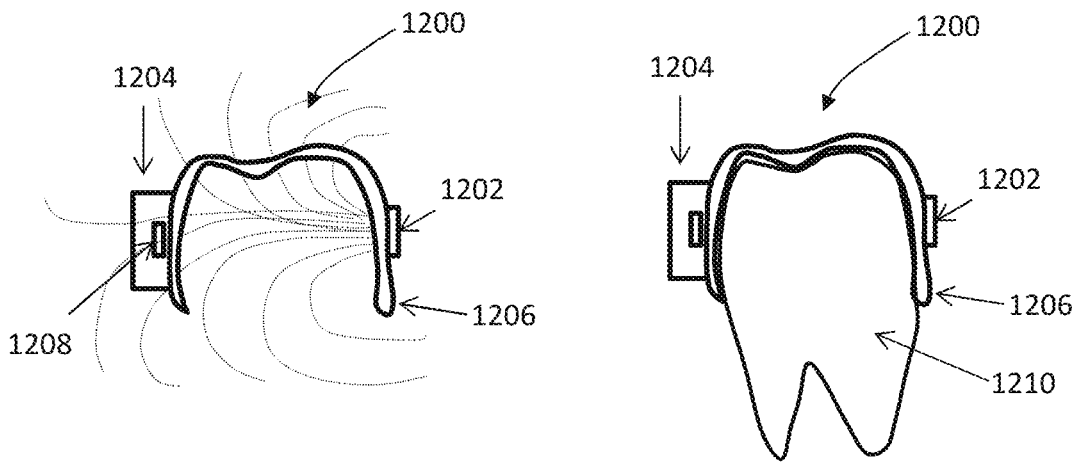
FIGS. 12A and 12B illustrate an example of a monitoring device using magnetic sensing.

FIGS. 12A and 12B illustrate a monitoring device 1200 using magnetic sensing, in accordance with embodiments. The device 1200 includes a magnet 1202 and a sensing subunit 1204 coupled to an intraoral appliance 1206. For example, the appliance 1206 can include a shell with tooth-receiving cavities and the magnet 1202 and sensing subunit 1204 can be coupled to the outer surface of a tooth receiving cavity. The sensing subunit 1204 includes one or more magnetic sensors 1208 (e.g., three magnetometers) configured to measure the characteristics (e.g., magnetic, direction) of the magnetic field generated by the magnet 1202. In some embodiments, when the appliance 1206 is worn by the patient, the tooth 1210 received in the cavity interferes with the magnetic field (FIG. 12B), such that the field characteristics differ from when the appliance is not being worn (FIG. 12A). The monitoring device 1200 can include a processor (not shown) configured to determine whether the appliance is being worn based on the sensing data produced by the magnetic sensor(s) 1208.

Figure 12C:
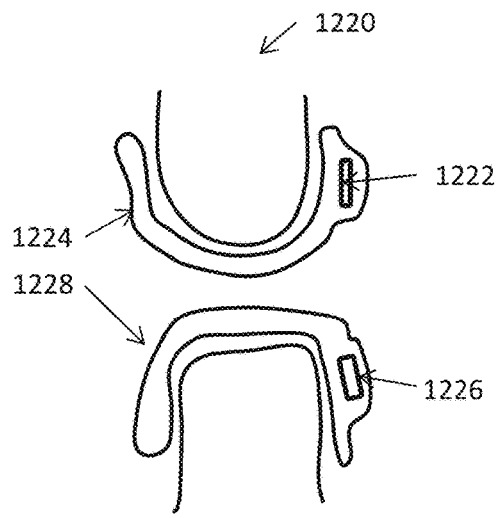
FIG. 12C shows an example of a monitoring device using magnetic sensing.

FIG. 12C illustrates a monitoring device 1220 using magnetic sensing, in accordance with embodiments. The device 1220 includes a magnetic sensor 1222 (e.g., a Hall Effect sensor or a magnetoresistive sensor) integrated into a first intraoral appliance 1224 worn on a patient's jaw (e.g., upper or lower jaw). The magnetic sensor 1222 is used to detect a magnetic field generated by a magnet 1226 integrated into a second intraoral appliance 1228 worn on the opposing jaw. In some embodiments, the characteristics of the magnetic field vary based on whether the first appliance 1224 and second appliance 1228 are being worn on the patient's teeth. The monitoring device 1220 can include a processor (not shown) configured to determine whether the appliances are being worn based on the sensing data produced by the magnetic sensors 1222.

A magnetic sensing-based monitoring device may include a ferromagnetic target (e.g., a metal plate) that alters the characteristics of the magnetic field when the appliance is worn. The ferromagnetic target can be integrated into an intraoral appliance or an attachment device mounted on a tooth, or can be an existing element in the intraoral cavity (e.g., a metal filling, implant, etc.). The monitoring device can detect whether the patient is using the appliance by sensing the characteristics of the magnetic field and detecting whether the ferromagnetic target is present.

Figure 13A:
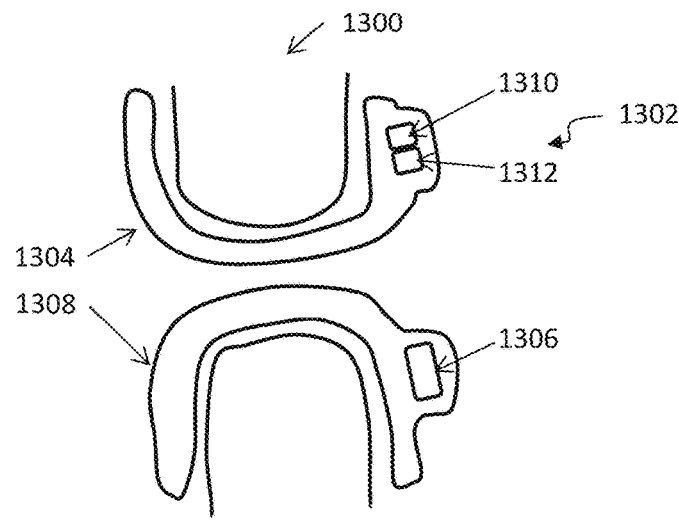
FIG. 13A illustrates an example of a monitoring device using magnetic sensing.

FIG. 13A illustrates a monitoring device 1300 using magnetic sensing, in accordance with embodiments. The monitoring device 1300 includes a sensing subunit 1302 integrated into a first intraoral appliance 1304 worn on a patient's jaw (e.g., upper or lower jaw) and a ferromagnetic target 1306 (e.g., a metal plate) integrated into a second intraoral appliance 1308 worn on the opposing jaw. The sensing subunit 1302 can include a magnet 1310 and a magnetic sensor 1312 that detect the magnetic field generated by the magnet 1310. In some embodiments, when the first appliance 1304 and second appliance 1308 are worn by the patient, the presence of the ferromagnetic target 1306 alters the characteristics of the generated magnetic field. The monitoring device 1300 can include a processor (not shown) configured to determine whether the appliances are being worn based on the sensing data produced by the magnetic sensor 1312.

Figure 13B:
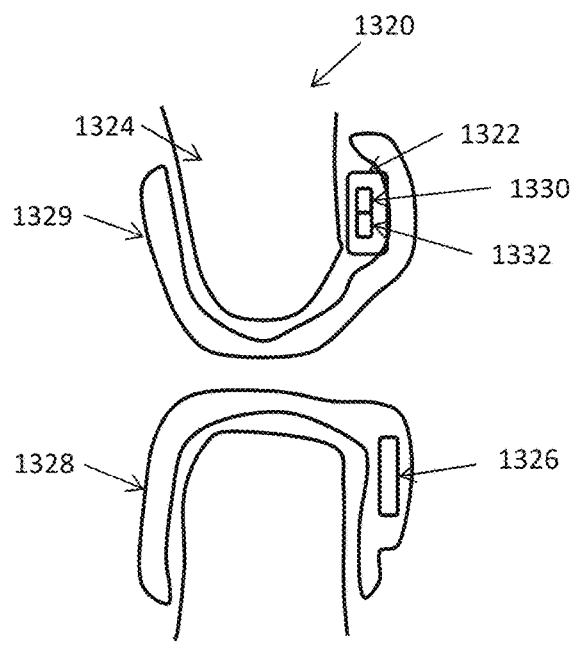
FIG. 13B illustrates an example of a monitoring device using magnetic sensing.

FIG. 13B illustrates a monitoring device 1320 using magnetic sensing, in accordance with embodiments. The monitoring device 1320 includes a sensing subunit 1322 integrated into an attachment device coupled to a tooth 1324 in a patient's jaw (e.g., upper or lower jaw) and a ferromagnetic target 1326 (e.g., a metal plate) integrated into an intraoral appliance 1328 worn on the opposing jaw. Optionally, a second intraoral appliance 1329 including a cavity shaped to receive the tooth 1324 and sensing subunit 1322 can also be worn. The sensing subunit 1322 can include a magnet 1330 and a magnetic sensor 1332 that detects the magnetic field generated by the magnet 1330. In some embodiments, when the appliance 1328 is worn by the patient, the presence of the ferromagnetic target 1326 alters the characteristics of the generated magnetic field. The monitoring device 1320 can include a processor (not shown) configured to determine whether the appliance 1328 is being worn based on the sensing data produced by the magnetic sensor 1332. Optionally, the processor and other components of the monitoring device 1320 can also be integrated into the attachment device. This implementation can reduce the costs of the device 1320, since only the relatively low cost ferromagnetic target would be replaced with each new appliance.

Figure 13C:
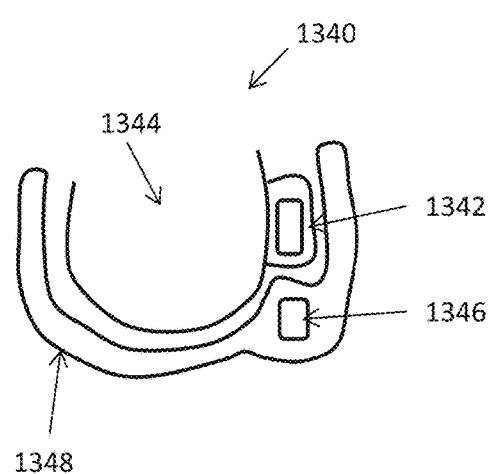
FIG. 13C shows an example of a monitoring device using magnetic sensing.

FIG. 13C illustrates a monitoring device 1340 using magnetic sensing, in accordance with embodiments. The monitoring device 1340 includes a sensing subunit 1342 integrated into an attachment device coupled to a tooth 1344 in a patient's jaw (e.g., upper or lower jaw) and a ferromagnetic target 1346 (e.g., a metal plate) integrated into an intraoral appliance 1348 worn on the same jaw. The appliance 1348 can include a cavity shaped to receive the tooth 1344 and the sensing subunit 1342. The sensing subunit 1342 can include a magnet and a magnetic sensor that detects the magnetic field generated by the magnet. In some embodiments, when the appliance 1348 is worn by the patient, the presence of the ferromagnetic target 1346 alters the characteristics of the generated magnetic field. The monitoring device 1340 can include a processor (not shown) configured to determine whether the appliance 1348 is being worn based on the sensing data produced by the magnetic sensor. Optionally, the processor and other components of the monitoring device 1340 can also be integrated into the attachment device, thus reducing cost when multiple appliances are used.

Alternatively or in combination, a monitoring device can use a magnet to directly activate a magnetic sensor. For example, a magnet can be attached to an intraoral tissue, such as a tooth surface. The monitoring device can include a magnetic sensor (e.g., a magnetic reed sensor or switch) integrated into an intraoral appliance such that when the appliance is worn, the magnet activates the sensor. In alternative embodiments, the locations of the magnet and magnetic sensor can be switched, such that the magnetic sensor is attached to the intraoral tissue and the magnet is integrated into the appliance. Optionally, the magnet can be integrated into a first intraoral appliance worn on a patient's jaw (e.g., upper or lower jaw) and the magnetic sensor can be integrated into a second intraoral appliance worn on the opposing jaw, such that when both appliances are worn, the magnet activates the sensor.

Alternatively or in combination, a monitoring device can utilize two or more magnets that interact with each other (e.g., by exerting magnetic forces on each other), and a sensor that detects the interaction between the magnets. For example, the sensor can be a mechanical switch coupled to a magnet and actuated by magnetic forces exerted on the magnet. As another example, the sensor can be configured to detect the characteristics (e.g., magnitude, direction) of the magnetic force exerted on a magnet by the other magnets. The magnets and sensor can each be independently integrated in an appliance or coupled to a tooth or other intraoral tissue.

FIGS. 14A and 14B illustrate a monitoring device 1400 using a plurality of magnets, in accordance with embodiments. The device 1400 includes a sensing subunit 1402 integrated into a first intraoral appliance 1404 worn on a patient's jaw (e.g., upper or lower jaw). The sensing subunit includes a first magnet 1406 coupled to a force sensor 1408. A second magnet 1410 is integrated into a second intraoral appliance 1412 worn on the opposing jaw. The force sensor 1408 can measure the magnetic force between the first magnet 1406 and the second magnet 1410, which varies according to the distance between the magnets. The monitoring device 1400 can include a processor (not shown) configured to determine whether the appliances are being worn based on the measured force. In some embodiments, the magnetic force can also be used to generate power for monitoring device 1400.

Alternatively or in combination, the monitoring devices of the present disclosure can include one or more force and/or pressure sensors for detecting appliance usage. For example, the monitoring device can include a force- and/or pressure-dependent resistive material, such as a film or sheet. The resistive material can be positioned between two thin electrodes in an intraoral appliance, and the resistance of the material may increase or decrease as force and/or pressure is exerted on the material, e.g., by the interaction between the teeth and the appliance. Other types of force and/or pressure sensors include strain gauges and piezocrystal sensors. In some embodiments, the monitoring device determines whether the patient is wearing the appliance based on the force and/or pressure measurements obtained by the force and/or pressure sensors. The measurement data may be indicative of the force and/or pressure between the appliance and an intraoral tissue, such as one or more of the patient's teeth. Optionally, the measurement data can be based on the force and/or pressure between the appliance and one or more attachment devices mounted on the patient's teeth. The monitoring device can process the data to determine whether the measured force and/or pressure are within the expected range corresponding to the patient wearing the appliance.

A monitoring device can include a single force and/or pressure sensor, or a plurality of force and/or pressure sensors. The sensors can be positioned at any location in the appliance, such on an inner surface, an outer surface, a buccal surface, a lingual surface, an occlusal surface, a mesial portion, a distal portion, a gingival portion, or a combination thereof. In some embodiments, the sensors are positioned to be near certain teeth when the appliance is worn. In embodiments where the appliance is an orthodontic appliance, the sensors can be positioned near teeth to be repositioned, e.g., at locations where the appliance is expected to exert force on the teeth. For example, if the appliance is shaped to engage an attachment device mounted on a tooth in order to exert force onto the tooth, a force and/or pressure sensor can be located at or near the location of engagement between the appliance and the attachment device.

FIG. 15 illustrates a monitoring device 1500 configured to measure force and/or pressure between an intraoral appliance 1502 and the patient's teeth, in accordance with embodiments. The device 1500 includes a plurality of pressure and/or force sensors 1504 (e.g., pressure-dependent resistive films) electrically coupled (e.g., via printed wires 1505 or other connecting elements) to a controller 1506. The plurality of pressure and/or force sensors 1504 can be patterned on the inner surface of the appliance 1502 so as to generate sensor data indicative of the pressure and/or force between the appliance 1502 and the patient's teeth. In some embodiments, the appliance 1502 includes a plurality of teeth receiving cavities and the pressure and/or force sensors 1504 are located on the buccal, lingual, and/or occlusal surfaces of the cavities. The controller 1506 can include components (e.g., as previously described with respect to FIG. 3) configured to process the sensor data to determine whether the appliance 1502 is being worn. Optionally, the controller 1506 can include a wireless antenna 1508 for transmitting the sensing data and/or processing results to a remote device, as described herein.

Figure 16A:
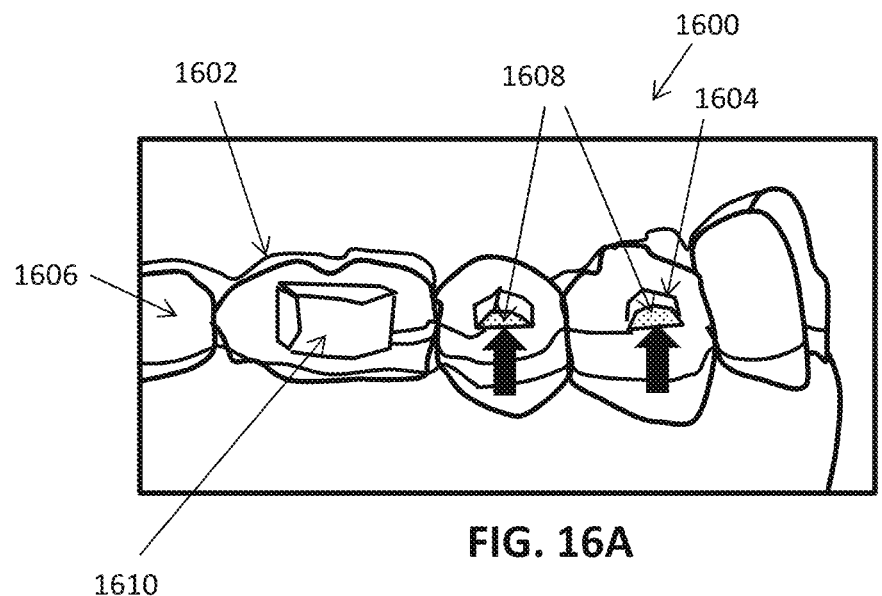
FIG. 16A illustrates an example of a monitoring device configured to measure force and/or pressure between an intraoral appliance and one or more attachment devices on a patient's teeth.
Figure 16B:
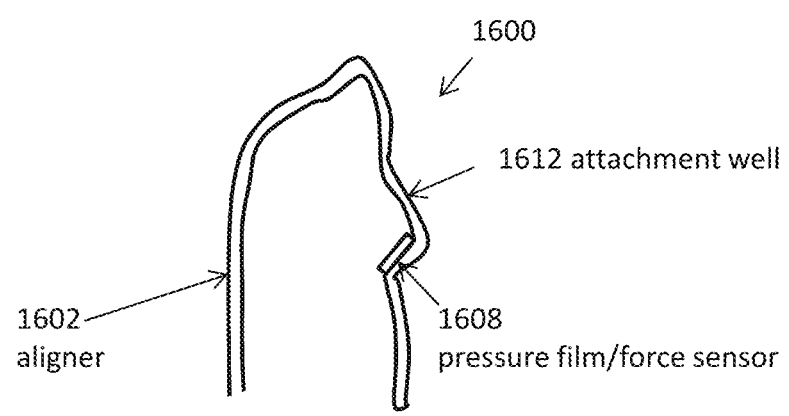
FIG. 16B is a cross-sectional view of the device of FIG. 16A.

FIGS. 16A and 16B illustrate a monitoring device 1600 configured to measure force and/or pressure between an intraoral appliance 1602 and one or more attachment devices 1604 on a patient's teeth 1606, in accordance with embodiments. The device 1600 includes a plurality of pressure and/or force sensors 1608 (e.g., pressure-dependent resistive films) electrically coupled to a controller 1610. The plurality of pressure and/or force sensors 1608 can be patterned on the inner surface of the appliance 1602 so as to generate sensor data indicative of the pressure and/or force between the appliance 1602 and the attachment devices 1604 on the patient's teeth 1606. In some embodiments, the appliance 1602 includes a plurality of teeth receiving cavities formed with one or more receptacles 1612 to receive the corresponding attachment devices 1604 on the patient's teeth, and the pressure and/or force sensors 1608 can be positioned the inner surface of one or more receptacles 1612. The controller 1610 can include components (e.g., as previously described with respect to FIG. 3A) configured to process the sensor data to determine whether the appliance 1602 is being worn.

Any of the apparatuses (e.g., monitoring devices) described herein may be configured to determine mechanical impedance of the teeth and/or intraoral appliance. For example, any of the apparatuses described herein may be configured to derive a mechanical impedance of a tooth, multiple or groups of teeth, and/or the appliance. Generally, mechanical impedance may be referred to as the resistance to motion given an applied force:

$$Z(w)=F(w)/v(w)$$

Where F=force, v=velocity and w=angular frequency.

Figure 16C:
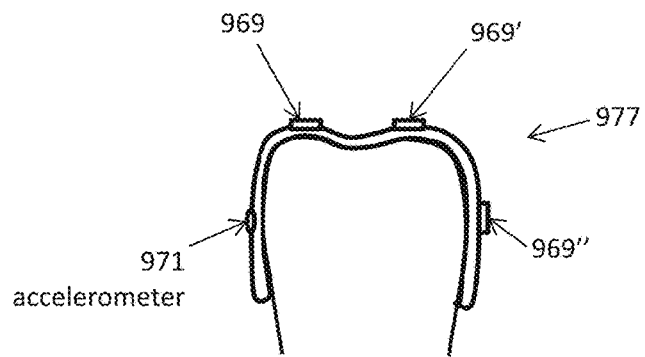
FIG. 16C is an example of an intraoral device configured to measure mechanical impedance of a tooth or teeth.

FIG. 16C illustrates one example of a section through an intraoral appliance 977 (showing in this example as an aligner) including a motion sensor 971 (such as an accelerometer) and one or more force sensors 969, 969', 969". Alternatively or additionally, one or more of the motion sensor and force sensor(s) may be positioned directly on the teeth (including on an attachment adapted to secure the intraoral appliance to the teeth) and may communicate with a processor/analysis engine, battery, communications circuitry, etc. on the aligner.

Figure 16D:
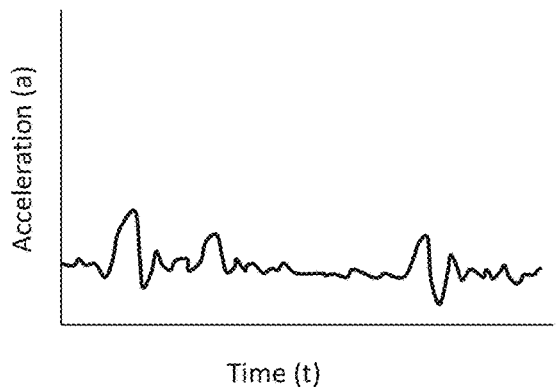
FIG. 16D graphically illustrates the detection of acceleration over time at a particular tooth (or an aligner portion corresponding to a particular tooth).
Figure 16E:
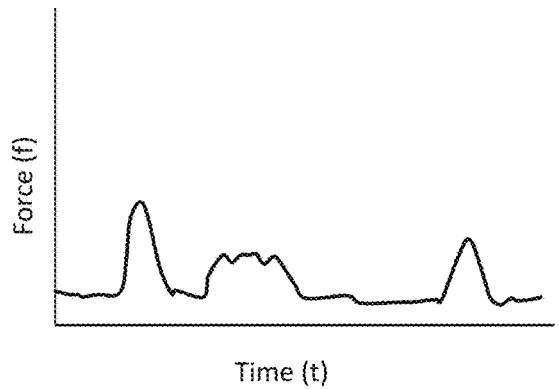
FIG. 16E graphically illustrates the detection of force over time at the same tooth (or aligner region) for which acceleration was determined as shown in FIG. 16D. An intraoral device configured to measure mechanical impedance such as the apparatus shown in FIG. 16C may correlate the acceleration over time and the force over time to estimate mechanical impedance for the tooth.

The processor/analysis engine may then use the motion (e.g., acceleration) data over time, an example of which is shown in FIG. 16D, and corresponding force data over time, an example of which is shown in FIG. 16E, and may correlate this data to estimate mechanical impedance.

Alternatively of additionally, the system may estimate mechanical impedance based on underdamped second order system (e.g., as a logarithmic decrement of an underdamped second order system). In this case, the apparatus may be configured to measure the teeth (and/or appliance) response to a perturbing force, such as an input vibration or force applied to the teeth. For example, the apparatus may be configured to measure the free vibration response to a mechanical impulse input. The apparatus may then determine the peak-to-peak decay of the underdamped oscillation and the period of the system; from these values, the apparatus may then derive the damped natural frequency, the natural frequency, and a damping ratio. In a second order system, these values may define the impedance.

For linear systems, the apparatus may fit parameter of a parametric model of the mechanical impedance to a measured bode plot. For non-linear system, the apparatus may use generalized frequency response functions to analyze non-linear systems (e.g., forced vibrations response, sinusoidal frequency sweeps, etc., including machine learning).

Figure 16F:
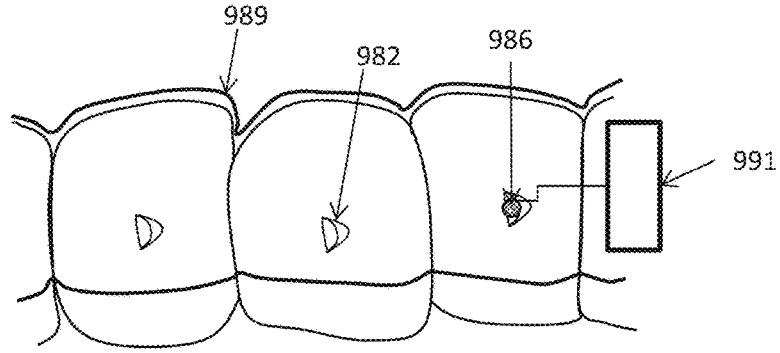
FIG. 16F shows a portion of an intraoral appliance configured to measure mechanical impedance. In this example, one or more motion sensors (e.g., accelerometers) may be coupled to the tooth (as part of the attachment, as shown) and may communicate with electronic components on the intraoral appliance (e.g., memory, processor, power supply, wireless communications, etc.). The apparatus may also include or may be used in conjunction with a mechanical actuator to provide a known (or measured) perturbing vibration, and the processor may use the known force input with the output from the accelerometer to determine mechanical impedance for the tooth/teeth.
Figure 20A:
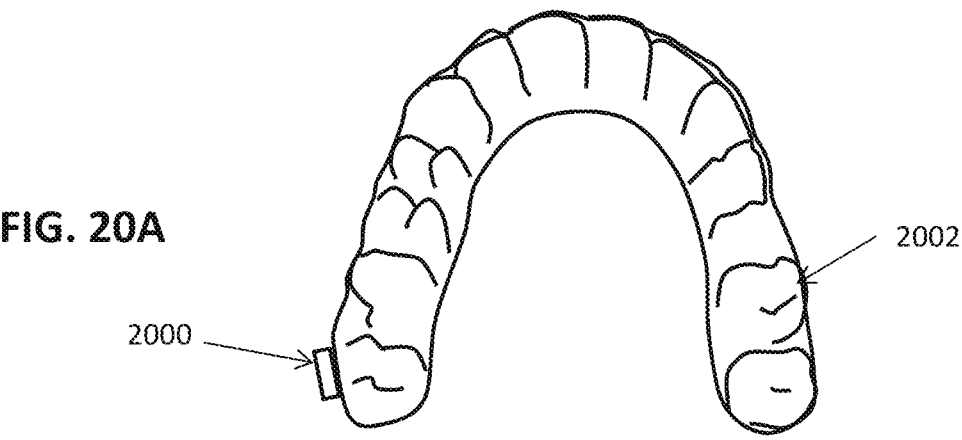
FIGS. 20A through 20D illustrate an exemplary method for fabricating an intraoral appliance with an integrated monitoring device.
Figure 20B:
Figure 20C:
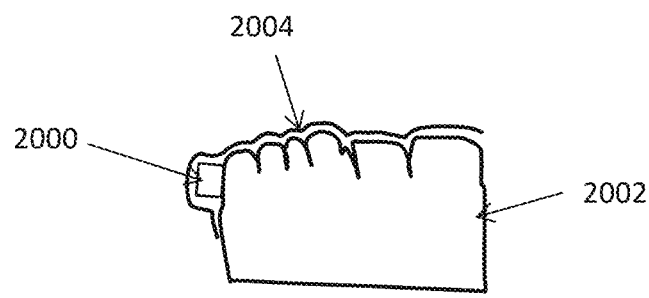
Figure 20D:
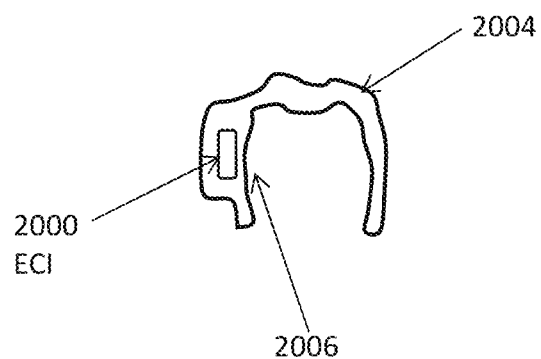

For example, FIG. 16F shows a side view of another example of an apparatus for measuring mechanical impedance of a tooth or teeth. In this example, a plurality of attachments 982 are used to secure an orthodontic appliance (e.g., aligner 989) to the teeth. The aligner includes a processor 991, wireless communication circuitry, and may include additional hardware, software and/or firmware for detecting sensor data to determine mechanical impedance of the teeth and/or aligner. The attachments may include one or more sensors, including motion (e.g., accelerometers) and/or force sensors; these one or more sensors may communicate directly (e.g., via electrical contact) with the processor 991 on the aligner.

In FIG. 16F, this configuration may be used as described above, and/or may be used to determine a frequency response to an applied input signal. For example, any of these apparatuses may include an actuator to apply a vibration or force input to the teeth (e.g., a vibration motor, miniature piston, etc.). The force applied by the actuator may be measured or estimated and used in conjunction with the detected response (e.g., motion/acceleration data). Alternatively, the apparatus my take into account naturally occurring force inputs (e.g., masticatory forces), and may measure or estimate them; as mentioned above, using one or more force sensors. The force data as well as the response movement/acceleration data may be used to determine mechanical impedance.

The resulting mechanical impedance data may then be used to assess the health of the tooth movement.

Figure 17A:
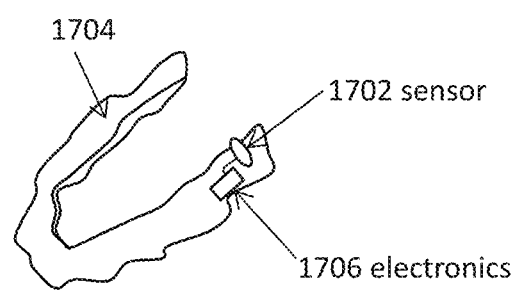
FIG. 17A shows an example of a monitoring device including a gas flow sensor.

Alternatively or in combination, the monitoring devices described herein can include one or more gas flow sensors configured to detect whether the intraoral appliance is being worn based on intraoral airflow. For instance, the gas flow sensor can be a hot-wire anemometer configured to measure airflow associated with breathing, mastication, speech, snoring, and the like. The embodiments herein can also incorporate microfluidic-based gas flow sensors, as desired. Optionally, gas flow sensors can also be used to measure airflow to determine whether the patient is experiencing a sleep apnea event. For example, the monitoring device can determine whether the measured airflow pattern is similar to airflow patterns that occur when the patient is experiencing sleep apnea. This approach can be used in embodiments where the intraoral appliance is a sleep apnea treatment appliance (e.g., a mandibular advancement device), for example. FIG. 17A illustrates a monitoring device 1700 including a gas flow sensor 1702, in accordance with embodiments. The sensor 1702 is integrated into an intraoral appliance 1704. In some embodiments, the sensing portion of the sensor 1702 (e.g., a wire or conductor) extends from the appliance 1704 (e.g., a lingual surface) so as to be exposed to intraoral airflow. The sensing data obtained by the sensor 1702 can be processed and analyzed by other components of the monitoring device 1700 (e.g., controller 1706) in order to determine appliance usage and/or whether patient is experiencing a sleep apnea event.

FIG. 17B illustrates a monitoring device 1720 including a gas flow sensor 1722, in accordance with embodiments. The device 1720 can be substantially similar to the device 1700, except that the sensor 1722 extends across the opposite sides of the appliance 1724 such that the sensing portion is located near the middle of the intraoral airflow. This approach may provide improved sensing accuracy.

FIG. 17C illustrates a monitoring device 1740 including a gas flow sensor 1742, in accordance with embodiments. The device 1740 can be substantially similar to the device 1720, except that the sensor 1742 extends only from one side of appliance 1744. This approach may reduce patient discomfort.

Alternatively or in combination, a monitoring device can include one or more motion sensors configured to detect appliance usage based on movements of one or both of the patient's jaws. Examples of such motion sensors include accelerometers, gyroscopes, piezoelectric film vibration sensors, gravity sensors, and microwave emitters and receivers. The motion sensors can be integrated into an intraoral appliance worn on a patient's upper or lower jaw, or can be distributed across an appliance worn on the upper jaw and an appliance worn on the lower jaw. In some embodiments, the motion sensors are configured to generate data representative of the patient's jaw movement patterns, and the monitoring device processes and analyzes the movement patterns (e.g., using power spectrum and/or kinematic analysis) to determine whether the patterns indicate that the appliance(s) are being worn. Optionally, the monitoring device can distinguish jaw movement patterns associated with different oral activities (e.g., mastication, grinding, speech, etc.).

FIG. 18 illustrates a monitoring device 1800 using motion sensing, in accordance with embodiments. The device 1800 includes one or more motion sensors 1802 integrated into a first intraoral appliance 1804 worn on a patient's jaw (e.g., upper or lower jaw). In some embodiments, the motion sensors 1802 include one or more magnetometers that detect the magnetic field generated by a magnet 1806 integrated into a second intraoral appliance 1808 worn on the opposing jaw. For instance, the device 1800 can include two multi-axis magnetometers used to obtain a six-axis measurement of the relative movements of the upper and lower jaws. In alternative embodiments, rather than using the magnet 1806, the magnetometer(s) 1802 can be used to measure the angle of the patient's jaw relative to the earth's magnetic field, and the angle data can be used to determine whether the appliance is being worn. The motion data generated by the motion sensor(s) 1802 can be used to track jaw movement patterns in order to determine whether the appliances are currently being worn. Other types of motion sensors 1802 can also be used, such as accelerometers, gravity sensors, gyroscopes, or microwave emitters and receivers.

Alternatively or in combination, a monitoring device can include one or more temperature sensors, such as sensors detecting temperature based on infrared radiation, conductive thermistor-based sensors, and the like. The motion detector can determine appliance usage based on whether the measured temperature is within the range of body temperature, e.g., oral cavity temperature. Optionally, this determination can involve comparing the measured temperature with ambient temperature measurements obtained while the appliance is not being worn. In some embodiments, the temperature data is recorded as the raw temperature value. Alternatively, the temperature data can be recorded in binary form (e.g., whether the temperature is within the range of body temperature or not), for example, to save memory space.

Alternatively or in combination, a monitoring device can include one or more strain gauges (e.g., resistive or MEMS-based) to detect the stress and/or strain at one or more locations in the intraoral appliance. The monitoring device can determine whether the measured stress and/or strain values are within the expected ranges for appliance usage. The monitoring device can store the actual stress and/or strain values, or can store just binary data indicating whether or not the appliance is being worn.

Alternatively or in combination, a monitoring device can include one or more pH sensors configured to measure the pH values of fluids (e.g., saliva) in the surrounding environment. The monitoring device can determine whether the appliance is being worn based on whether the measured pH values are within the expected pH range for human saliva, for example.

Alternatively or in combination, a monitoring device can include one or more conductivity sensors configured to measure the conductivity of fluids (e.g., saliva) in the surrounding environment. The monitoring device can determine whether the appliance is being worn based on whether the measured conductivity is within the expected range for human saliva, for example. In some embodiments, the conductivity can be measured over a period of time. This approach can be used to prevent the monitoring device from being deceived by immersion into saliva-mimicking fluids, since the conductivity of human saliva may vary over time based on the body's physiological activities.

Alternatively or in combination, a monitoring device can include one or more humidity sensors configured to detect contact with intraoral fluids (e.g., saliva). The monitoring device can determine whether the appliance is being worn based on whether the measured humidity is within the expected humidity range for the intraoral cavity, for example.

The monitoring devices described herein may be used to measure health information for the patient alternatively to or in combination with detecting appliance usage. Such monitoring devices can include one or more physiological sensors, such as electrocardiography sensors, bio-impedance sensors, photoplethysmography sensors, galvanic skin response sensors, or combinations thereof. For example, a photoplethysmography sensor can be used to measure blood volume changes in the patient's intraoral tissues such as the cheeks or gingiva. As another example, a galvanic skin response sensor can be used to measure the conductivity of intraoral tissues, which may vary based on the minerals released onto the outer tissue surfaces from glands, for example. In some embodiments, the monitoring devices described herein are configured to differentiate between sensor data indicative of appliance usage and sensor data produced by other types of patient interactions with the appliance (e.g., the appliance being held in a patient's hand). Such differentiation can be accomplished by training the monitoring device to distinguish between data patterns indicative of appliance usage and data patterns produced by other interactions, e.g., based on a training data set prior to actual patient monitoring and/or data generated during monitoring. Alternatively or in combination, this differentiation can be performed by other devices besides the monitoring device, e.g., by an external processor performing post-processing on the data obtained by the monitoring device.

FIG. 19 illustrates a method 1900 for monitoring usage of an intraoral appliance, in accordance with embodiments. The method 1900 can be performed using any embodiment of the systems and devices described herein. In some embodiments, some or all of the steps are performed using a processor of a monitoring device operably coupled to an intraoral appliance. Alternatively or in combination, some or all of the steps can be performed by a processor of a device external to the patient's intraoral cavity, e.g., a separate computing device or system.

In step 1910, sensor data is received from one or more sensors operably coupled to an intraoral appliance. The one or more sensors can include any of the sensor types described herein, including but not limited to touch or tactile sensors (e.g., capacitive, resistive), proximity sensors, audio sensors (e.g., microelectromechanical system (MEMS) microphones), color sensors (e.g., RGB color sensors), electromagnetic sensors (e.g., magnetic reed sensors, magnetometer), light sensors, force sensors (e.g., force-dependent resistive materials), pressure sensors, temperature sensors, motion sensors (e.g., accelerometers, gyroscopes), vibration sensors, piezoelectric sensors, strain gauges, pH sensors, conductivity sensors, gas flow sensors, gas detection sensors, humidity or moisture sensors, physiological sensors (e.g., electrocardiography sensors, bio-impedance sensors, photoplethysmography sensors, galvanic skin response sensors), or combinations thereof. The sensor(s) can be physically integrated with (e.g., coupled to, embedded in, formed with, etc.) the intraoral appliance, or can be positioned in the intraoral cavity (e.g., attached to a tooth) so as to interact with the intraoral appliance. The sensor data can be indicative of whether the appliance is currently being worn in the patient's mouth, in accordance with the embodiments described herein.

In step 1920, the sensor data is processed to determine whether the appliance is being worn. For example, the processing step can involve determining whether the sensor data matches a pattern and/or falls within a range of values indicating that the appliance is being worn. Alternatively or in combination, the processing step can involve determine whether the sensor data is different from a pattern and/or lies outside a range of values indicating that the appliance is not being worn. Optionally, the processing step can involve associating the sensor data with a timestamp representing when the data was obtained such that temporal appliance usage information can be determined. The processed sensor data can include appliance usage information indicating whether the appliance is currently being worn, the duration of appliance usage, and/or the date-time the appliance was in use. In some embodiments, step 1920 can alternatively or additionally involve processing the sensor data to determine patient health information, as discussed herein.

In step 1930, the sensor data generated in step 1910 and/or processed sensor data generated in step 1920 is optionally transmitted to a remote device. The remote device can be a mobile device (e.g., smartphone), personal computer, laptop, tablet, wearable device, cloud computing server, or the like. Step 1930 can be performed using wireless or wired communication methods, as desired. Step 1930 can be performed automatically (e.g., at predetermined time intervals) or in response to instructions received from the remote device (e.g., a command to transmit the sensor data and/or appliance usage).

The monitoring devices described herein can be physically integrated into an intraoral appliance in a variety of ways. In some embodiments, the monitoring device is integrated into the appliance during or after fabrication of the appliance. For example, the monitoring device can be attached to an appliance using adhesives, fasteners, a latching mechanism, or a combination thereof after the appliance has been fabricated. Optionally, the appliance can be formed with complementary features or structures (e.g., recesses, receptacles, guides, apertures, etc.) shaped to receive and accommodate the monitoring device or components thereof.

In some embodiments, a monitoring device is coupled to the appliance as a prefabricated unit during or after fabrication of the appliance, such as by being inserted and sealed into a receptacle in the appliance, attached to an appliance (e.g., by a latching mechanism, adhesive, fastener). Alternatively, the monitoring device can be assembled in situ on the appliance during or after appliance fabrication. For instance, in embodiments where the appliance is manufactured by direct fabrication (e.g., 3D printing), the monitoring device can be printed simultaneously with the appliance, inserted into the appliance during fabrication, or after assembled the appliance has been fabricated. Optionally, some of the monitoring device components may be prefabricated and other components may be assembled in situ. It shall be appreciated that the various fabrication methods described herein can be combined in various ways in order to produce an appliance with integrated monitoring device components.

FIGS. 20A through 20D illustrate a method for fabricating an intraoral appliance with an integrated monitoring device, in accordance with embodiments. The method can be applied to any embodiment of the monitoring devices and appliances described herein, and can be used in combination with any of the other fabrication methods described herein. In a first step (FIGS. 20A (top view) and 20B (side view)), a prefabricated monitoring device 2000 is coupled to a positive model 2002 of a patient's dentition. The monitoring device 2000 can be attached using an adhesive and/or a mechanical fastener, for example. Optionally, the monitoring device 2000 can be hermetically sealed prior to being attached to the model 2002. In a second step (FIG. 20C), a material is formed (e.g., thermoformed) over the monitoring device 2000 and model 2002 so as to produce an appliance shell 2004. In a third step (FIG. 20D), the mold 2002 is removed, resulting in an appliance shell 2004 with an embedded monitoring device 2000. Optionally, the monitoring device 2000 can be encapsulated using a biocompatible adhesive 2006 (e.g., a UV-curable glue), a layer of material, or other sealing element.

Figure 21A:
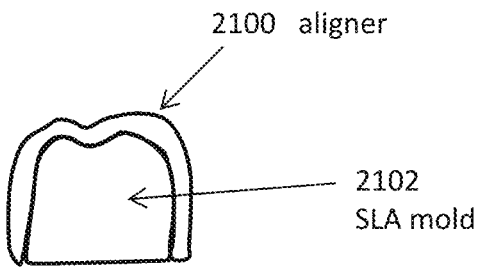
FIGS. 21A through 21C illustrate an example of a method for fabricating an intraoral appliance with an integrated monitoring device.
Figure 21B:
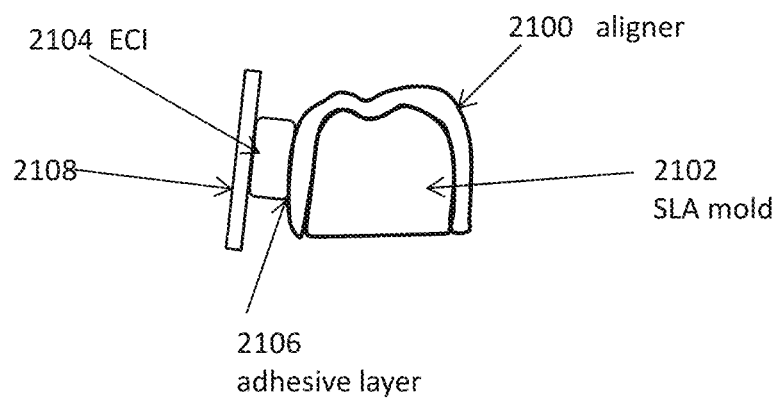
Figure 21C:
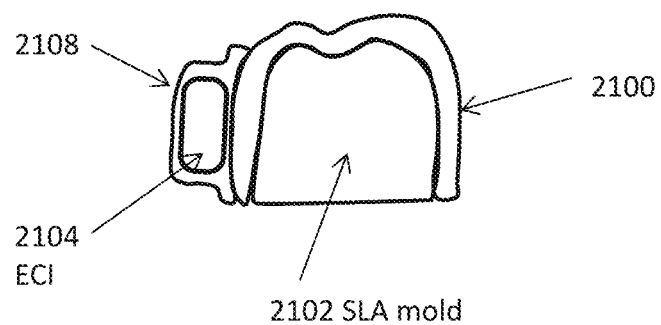

FIGS. 21A through 21C illustrate a method for fabricating an intraoral appliance with an integrated monitoring device, in accordance with embodiments. The method can be applied to any embodiment of the monitoring devices and appliances described herein, and can be used in combination with any of the other fabrication methods described herein. In a first step (FIG. 21A), an appliance 2100 is formed (e.g., thermoformed) over a positive model 2102 of a patient's dentition. In a second step (FIG. 21B), a prefabricated monitoring device 2104 is attached to the appliance 2100, e.g., using an adhesive layer 2106 and/or fastener, and a thermoplastic material 2108 is attached to the outer surface of the monitoring device 2104. In a third step (FIG. 21C), the thermoplastic material 2108 is thermoformed so as to form a cover encapsulating the monitoring device 2104 into the appliance 2100. The positive model 2102 can be removed e.g., before or after the third step.

Alternatively or in combination, the method can involve forming a positive geometry corresponding to the geometry of the monitoring device 2104 on the positive model 2102 (e.g., by 3D printing, CNC milling, etc.), such that the appliance 2100 is thermoformed with a receptacle for the monitoring device 2104. The monitoring device 2104 can then be placed and sealed into the receptacle.

Alternatively or in combination, an intraoral appliance with an integrated monitoring device can be produced by fabricating the appliance (e.g., by indirect or direct fabrication), then attaching a prefabricated monitoring device to the fabricated appliance, e.g., using adhesives, fasteners, a latching mechanism, etc. Optionally, the monitoring device can be hermetically sealed (e.g., by molding) before being attached to the appliance.

Alternatively or in combination, an intraoral appliance with an integrated monitoring device can be fabricated by coupling flexible and/or printed components of a monitoring device onto the appliance during or after forming the appliance. The components can be coupled in various ways, such as thermoforming, laminating, adhesives, coating, and so on.

Alternatively or in combination, an intraoral appliance with an integrated monitoring device can be fabricated by 3D printing a base for the monitoring device, then building up the electronic components for the monitoring device onto the base. In some embodiments, the base is shaped to conform to the geometry of the tooth receiving cavity and/or target tooth where the monitoring device will be located. The 3D printed portions of the monitoring device can be shaped to lie flush with the surface of the appliance to facilitate integration of the monitoring device with the appliance. Alternatively or in combination, an intraoral appliance with an integrated monitoring device can be fabricated by etching the surface of the appliance (e.g., using a masking process) and then depositing conductive inks, stretchable materials, etc. onto the etched portions to build up the electronic components of the monitoring device (e.g., wires, connections, electrodes, etc.) on the appliance.

Figure 22:
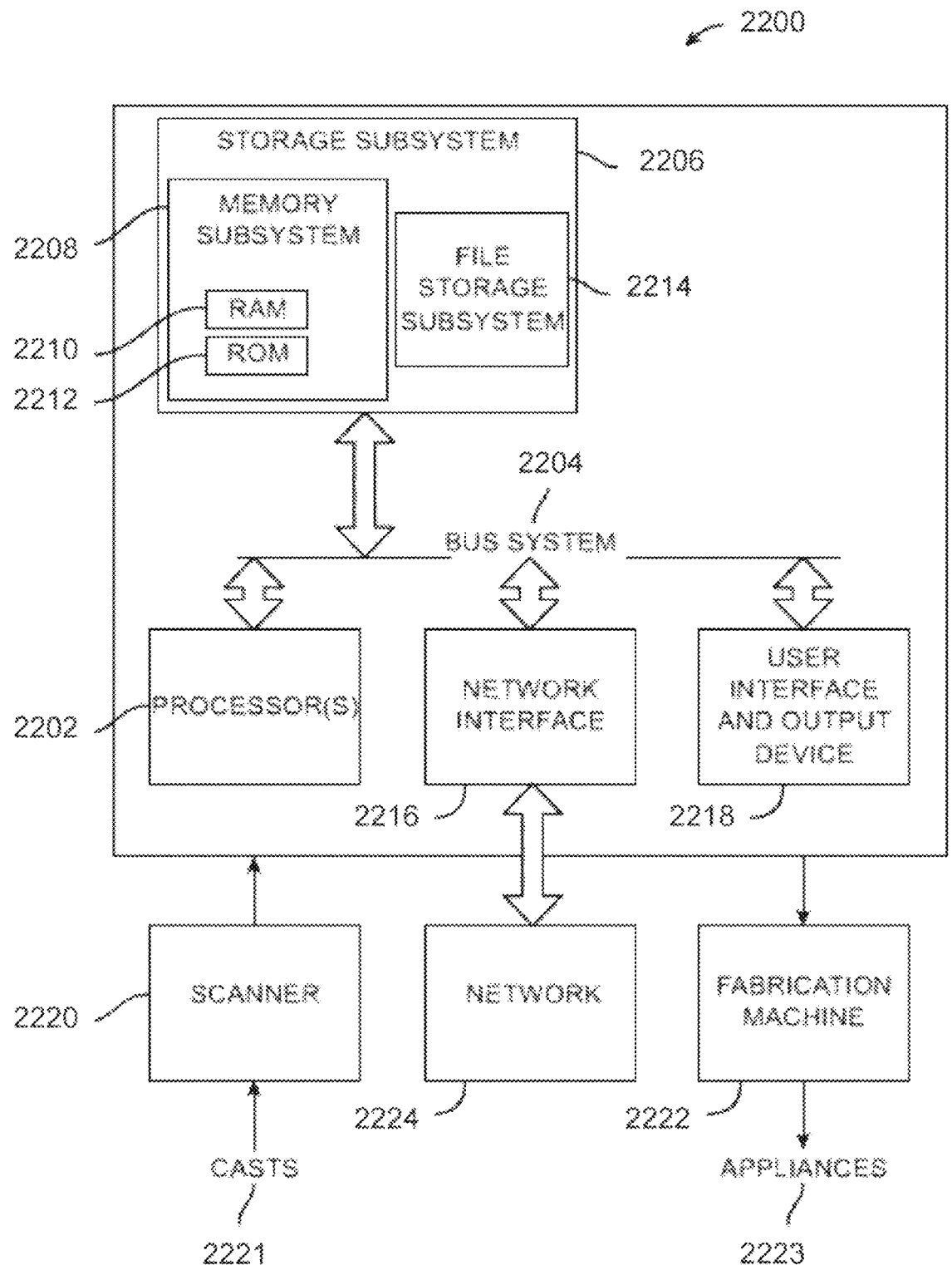
FIG. 22 is a simplified block diagram of an example of a data processing system.

FIG. 22 is a simplified block diagram of a data processing system 2200 that may be used in executing methods and processes described herein. The data processing system 2200 typically includes at least one processor 2202 that communicates with one or more peripheral devices via bus subsystem 2204. These peripheral devices typically include a storage subsystem 2206 (memory subsystem 2208 and file storage subsystem 2214), a set of user interface input and output devices 2218, and an interface to outside networks 2216. This interface is shown schematically as "Network Interface" block 2216, and is coupled to corresponding interface devices in other data processing systems via communication network interface 2224. Data processing system 2200 can include, for example, one or more computers, such as a personal computer, workstation, mainframe, laptop, and the like.

The user interface input devices 2218 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 2206 maintains the basic required programming, including computer readable media having instructions (e.g., operating instructions, etc.), and data constructs. The program modules discussed herein are typically stored in storage subsystem 2206. Storage subsystem 2206 typically includes memory subsystem 2208 and file storage subsystem 2214. Memory subsystem 2208 typically includes a number of memories (e.g., RAM 2210, ROM 2212, etc.) including computer readable memory for storage of fixed instructions, instructions and data during program execution, basic input/output system, etc. File storage subsystem 2214 provides persistent (non-volatile) storage for program and data files, and can include one or more removable or fixed drives or media, hard disk, floppy disk, CD-ROM, DVD, optical drives, and the like. One or more of the storage systems, drives, etc. may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 2220 includes any means for obtaining a digital representation (e.g., images, surface topography data, etc.) of a patient's teeth (e.g., by scanning physical models of the teeth such as casts 2221, by scanning impressions taken of the teeth, or by directly scanning the intraoral cavity), which can be obtained either from the patient or from treating professional, such as an orthodontist, and includes means of providing the digital representation to data processing system 2200 for further processing. Scanner 2220 may be located at a location remote with respect to other components of the system and can communicate image data and/or information to data processing system 2200, for example, via a network interface 2224. Fabrication system 2222 fabricates appliances 2223 based on a treatment plan, including data set information received from data processing system 2200. Fabrication machine 2222 can, for example, be located at a remote location and receive data set information from data processing system 2200 via network interface 2224.

Appliances having teeth receiving cavities such as those disclosed herein include appliances that receive and reposition teeth, e.g., via application of force due to appliance resiliency. Examples of such appliances are generally illustrated with regard to FIG. 2A. FIG. 2A illustrates an exemplary tooth repositioning appliance or aligner 1000 that can be worn by a patient in order to achieve an incremental repositioning of individual teeth 1002 in the jaw. The appliance can include a shell having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some embodiments, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 1004 on teeth 1002 with corresponding receptacles or apertures 1006 in the appliance 1000 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

FIG. 2B illustrates a tooth repositioning system 1010 including a plurality of appliances 1012, 1014, 1016. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 1010 can include a first appliance 1012 corresponding to an initial tooth arrangement, one or more intermediate appliances 1014 corresponding to one or more intermediate arrangements, and a final appliance 1016 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

In some embodiments, orthodontic appliances, such as the appliance illustrated in FIG. 2A, impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space, and may comprise one or more of rotation or translation along one or more axes. Types of tooth movements include extrusion, intrusion, rotation, tipping, translation, and root movement, and combinations thereof, as discussed further herein. Tooth movement of the crown greater than the movement of the root can be referred to as tipping. Equivalent movement of the crown and root can be referred to as translation. Movement of the root greater than the crown can be referred to as root movement.

Other examples of dental appliances that may be configured as apparatuses for closed-loop (or semi-closed loop) modification of a treatment plan are shown in FIGS. 24A-27F. These apparatuses, as described above, may include one or more sensors that may detect interaction with the appliance itself, instead or in addition to monitoring the interaction the patient's oral cavity (e.g., teeth).

Figure 24A:
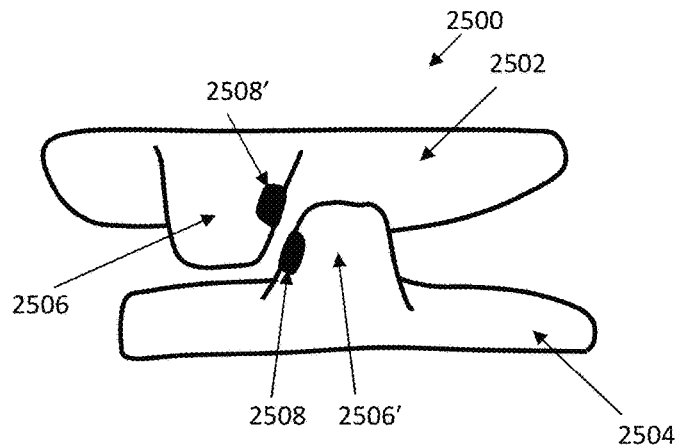
FIGS. 24A-24B illustrate one example of an orthodontic device comprising a mandibular repositioning device that may be used as part of a system for closed-loop (or semi-closed loop) modification of a treatment plan.
Figure 24B:
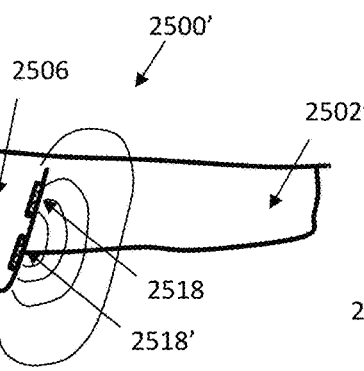

FIGS. 24A-24B illustrate one embodiment of an orthodontic apparatus as described herein comprising a mandibular repositioning appliance 2500. The mandibular repositioning appliance 2500 can comprise first and second intraoral appliances 2502, 2504 (which may be part of a shell aligner configured to secure to the teeth and/or may reposition them, and may be configured to receive the patient's upper and lower teeth, respectively. Each of the intraoral appliances may include a positioning feature 2506, 2506' that are configured to engage with each other. The interaction between the positioning features may drive the jaw (e.g., the patient's lower jaw) to provide orthodontic effect. At least one positioning feature in the apparatus may include at least one sensor 2508. In FIG. 24A, both the upper and lower positioning features include sensors. These sensors may detect contact and/or proximity between the opposite positioning features, and provide information on the proper functioning of the apparatus, e.g., engagement between the positioning features from the correct sides/locations. In FIG. 24A, the orthodontic apparatus can further include at least one processor and any of the additional components of the sensing sub-systems, as described in more detail above. Any of these sensors may also provide force data (or other sensor data) that may be compared to a predetermined treatment protocol as described above.

FIG. 24B is an alternative view of a first or upper appliance 2502' for an intraoral apparatus 2500', including a positioning feature 2506. The positioning feature can include a sensor 2508; in this example, the sensor includes two portions (e.g., a pair of electrodes 2518, 2518'). The sensor can be any type of sensor as described herein. For example, the sensor can be a capacitive sensor, a magnetic sensor, a force sensor, a push button sensor, a resistive sensor.

Referring back to FIG. 24A, the sensors of the first and second intraoral appliances can provide sensor data to the processor. The processor can be configured to use the sensor data to determine a state of the mandibular repositioning apparatus. For example, the sensor data can be used to determine if the positioning features of the first and second intraoral appliances are properly engaged. Sensors on the mating surfaces of the positioning features can detect contact between the upper and lower positioning features. More sophisticated sensors can detect distance between the positioning features, in addition to contact.

Figure 24C:
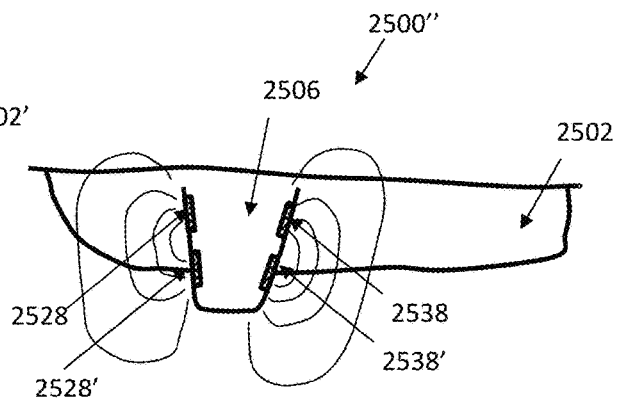
FIGS. 24C-24E show an example of a mandibular repositioning device that can detect both proper engagement and reverse engagement of positioning features, and may be used as part of a system for closed-loop (or semi-closed loop) modification of a treatment plan.
Figure 24D:
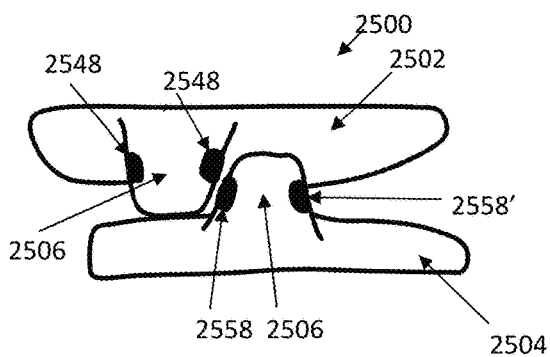
Figure 24E:
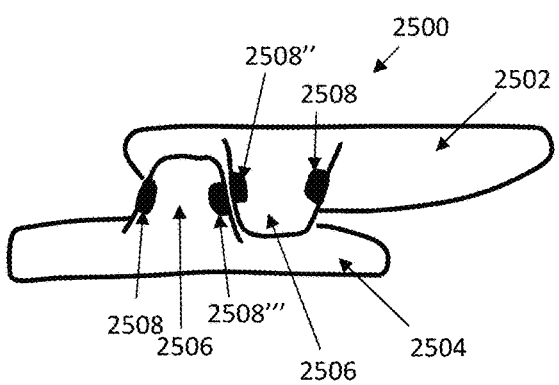

FIGS. 24C-24E show an example of a mandibular repositioning apparatus 2500" that can detect both proper engagement of positioning features, as described above (and shown in FIG. 24D), and reverse engagement, as shown in FIG. 24E. In the example of FIG. 24C sensors 2528, 2528', 2538, 2538' are positioned on opposite sides of the positioning features 2506. FIGS. 24D and 24E illustrate operation of a mandibular repositioning apparatus. In FIGS. 24D and 24E sensors 2548, 2548' and 2558, 2558' are located on either side of each positioning feature 2506, 2506'. The processor can then determine which of the sensors are in contact or in close proximity to determine if the mandibular repositioning device is properly engaged (FIG. 24D) or reverse engaged (FIG. 24E).

The sensors of the mandibular repositioning apparatus can further comprise additional sensors, such as sensors configured as compliance indicators (e.g., temperature sensors or accelerometers to give an indication of head position and whether the appliances are being worn, etc.). The processor(s) may be configured to use the additional compliance indicators to determine that engagement is being assessed only when the appliances are worn by the patient. The mandibular repositioning apparatus 2500 may therefore be configured to detect compliance and proper use by detecting engagement of the positioning features while the appliances are being worn by the patient.

Figure 25:
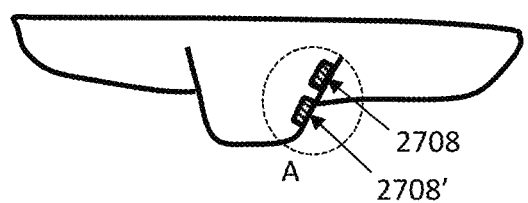
FIG. 25 is an example of portion of a mandibular repositioning apparatus including an engagement feature having a pair of sensors (e.g., capacitive sensors).
Figure 25A:
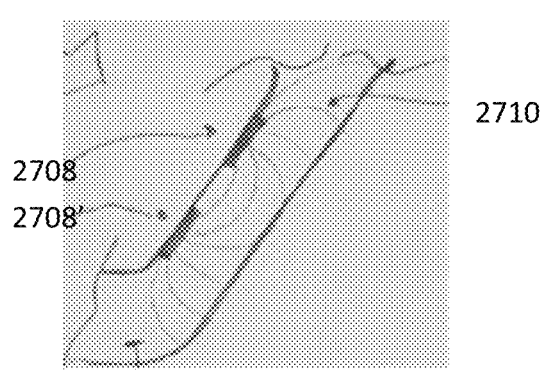
FIGS. 25A-25B illustrate operation of the sensors of the mandibular repositioning apparatus shown in FIG. 25 (enlarged) configured to assess device quality.
Figure 25B:
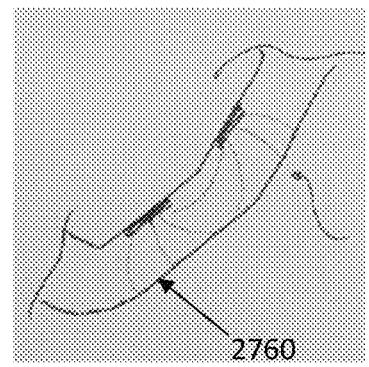

FIG. 25 illustrates another example of a portion of a mandibular repositioning apparatus, including a sensor (configured as a pair of electrodes 2708, 2708') that may be used as part of a system for closed-loop (or semi-closed loop) modification of a treatment plan. Referring to FIGS. 25A-25B, the sensor 2708, 2708' of an orthodontic apparatus can also be used to assess device quality (e.g., structural integrity, defects, etc.). For example, large unsupported thermoformed features, like the mandibular positioning features of FIGS. 24A-24E, may deform during treatment. Sensors (such as capacitive sensors) can be used to detect the deformation of the intraoral appliance. Referring to FIG. 25A, the appliance can include one or more capacitive sensors 2708, 2708' that sense static electric field lines 710. In FIG. 25B, the capacitive sensors are able to detect changes in the electric field that the processor may use to determine that the appliance is bent or deformed by sensing changes to the static electric field lines.

Figure 26:
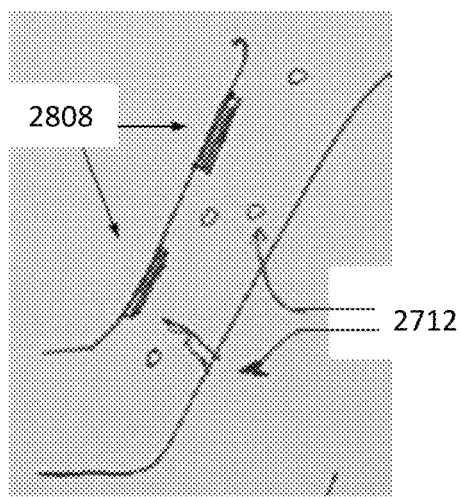
FIG. 26 illustrates a dental appliance with sensors that can detect defects in the appliance, which may also be used as part of a system for closed-loop (or semi-closed loop) modification of a treatment plan.

Additionally, the sensors can be used to detect defects within the appliance, such as air bubbles or cracks. Referring to FIG. 26, sensors 2808 in the appliance can detect the relative permittivity; the processor receiving this value may, over time, detect changes in the relative permittivity of the appliance material resulting from air bubbles or cracks in the appliance. The processor may include one or more thresholds indicating use and/or defect. In FIG. 26, the defects 2712 are inclusions or manufacturing defects; defects may develop with use and/or with storage, including delamination of different layers of the device, tearing of the device, inclusion of air bubbles, etc. These defects may negatively impact the appliance performance and/or fit. In some variations the appliance may include a material that may adversely take up water (saliva), particularly in regions that are supposed to remain sealed off. For example, a sealed region for holding electrical components (batteries, wires, electronics, etc.) may be inadvertently opened, exposing it to saliva; one or more sensors may detect this failure mode and alert the patient and/or caregiver. In variations including a mandibular repositioning feature, for example, a cavity or region of the appliance (e.g., in a hollow region) may collect saliva, which may be undesirable (e.g., allowing bacterial growth, etc.). One or more sensors may detect the collection of fluid. Alternatively or additionally, any of these apparatuses may include one or more sensors configured to detect bacterial growth or other contamination.

In any of these variations, the appliance may include one or more temperature sensors that may be used to monitor storage temperature. A temperature sensor on the device may be configured to monitor temperature of the device to indicate that the storage temperature does not exceed a range for safe storage (e.g., greater than 120 degrees F., greater than 125 degrees F., greater than 130 degrees F., greater than 140 degrees F., greater than 150 degrees F., greater than 160 degrees F., greater than 170 degrees F., etc., and/or less than 50 degrees F., less than 40 degrees F., less than 30 degrees F., less than 20 degrees F., less than 10 degrees F., less than 5 degrees F., less than 0 degrees F., etc.).

FIGS. 27A-27F illustrate another example of an orthodontic appliance, configured as a palatal expander, that may be configured for monitoring of the treatment plan and closed-loop (or semi-closed loop) modification of the treatment plan. For example, FIGS. 27A-27F show examples of a palatal expander device 2800 that can include any number or type of sensor 2808 to determine an expansion state of the palatal expander device based on sensor data. This sensor data may be compared to a treatment plan as described above.

Figure 27A:
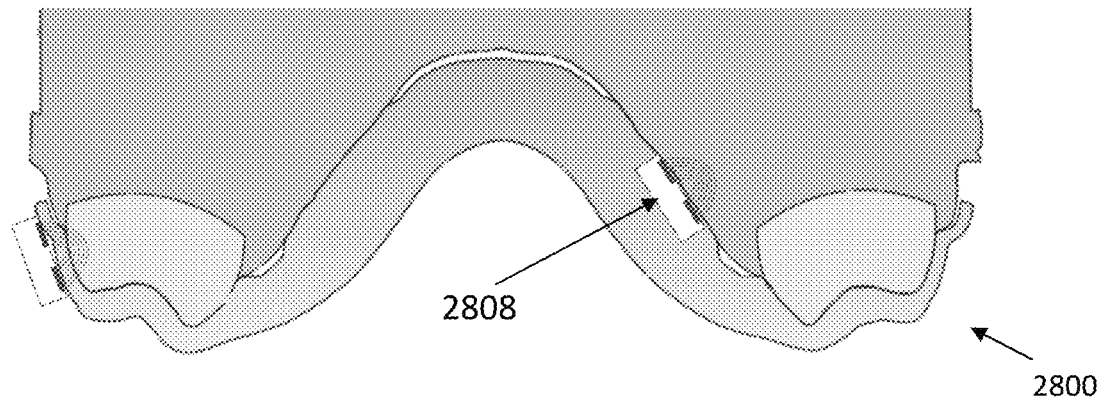
FIGS. 27A-27F show examples of a palatal expander device that can include any number or type of sensor to determine an expansion state of the palatal expander device based on sensor data. These appliances may also be used as a part of a system for closed-loop (or semi-closed loop) modification of a treatment plan.
Figure 27B:
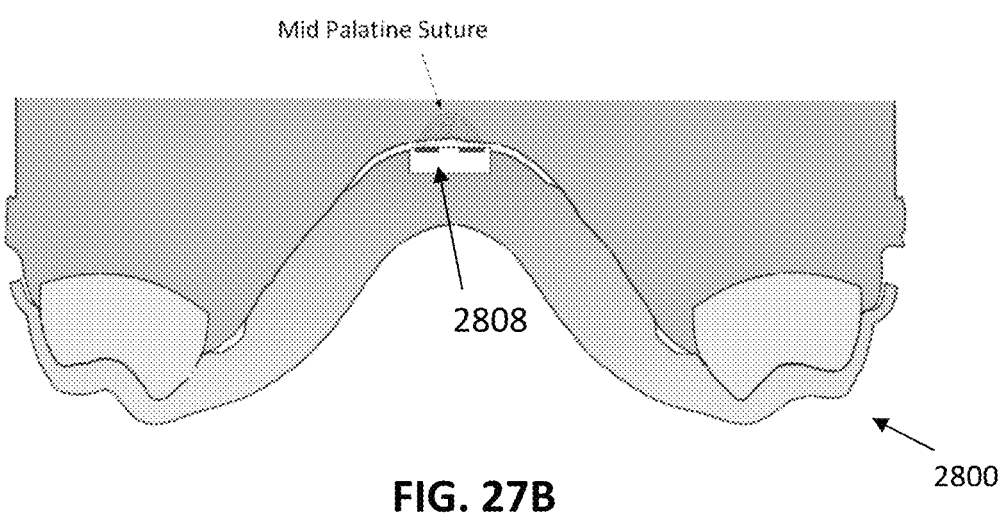
Figure 27C:
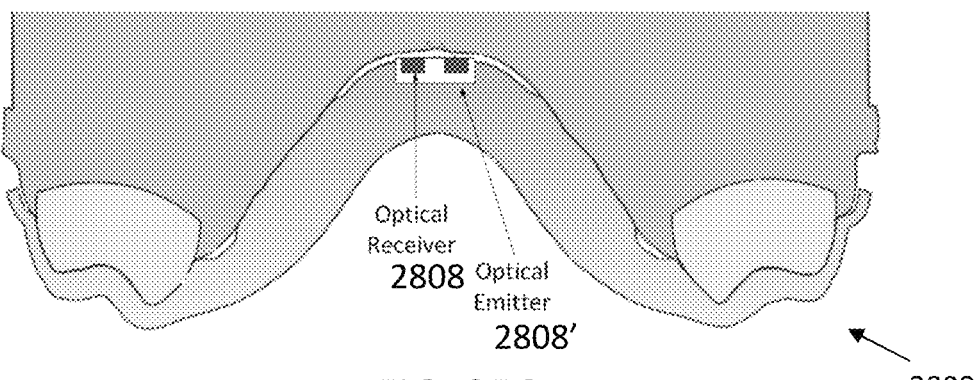

In FIG. 27B, the sensor may comprise an optical sensor (emitter and detector) that may determine the suture opening based on light contract between either soft-hard tissue or the blood stream. In some variations, an ultrasonic sensor may be used. The palatal expander device 2800 of FIG. 27C includes a sensor 2808 comprising a plurality of capacitive electrodes. As mentioned, this apparatus may be configured to detect the extent of the mucosa tissue at the mid palatine raphe, allowing the processor to detect the mid palatal suture opening when the sensor applied an electrostatic field using the capacitive electrodes on the appliance, positioned opposite from the soft palate region, as shown in FIG. 27B. Using this technique the palatal expansion can be monitored during the treatment without need to take CTs. In general, the apparatuses and methods described herein, in particular the palatal expanders, may allow direct monitoring, in real time, of the suture.

Figure 27D:
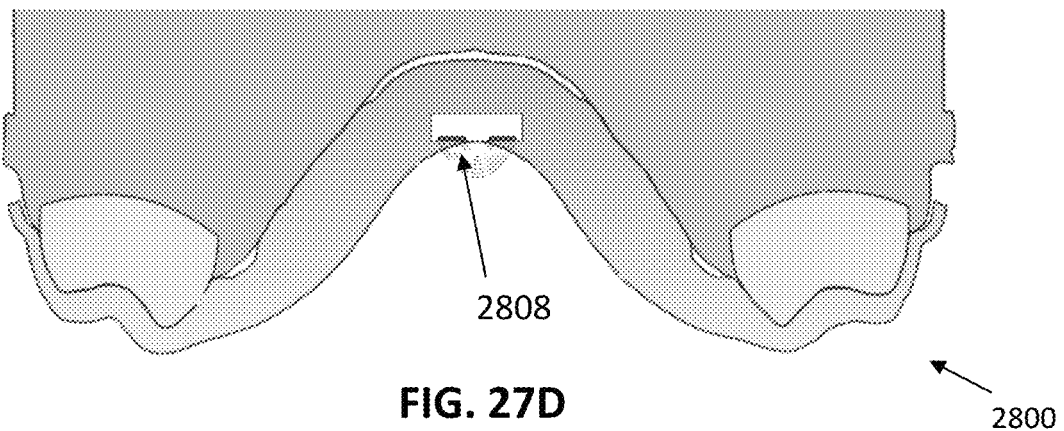

Referring to the example of FIG. 27D, a sensor 2808 comprising one or more capacitive electrodes to provide values that can be used by the processor to monitor the change in the deformation of palatal expander to determine how much and at what rate the expansion happens. This can be measured by tracking the change of capacity measured between the capacitive sensor electrodes in the expander device. The sensor should be positioned on palatal expander in a way that the distance between the capacitive electrodes changes while the expansion happens. For example, the sensor 2808 can be placed midline of trans-palatal segment. Ultrasonic sensors can also be used an alternative to capacitive electrodes to track the expansion of the palatal expander.

Any of the apparatuses described herein may be configured to detect a failure (e.g., failure mode) of the apparatus, such as a palatal expander apparatus. For example, a palatal expander such as those described herein may fail if the palatal region deforms under the force (pressure) exerted on the apparatus when inserted into the patient's mouth. One or more sensors on the apparatus, such as those described in reference to FIG. 27D, may detect the deformation, based, e.g., on the position of various regions of the device relative to each other, such as the position of the left half of the palatal region relative to the right half. Similarly, the device shown in FIG. 27F may be used to directly detect the force applied by the apparatus, e.g., if no force is applied or if lower than an expected threshold (e.g., lower than 8N) is being applied.

Figure 27E:
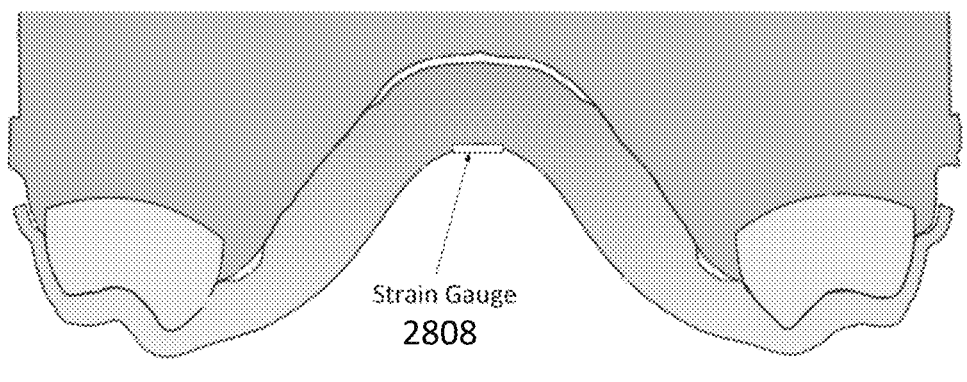
Figure 27F:
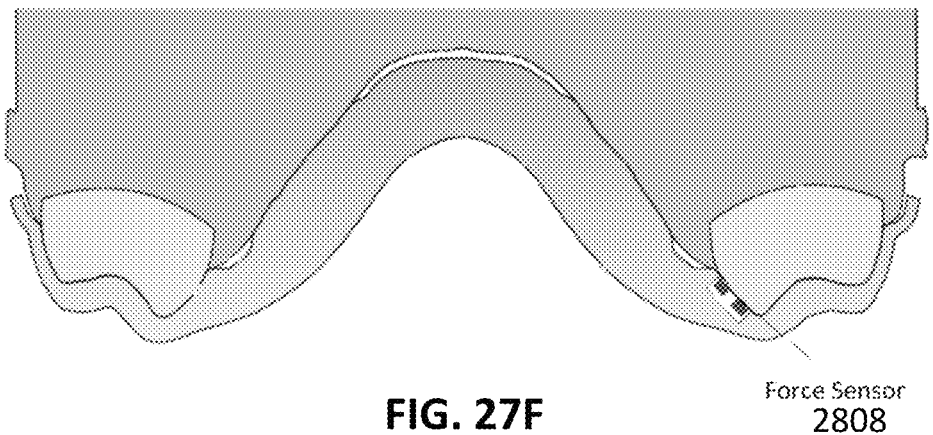

Referring to FIGS. 27E and 27F, sensors 2808 comprising strain gauges or force sensors can be placed at force application regions, such as the lingual side of crowns, or the palatal contact regions, to monitor expansion force of the palatal expander device. The sensor data from the strain gauges or force sensors can be used to determine an expansion state of the device.

Figure 28:
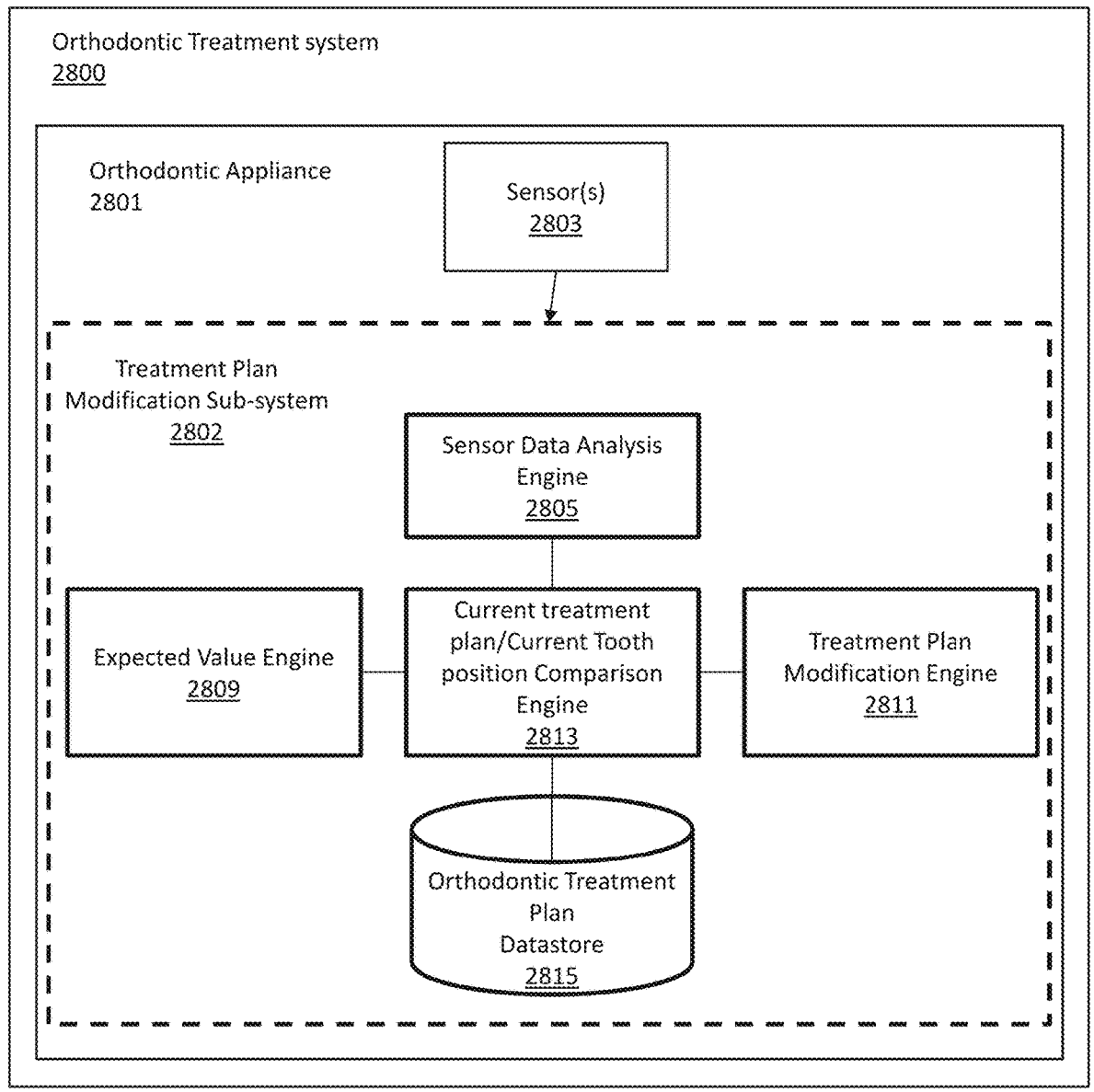
FIG. 28 is a schematic illustration of one example of a system as described herein.

FIG. 28 shows one example of a system as described herein for a system for treating a patients teeth based on a treatment plan. In this example, the system 2800 (e.g., orthodontic treatment system) includes at least one orthodontic appliance 2801 and a treatment plan modification sub-system 2802 that may be directly or indirectly coupled with the orthodontic device(s). For example, the treatment plan modification subsystem may be wired or wirelessly connected (or portions of it may be wired or wirelessly connected) to the orthodontic appliance(s). In any of these variations, the at least one orthodontic appliance may correspond to a treatment stage in a treatment plan, as described above, such as an aligner, a palatal expander, etc. In general, the orthodontic appliance 2801 includes one or more sensors that is in communication with the treatment plan modification subsystem.

The treatment plan modification subsystem may include or be executable on one or more processor, which may be in communication with the one or more sensors, and may include a sensor data analysis engine 2805 that receives sensor data from one or more sensors of an orthodontic appliance. The sensor data analysis engine may determine a force and/or position of one or more of the patient's teeth based on the sensor data. The treatment plan subsystem may also include a memory (e.g., data structure) that stores information about the patient's use of the one or more appliances (e.g., how long each appliance in a treatment plan has been worn, the location of the sensor(s), a look-up table converting sensor output with force and/or position, etc.) In some variations the sensor data analysis engine is configured to determine which teeth are experiencing force above a threshold value from the appliance.

The treatment plan modification subsystem may include an expected value engine that is configured to analyze an existing treatment plan; the original/existing treatment plan may be stored in a memory accessible by the treatment plan modification sub-system, including a data store (e.g., orthodontic treatment plan datastore 2815). The treatment plan may be interpreted and analyzed by the expected value engine 2809 so that it may be compared to the sensor data by the current treatment plan/current tooth position comparison engine 2813. For example, the expected value engine may determine from the original treatment plan what range of sensor values to expect based on the current stage of the treatment plan. The current stage of the treatment plan may be provided (e.g., from a memory accessible to the treatment plan modification sub-system) and/or may be read from the orthodontic treatment device itself.

Thus, the treatment plan modification subsystem (e.g., the expected value engine) may determine an expected value or a range of expected values for the one or more sensors from the orthodontic treatment plan. The Current treatment plan/Current Tooth position Comparison Engine 2813 may then compare the determined expected value(s) to the sensor data for each of the one or more sensors. The treatment plan modification engine 2811 may then be used to modify the treatment plan if the sensor data does not match the determined expected value(s).

As mentioned above, FIG. 28 shows an example of an orthodontic treatment system 2800, including a treatment plan modification sub-system 2802. The modules of the treatment plan modification sub-system may include one or more engines and datastores. A computer system (including the sub-system) can be implemented as an engine, as part of an engine or through multiple engines. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The treatment plan modification sub-system, including any of the engines forming the system/sub-system, may implement one or more automated agents When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An orthodontic system for treating a patient's teeth based on a treatment plan, the orthodontic system comprising:
   at least one orthodontic appliance, wherein the at least one orthodontic appliance corresponds to a treatment stage in the treatment plan, further wherein the at least one orthodontic appliance comprises one or more sensors; and
   a processor in communication with the one or more sensors, wherein the processor is configured to:
      receive sensor data from the one or more sensors, the sensor data corresponding to a force acting on one or more teeth;
      predict tooth movement based on the sensor data, wherein the predicted tooth movement is determined by predicting how much the one or more teeth will move based on a direction and a magnitude of the force;
      compare the predicted tooth movement to an expected tooth movement, wherein the expected tooth movement is based on the treatment stage of the treatment plan; and
      modify the treatment plan if the predicted tooth movement does not match the expected tooth movement based on the treatment stage of the treatment plan.

2. The orthodontic system of claim 1, wherein the at least one orthodontic appliance comprises a transmitter to transmit the sensor data from the one or more sensors to the processor, wherein the processor is remote to the at least one orthodontic appliance.

3. The orthodontic system of claim 2, wherein the at least one orthodontic appliance is configured to transmit a timestamp associated with the sensor data.

4. The orthodontic system of claim 1, wherein the processor is on the at least one orthodontic appliance.

5. The orthodontic system of claim 1, wherein the at least one orthodontic appliance comprises a series of orthodontic appliances each corresponding to a different stage of the treatment plan.

6. The orthodontic system of claim 1, wherein the one or more sensors comprises one or more force-dependent resistive materials.

7. The orthodontic system of claim 6, wherein the one or more force-dependent resistive materials comprises a pressure-dependent resistive film on an inner surface of the at least one orthodontic appliance.

8. The orthodontic system of claim 1, wherein the one or more sensors is located on one or more of a buccal, a lingual, and an occlusal surface of tooth-receiving cavities of the at least one orthodontic appliance.

9. The orthodontic system of claim 1, further comprising a battery.

10. The orthodontic system of claim 1, wherein comparing the predicted tooth movement to the expected tooth movement comprises determining if the predicted tooth movement is not within a predetermined range of the expected tooth movement.

11. The orthodontic system of claim 1, further comprising at least one motion sensor configured to generate data representative of jaw movement patterns.

12. The orthodontic system of claim 1, wherein how much the one or more teeth will move is further predicted based on a location of the one or more sensors.

13. The orthodontic system of claim 1, wherein the one or more sensors are configured to sense force acting on one or more attachments attached to the one or more teeth.

14. An orthodontic system for treating a patient's teeth based on a treatment plan, the orthodontic system comprising:
   at least one orthodontic appliance, wherein the at least one orthodontic appliance corresponds to a treatment stage in the treatment plan, further wherein the at least one orthodontic appliance comprises one or more sensors; and
   a processor in communication with the one or more sensors, wherein the processor is configured to:
      receive sensor data from the one or more sensors of the at least one orthodontic appliance, the sensor data corresponding to a force acting on one or more teeth, wherein the one or more sensors comprise one or more force-dependent resistive materials on the orthodontic appliance;
      predict tooth movement based on the sensor data, wherein predicting the tooth movement comprises predicting how much the one or more teeth will move based on a direction and a magnitude of the force;
      determine an expected tooth movement based on the treatment stage of the treatment plan;
      compare the predicted tooth movement to the expected tooth movement to determine whether the predicted tooth movement matches the expected tooth movement; and
      modify the treatment plan if the predicted tooth movement does not match the expected tooth movement.

15. The orthodontic system of claim 14, wherein the processor is on the at least one orthodontic appliance.

16. The orthodontic system of claim 14, wherein the at least one orthodontic appliance comprises a transmitter to transmit the sensor data from the one or more sensors to the processor, wherein the processor is remote to the at least one orthodontic appliance.

17. The orthodontic system of claim 16, wherein the at least one orthodontic appliance is configured to transmit a timestamp associated with the sensor data.

18. The orthodontic system of claim 14, wherein the at least one orthodontic appliance comprises a series of orthodontic appliances.

19. The orthodontic system of claim 18, wherein each of the series of orthodontic appliances correspond to a different stage of the treatment plan.

20. The orthodontic system of claim 14, wherein the processor is part of a monitoring circuitry, wherein the orthodontic system further comprises a switch that is configured to electrically couple the monitoring circuitry to a power source when the switch is triggered.

* * * * *